US012630846B2

(12) United States Patent
Zhang et al.

(10) Patent No.: US 12,630,846 B2
(45) Date of Patent: May 19, 2026

(54) **TYPE I-C CRISPR SYSTEM FROM *NEISSERIA LACTAMICA* AND METHODS OF USE**

(71) Applicants: THE REGENTS OF THE UNIVERSITY OF MICHIGAN, Ann Arbor, MI (US); CORNELL UNIVERSITY, Ithaca, NY (US)

(72) Inventors: Yan Zhang, Ann Arbor, MI (US); Ailong Ke, Ithaca, NY (US); Ryan Krueger, Ann Arbor, MI (US); Zhonggang Hou, Ann Arbor, MI (US)

(73) Assignees: THE REGENTS OF THE UNIVERSITY OF MICHIGAN, Ann Arbor, MI (US); CORNELL UNIVERSITY, Ithaca, NY (US)

( * ) Notice: Subject to any disclaimer, the term of this patent is extended or adjusted under 35 U.S.C. 154(b) by 601 days.

(21) Appl. No.: 18/000,676

(22) PCT Filed: May 26, 2021

(86) PCT No.: PCT/US2021/034165
§ 371 (c)(1),
(2) Date: Dec. 2, 2022

(87) PCT Pub. No.: WO2021/247301
PCT Pub. Date: Dec. 9, 2021

(65) Prior Publication Data
US 2023/0287457 A1      Sep. 14, 2023

Related U.S. Application Data

(60) Provisional application No. 63/035,099, filed on Jun. 5, 2020.

(51) Int. Cl.
| | |
|---|---|
| *C12N 15/90* | (2006.01) |
| *C12N 9/22* | (2006.01) |
| *C12N 15/11* | (2006.01) |
| *C12N 15/70* | (2006.01) |

(52) U.S. Cl.
CPC ............ *C12N 15/907* (2013.01); *C12N 9/22* (2013.01); *C12N 15/11* (2013.01); *C12N 15/70* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 5,034,506 A | 7/1991 | Summerton et al. |
| 8,697,359 B1 | 4/2014 | Zhang |
| 8,771,945 B1 | 7/2014 | Zhang |
| 8,945,839 B2 | 2/2015 | Zhang |
| 2010/0076057 A1 | 3/2010 | Sontheimer et al. |
| 2011/0189776 A1 | 8/2011 | Terns et al. |
| 2011/0223638 A1 | 9/2011 | Wiedenheft et al. |
| 2013/0130248 A1 | 5/2013 | Haurwitz et al. |
| 2014/0068797 A1 | 3/2014 | Doudna et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0199767 A1 | 7/2014 | Barrangou et al. |
| 2014/0201857 A1 | 7/2014 | Fahrenkrug et al. |
| 2014/0212869 A1 | 7/2014 | Sampas et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0248702 A1 | 9/2014 | Zhang et al. |
| 2014/0256046 A1 | 9/2014 | Zhang et al. |
| 2014/0271987 A1 | 9/2014 | Manoury et al. |
| 2014/0273230 A1 | 9/2014 | Chen et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |

(Continued)

FOREIGN PATENT DOCUMENTS

| | | |
|---|---|---|
| WO | WO 2008/108989 | 9/2008 |
| WO | WO 2010/054108 | 5/2010 |

(Continued)

OTHER PUBLICATIONS

Zhang et al. Processing-independent CRISPR RNAs limit natural transformation in Neisseria meningitidis. Mol Cell. May 23, 2013; 50(4):488-503 (Year: 2013).*

Louwen et al. The role of CRISPR-Cas systems in virulence of pathogenic bacteria. Microbiol Mol Biol Rev. Mar. 2014;78(1):74-88 (Year: 2014).*

Liu et al. Chemistry of Class 1 CRISPR-Cas effectors: Binding, editing, and regulation. J Biol Chem. Oct. 16, 2020;295(42):14473-14487 (Year: 2020).*

International Search Report and Written Opinion for PCT/US2021/034165. Mailed Oct. 6, 2021. 9 pages.

International Preliminary Report on Patentability for PCT-US2021-034165. Mailed Dec. 15, 2022. 8 pages.

(Continued)

*Primary Examiner* — Christopher M Babic

(74) *Attorney, Agent, or Firm* — Casimir Jones, S.C.; Kelly A. Barton

(57)          ABSTRACT

The disclosure provides a method of altering a DNA sequence, which method comprises the use of a type I-C CRISPR-Cas system based on *Neisseria lactamica*. The system involves a combination of two or more *Neisseria lactamica* proteins selected from Cas3, Cas5, Cas8c, and Cas7 and a synthetic guide RNA sequence.

19 Claims, 31 Drawing Sheets

Figure 1A:
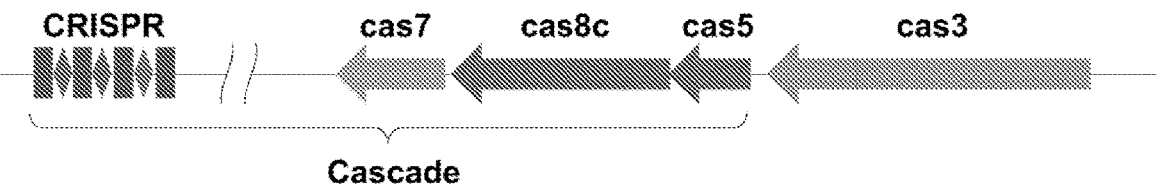

Specification includes a Sequence Listing.

(56) References Cited

U.S. PATENT DOCUMENTS

| | | | |
|---|---|---|---|
| 2014/0294773 A1 | 10/2014 | Brouns et al. | |
| 2014/0295556 A1 | 10/2014 | Joung et al. | |
| 2014/0298547 A1 | 10/2014 | Sastry-Dent et al. | |
| 2014/0304853 A1 | 10/2014 | Ainley et al. | |
| 2014/0309487 A1 | 10/2014 | Lee et al. | |
| 2014/0310828 A1 | 10/2014 | Lee et al. | |
| 2014/0310830 A1 | 10/2014 | Zhang et al. | |
| 2014/0315985 A1 | 10/2014 | May et al. | |
| 2014/0335063 A1 | 11/2014 | Cannon et al. | |
| 2014/0335620 A1 | 11/2014 | Zhang et al. | |
| 2014/0349400 A1 | 11/2014 | Jakimo et al. | |
| 2014/0357530 A1 | 12/2014 | Zhang et al. | |
| 2014/0377868 A1 | 12/2014 | Joung et al. | |
| 2015/0024500 A1 | 1/2015 | Yu et al. | |
| 2015/0031134 A1 | 1/2015 | Zhang et al. | |
| 2015/0045546 A1 | 2/2015 | Siksnys et al. | |
| 2015/0050699 A1 | 2/2015 | Siksnys et al. | |
| 2018/0334688 A1* | 11/2018 | Gersbach | C12N 15/52 |

FOREIGN PATENT DOCUMENTS

| | | |
|---|---|---|
| WO | WO 2012/164565 | 12/2012 |
| WO | WO 2013/098244 | 7/2013 |
| WO | WO 2013/176772 | 11/2013 |
| WO | WO 2014/190181 | 11/2014 |
| WO | WO 2019/246555 | 12/2019 |

OTHER PUBLICATIONS

Al-Attar et al., Clustered regularly interspaced short palindromic repeats (CRISPRs): the hallmark of an ingenious antiviral defense mechanism in prokaryotes. Biol Chem. Apr. 2011;392(4):277-89.

Ausubel et al., Current Protocols in Molecular Biology, Greene Publishing Associates and John Wiley & Sons, New York. 2003. TOC only. 19 pages.

Barrangou et al., CRISPR provides acquired resistance against viruses in prokaryotes. Science. Mar. 23, 2007;315(5819):1709-12.

Bhaya et al., CRISPR-Cas systems in bacteria and archaea: versatile small RNAs for adaptive defense and regulation. Annu Rev Genet. 2011;45:273-97.

Biswas et al., CRISPRTarget: bioinformatic prediction and analysis of crRNA targets. RNA Biol. May 2013;10(5):817-27.

Bolotin et al., Clustered regularly interspaced short palindrome repeats (CRISPRs) have spacers of extrachromosomal origin. Microbiology (Reading). Aug. 2005;151(Pt 8):2551-2561.

Braasch et al., Novel antisense and peptide nucleic acid strategies for controlling gene expression. Biochemistry. Apr. 9, 2002;41(14):4503-10.

Bratcher et al., Evolutionary and genomic insights into meningococcal biology. Future Microbiol. Jul. 2012;7(7):873-85.

Brouns et al., Small CRISPR RNAs guide antiviral defense in prokaryotes. Science. Aug. 15, 2008;321(5891):960-4.

Carroll. A CRISPR approach to gene targeting. Mol Ther. Sep. 2012;20(9):1658-60.

Carte et al., Cas6 is an endoribonuclease that generates guide RNAs for invader defense in prokaryotes. Genes Dev. Dec. 15, 2008;22(24):3489-96.

Chial. Rare Genetic Disorders: Learning About Genetic Disease Through Gene Mapping, SNPs, and Microarray Data, Nature Education. 2008; 1(1):192. 5 pages.

Cho et al., Targeted genome engineering in human cells with the Cas9 RNA-guided endonuclease. Nat Biotechnol. Mar. 2013;31(3):230-2.

Cong et al., Multiplex genome engineering using CRISPR/Cas systems. Science. Feb. 15, 2013;339(6121):819-23.

Crooks et al., WebLogo: a sequence logo generator. Genome Res. Jun. 2004;14(6):1188-90.

Deltcheva et al., CRISPR RNA maturation by trans-encoded small RNA and host factor RNase III. Nature. Mar. 31, 2011;471(7340):602-7.

Deveau et al., CRISPR/Cas system and its role in phage-bacteria interactions. Annu Rev Microbiol. 2010;64:475-93.

Dolan et al., Introducing a Spectrum of Long-Range Genomic Deletions in Human Embryonic Stem Cells Using Type I CRISPR-Cas. Mol Cell. Jun. 6, 2019;74(5):936-950.e5.

Doty et al., Strand separation and specific recombination in deoxyribonucleic acids: physical chemical studies. Proc Natl Acad Sci USA. Apr. 1960;46(4):461-76.

Garneau et al., The CRISPR/Cas bacterial immune system cleaves bacteriophage and plasmid DNA. Nature. Nov. 4, 2010;468(7320):67-71.

Gasiunas et al., Cas9-crRNA ribonucleoprotein complex mediates specific DNA cleavage for adaptive immunity in bacteria. Proc Natl Acad Sci U S A. Sep. 25, 2012;109(39):E2579-86.

Goeddel, Gene Expression Technology: Methods in Enzymology, vol. 185, Academic Press, San Diego, Calif. 1990. TOC only. 7 pages.

Hale et al., RNA-guided RNA cleavage by a CRISPR RNA-Cas protein complex. Cell. Nov. 25, 2009;139(5):945-56.

Hale et al., Essential features and rational design of CRISPR RNAS that function with the Cas RAMP module complex to cleave RNAs. Mol Cell. Feb. 10, 2012;45(3):292-302.

Horvath et al., CRISPR/Cas, the immune system of bacteria and archaea. Science. Jan. 8, 2010;327(5962):167-70.

Human Gene Mutation Database (HGMD). www.hgmd.cf.ac.uk. Retrieved from the internet Mar. 3, 2023. 2 pages.

Hwang et al., Efficient genome editing in zebrafish using a CRISPR-Cas system. Nat Biotechnol. Mar. 2013;31(3):227-9.

Invitrogen et al., Geneart crispr nuclease mRNA ready to transfect wild-type cas9 mrna, catalog No. a29378. Dec. 31, 2015. Publicaiton No. man0014587. pp. 1-34.

Jiang et al., RNA-guided editing of bacterial genomes using CRISPR-Cas systems. Nat Biotechnol. Mar. 2013;31(3):233-9.

Jinek et al., RNA-programmed genome editing in human cells. Elife. Jan. 29, 2013;2:e00471. 9 pages.

Jinek et al., A Programmable Dual-RNA-Guided DNA Endonuclease in Adaptive Bacterial Immunity. Science, 2012; 337: 816-821.

Kim et al., Highly efficient RNA-guided genome editing in human cells via delivery of purified Cas9 ribonucleoproteins. Genome Res. Jun. 2014;24(6):1012-9.

Kitts et al., A method for producing recombinant baculovirus expression vectors at high frequency. Biotechniques. May 1993;14(5):810-7.

Lehninger, Principles of Biochemistry. Worth Pub. 1982. pp. 793-800.

Louwen et al., The role of CRISPR-Cas systems in virulence of pathogenic bacteria. Microbiol Mol Biol Rev. Mar. 2014;78(1):74-88.

Lucklow et al., Efficient generation of infectious recombinant baculoviruses by site-specific transposon-mediated insertion of foreign genes into a baculovirus genome propagated in *Escherichia coli*. J Virol. Aug. 1993;67(8):4566-79.

Lucklow. Baculovirus systems for the expression of human gene products. Curr Opin Biotechnol. Oct. 1993;4(5):564-72.

Makarova et al., Evolution and classification of the CRISPR-Cas systems. Nat Rev Microbiol. Jun. 2011;9(6):467-77.

Makarova et al., Evolutionary classification of CRISPR-Cas systems: a burst of class 2 and derived variants. Nat Rev Microbiol. Feb. 2020;18(2):67-83.

Makarova et al., Annotation and Classification of CRISPR-Cas Systems. Methods Mol Biol. 2015;1311:47-75.

Mali et al., RNA-Guided Human Genome Engineering via Cas9. Science. 2013; 339(6121):823-826.

Marmur et al., Strand separation and specific recombination in deoxyribonucleic acids: biological studies. Proc Natl Acad Sci U S A. Apr. 1960;46(4):453-61.

Mojica et al., Intervening sequences of regularly spaced prokaryotic repeats derive from foreign genetic elements. J Mol Evol. Feb. 2005;60(2):174-82.

Mout et al., Direct Cytosolic Delivery of CRISPR/Cas9-Ribonucleoprotein for Efficient Gene Editing. ACS Nano. Mar. 28, 2017;11(3):2452-2458.

(56) References Cited

OTHER PUBLICATIONS

Rotman et al., The genetics of Neisseria species. Annu Rev Genet. 2014;48:405-31.

Sambrook et al., Molecular Cloning, a Laboratory Manual, 3rd edition, Cold Spring Harbor Press, Cold Spring Harbor, N.Y. 2001. TOC only. 23 pages.

Sapranauskas et al., The *Streptococcus thermophilus* CRISPR/Cas system provides immunity in *Escherichia coli*. Nucleic Acids Res. Nov. 2011;39(21):9275-82.

Schulz and Schirmer, Principles of Protein Structure, Springer-Verlag, New York. 1979. TOC only. 11 pages.

Sinkunas et al., Cas3 is a single-stranded DNA nuclease and ATP-dependent helicase in the CRISPR/Cas immune system. EMBO J. Apr. 6, 2011;30(7):1335-42.

Urlaub et al., Isolation of Chinese hamster cell mutants deficient in dihydrofolate reductase activity. Proc Natl Acad Sci U S A. Jul. 1980;77(7):4216-20.

Wahlestedt et al., Potent and nontoxic antisense oligonucleotides containing locked nucleic acids. Proc Natl Acad Sci U S A. May 9, 2000;97(10):5633-8.

Wang et al., Cyclohexene Nucleic Acids (CeNA): Serum Stable Oligonucleotides that Activate RNase H and Increase Duplex Stability with Complementary RNA. J. Am. Chem. Soc., 2000; 122: 8595-8602.

Wiedenheft et al., RNA-guided genetic silencing systems in bacteria and archaea. Nature. Feb. 15, 2012;482(7385):331-8.

Zhang. The CRISPR-Cas9 system in *Neisseria* spp. Pathog Dis. Jun. 1, 2017;75(4):ftx036. pp. 1-10.

Zuris et al., Cationic lipid-mediated delivery of proteins enables efficient protein-based genome editing in vitro and in vivo. Nat Biotechnol. Jan. 2015;33(1):73-80.

Morisaka et al., "CRISPR-Cas3 induces broad and unidirectional genome editing in human cells." Nature Communications 2019, 13 pages.

Extended European Search Report and Written Opinion mailed Jun. 7, 2024, European Application No. 21818747.4, 8 pages.

* cited by examiner

Figure 3C
Figure 3D
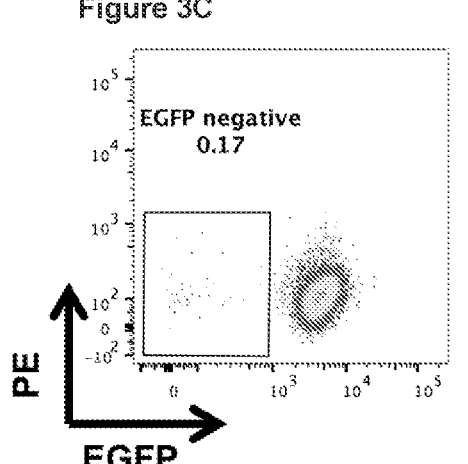
Figure 3E
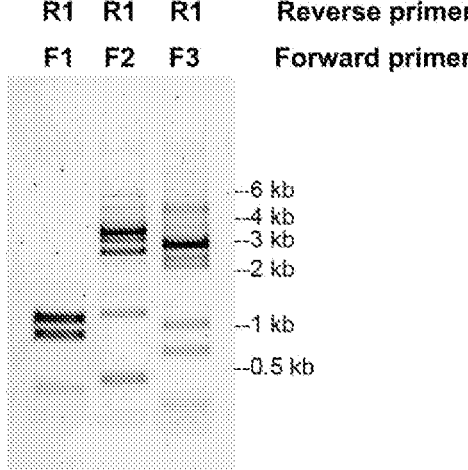

CRISPR

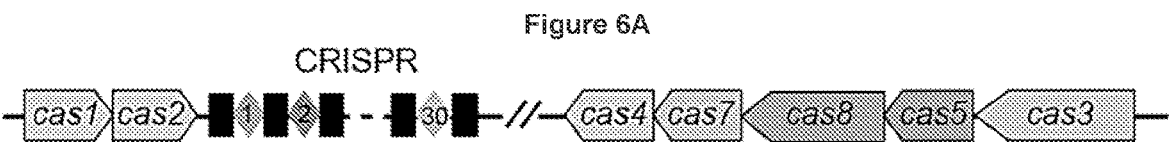

Figure 6B

```
          ▓
         ┃┃ C
        ┃┃┃┃
CTTTTCATTT  -  CATGAAAAACCCTTTTTCGATAAATACGGCGTTC  -  GTGTAAGTCT
ATGGCGTTTT  -  TATAGATTGGTTGTCATTCACGATGCACGAAGAT  -  TCCTTGATGA
CGCGCTGTTC  -  CTTGTCTTAATAGTAACAACTGCATTGAGACCGCA  -  AACAGCGGCG
GAGACTTCAA  -  AAAAAACCATACCGACCCCCACGGCGCGGCAGGAA  -  GTTGCCGCGC
CTTTTCATTT  -  CATGAAAAACCTTTTTCGATAAATACGGCGTTC  -  GTGTAAGTCT
GCGTGGCTTC  -  CGCCAGCAGTTCGGTGGCGCGTTGCTCAATACGGG  -  CTAGCTCTAA
ACGGCGTTTT  -  TATAGATTGGTTGTCATTTACGATGCACGAAGAT  -  TCTTTGCTGA
ATATATTTTC  -  AGTTGACGGCGTATGCCCCGAACCTAAAAGCGTA  -  GATTTCGGCA
TCGTGGTTTC  -  CCGCCACAAATACCACCACCGCCTCGCTGCCCAC  -  CGGCGGATGT
ATATATTTTC  -  AGTTGACGGCGTATGCCCCGAACCTAGAAGCGTA  -  GATTTCGGCA
GCGGCGGTTC  -  AGACACACGCCCGAAGCATCAACGGCTTGGAGGC  -  GCAATACACG
GGAGACTTCA  -  AAAAAACCACACCGACCCCCACGGCGCAGCAGGAA  -  GTTGCCGCGC
CCCTGCCTTC  -  GATACGGGGGCGGTAGTCGTCCTCTGTTAAATAGG  -  CGGCTTTGCG
CGAGAAATTC  -  AACGAAATCAACAATTATCTCGGCGGCTTTGGTA  -  ACACAATGCT
GGAGACTTCA  -  AAAAAACCATACCGACCCCCACGGCGCGGCAGGAA  -  GTTGCCGCGC
TTTCTAATTC  -  GTATTGAAGAAACCGGTTACATATACGCAGCAAAC  -  GGGAATGGCG
AGAACGATTC  -  ACCCATGCAAAGCAGCTTGTAGCCTATCTAGGAC  -  TTGACCCCAA
TGCAGTTTTC  -  CGTCTTCGCCGCGCTGAAAAACGCTTATTTCGCC  -  GCGCCAGCAG
CGCGCTCTTC  -  CTTGTCTTAATAGTAACAACTGCATTGAGACCGCA  -  AACAGCGGCG
CTTTTCATTT  -  CATGAAAAACCTTTTTCGATAAATACGGCGTTC  -  GAGTAAGTCT
AGGCGATTTC  -  AGCGCAGCCGTAGTCAACGCAGCGGCAGCCAAGG  -  CAGCAACAGC
AATCGTATTC  -  AGTAGTAGAGCTGCCCAATGCGTTGCCTTGGGAGC  -  TGTCTAAGGG
TTTCTAATTC  -  GTATTGAAGAAACCGGTTACAGATACGCAGCAAAC  -  GGAAACGGCG
ATATATTTTC  -  AGTTGACGGCGTATGCCCCGAACCTAGAAGCGTA  -  GATTTCGGAA
ACCGACTTC  -  ATCAAGCCCCATATCCAAGAAACAATAAACCACT  -  TCACACAACT
AATCATATTC  -  AGTAGTAGAGCTGCCCAATGCGTTGCCTTGGGAGC  -  TGTCTAAGGG
GTGTTGAAAC  -  AGACGCACGCCCGAAGCATCAACGGCTTGGAGGC  -  TCAGCCGCCT
ACGGCGTTTT  -  TATAGATTGGTTGTCATTCACGATGCACGAAGAT  -  TCCTTGCTGA
```

5' flank            protospacers           3' flank

Interference assay
in *E.coli*

Not induced          Induced test plates
(Kan+Amp+Cm+Sp)

control plates
(Kan+Amp+Cm)

Test Plate
-1 -2 -3 -4 -5 -6 -7 -8 empty target #1
(w/ TTC PAM)

```
5'.AGGGCGAGGGCGATGCCACCTACGGCAAGCTGACCCTGAAGT.3' SEQ ID NO: 77
    | | | | | | | | | | | | | | | | | | | | | | | | | | | | | | | | | | | | | | | | |
3'.TCCCGCTCCCGCTACGGTGGATGCCGTTCGACTGGGACTTCA.5' SEQ ID NO: 78
``` protospacer (GFP-G2) - - - PAM

—//— EGFP —//—

—//— tdTomato —//—

PAM ˜˜ protospacer (tdTm-G1) ˜ ˜

```
5'.AGTTCAAGACCATCTACATGGCCAAGAAGCCCGTGCAACTGC.3' SEQ ID NO: 79
    | | | | | | | | | | | | | | | | | | | | | | | | | | | | | | | | | | | | | | | |
3'.TCAAGTTCTGGTAGATGTACCGGTTCTTCGGGCACGTTGACG.5' SEQ ID NO: 80
```

HPRT locus

ATG exon 1

5′..AGTTAAGGGTTTGGGGAAGCACTGGGCCAAGAGTCAGGAAAA..3′ SEQ ID NO: 81

3′..TCAATTCCCAAACCCCTTCGTGACCCGGTTCTCAGTCCTTTT..5′ SEQ ID NO: 82 protospacer (HPRT-G1)    PAM

5′..AGGGGCTTCGCTGGGGGAGCCTCGGCTTCTTCTGGGAGAAAA..3′ SEQ ID NO: 83

3′..TCCCCGAAGCGACCCCCTCGGAGCCGAAGAAGACCCTCTTTT..5′ SEQ ID NO: 84 protospacer (HPRT-G2)    PAM

| Single clone cytotoxicity assay | | | | |
|---|---|---|---|---|
| Cascade | Cas3 | 6-TG | colony counts | survival rate |
| – | – | – | 125, 145, 134 | 0 % |
| – | – | + | 0, 0, 0 | |
| HPRT-G1 | – | – | 133, 123, 125 | 0 % |
| HPRT-G1 | – | + | 0, 0, 0 | |
| HPRT-G1 | + | – | 174, 178, 160 | 78 % |
| HPRT-G1 | + | + | 146, 133, 122 | |
| HPRT-G2 | – | – | 128, 143, 102 | 0 % |
| HPRT-G2 | – | + | 0, 0, 0 | |
| HPRT-G2 | + | – | 142, 131, 105 | 34 % |
| HPRT-G2 | + | + | 38, 55, 36 | |

Figure 8A
HPRT1 locus
HPRT G1
~489 nt
-7.4kF   -5.7kF   -3.3kF   -2.0kF   -1.3kF   -0.6kF        -0.2kR        +1  ATG        +2.3kR  +5.6kR  +6.6kR        +11.3kR        +18.5kR
L        K        J        I        H        G            A                                B  C  D              E                    F
exon 1                                  exon 2  exon 3
Figure 8B
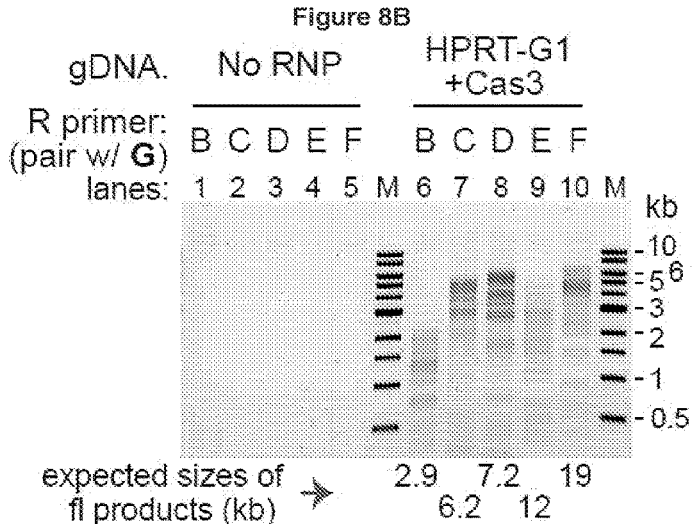
gDNA.          No RNP              HPRT-G1
                                  +Cas3
R primer:
(pair w/ G)   B C D E F        B C D E F
lanes:        1 2 3 4 5 M   6 7 8 9 10 M    kb
                                           -10
                                           -6
                                           -5
                                           -3
                                           -2
                                           -1
                                           -0.5
expected sizes of   →      2.9    7.2    19
fl products (kb)               6.2    12
Figure 8C
HPRT G1 →
~489 nt   +1
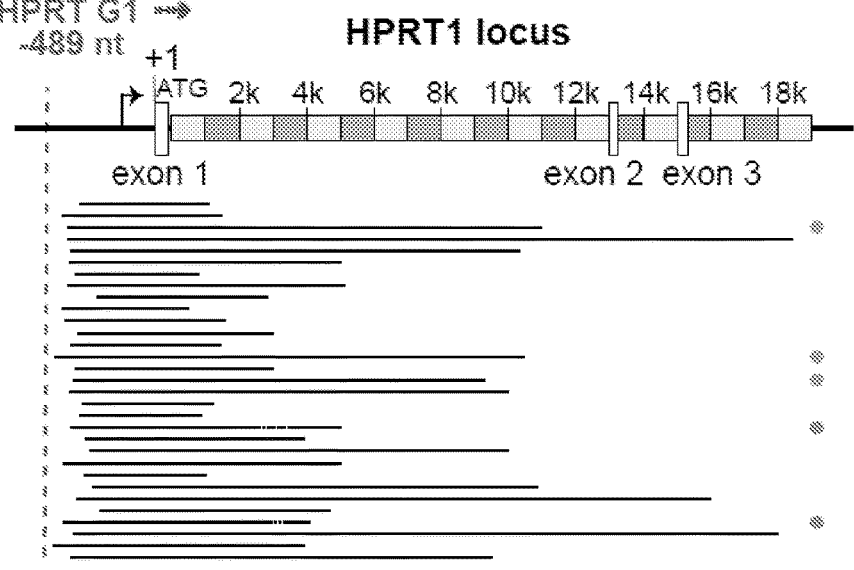
HPRT1 locus
ATG   2k   4k   6k   8k   10k   12k   14k   16k   18k
exon 1                              exon 2   exon 3

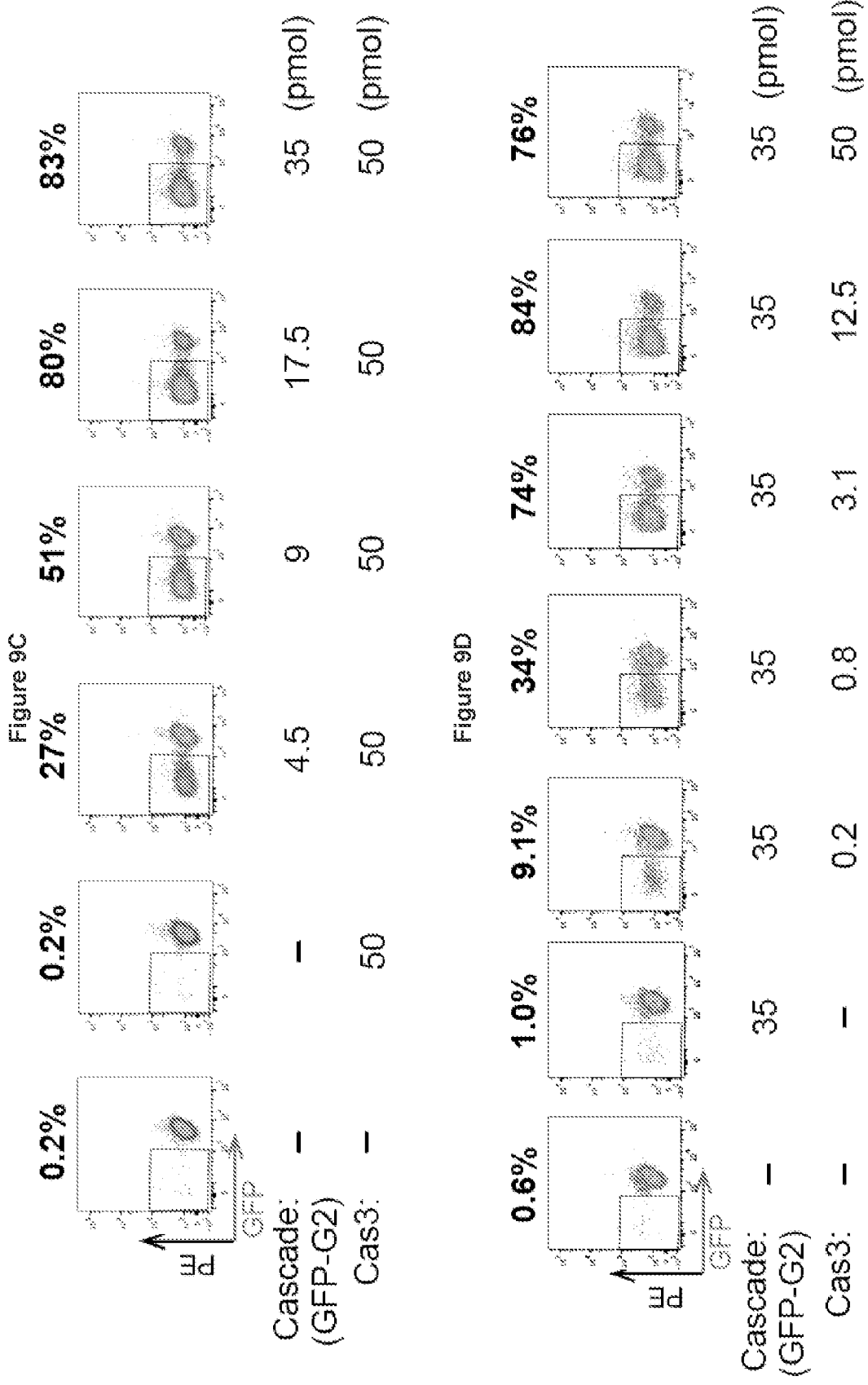

HPRT1 locus

-2.0kF

HPRT G1
-489 nt  +1  +2.3kR

ATG exon 1

|—— 4.3 kb ——|
(full-length amplicon)

| Cell line: | HAP1 | | | | hESC | | | | HEK 293T | | | | HeLa | | | |
|---|---|---|---|---|---|---|---|---|---|---|---|---|---|---|---|---|
| Cascade | – | + | + | M | – | + | + | M | – | + | + | M | – | + | + | M |
| Cas3 | – | – | + | | – | – | + | | – | – | + | | – | – | + | | kb
-10
=5 6
-3
-2
-1
-0.5

**DNMT3B-EGFP
in hESCs**

TYPE I-C CRISPR SYSTEM FROM *NEISSERIA LACTAMICA* AND METHODS OF USE

CROSS-REFERENCE TO RELATED APPLICATIONS

This application claims the benefit of U.S. Provisional Application No. 63/035,099, filed Jun. 5, 2020, the contents of which is herein incorporated by reference in its entirety.

STATEMENT REGARDING FEDERALLY-SPONSORED RESEARCH

This invention was made with Government support under contract numbers GM117268, GM137833, and GM118174 awarded by the National Institutes of Health. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 47,822 Byte ASCII (Text) file named "38388-601_SQL_ST25.txt," created on May 24, 2021.

FIELD

The present invention relates to genome editing methods and systems based on the type I-C CRISPR-Cas system of *Neisseria lactamica.*

BACKGROUND

The Clustered Regularly Interspaced Short Palindromic Repeats (CRISPR) system, originally found in bacteria and archaea, can adaptively resist foreign genetic materials to provide microbial immunity employing RNA-guided protein machineries and intricate molecular mechanisms (Mojica et al., *J. Mol. Evol.*, 60: 174-182 (2005); Bolotin et al., *Microbiology,* 151: 2551-2561 (2005); Barrangou et al., *Science,* 315: 1709-1712 (2007); Garneau et al., *Nature,* 468: 67 (2010); Deltcheva et al., *Nature,* 471: 602 (2011); Sapranauskas et al., *Nucl. Acids Res.,* 39: 9275-9282 (2011); Jinek et al., *Science,* 337: 816-821 (2012); Gasiunas et al., *Proc. Natl. Acad. Sci.* USA, 109: E2579-E2586 (2012); and Wiedenheft et al., *Nature,* 482: 331 (2012)). Recent advances enable harnessing of customized CRISPR systems for genome editing in eukaryotic organisms (Cong et al., *Science,* 339: 819-823 (2013); Mali et al., *Science,* 339: 823-826 (2013); Jiang et al., *Nature Biotech.,* 31: 233-239 (2013); Jinek et al., *Elife,* 2: e00471 (2013); Cho et al., *Nature Biotech.,* 31: 230 (2013); and Hwang et al., *Nature Biotech.,* 31: 227 (2013)). The exemplary type II CRISPR system employs a Cas9 protein in complex with single-guide RNA (sgRNA), forming a programmable endonuclease that cleaves a double-stranded DNA (dsDNA) target. The dsDNA substrate contains a target strand complimentary to the guide sequence in sgRNA (Jinek et al., *Science,* 337: 816-821 (2012)) and a non-target strand bearing a protospacer adjacent motif (PAM) required for target recognition (Mojica et al., *J. Mol. Evol.,* 60: 174-182 (2005); Bolotin et al., *Microbiology,* 151: 2551-2561 (2005)).

In contrast to type II CRISPR loci, types I and III CRISPR loci contain multiple Cas proteins, which form complexes with CRISPR RNAs (crRNA) (CASCADE complex for type I; Cmr or Csm RAMP complexes for type III) to facilitate the recognition and destruction of target nucleic acids (Brouns et al., *Science,* 321(5891): 960-4 (2008); and Hale et al., *Cell,* 139(5): 945-56 (2009)). In bacteria, the type I CRISPR DNA interference machinery is composed of an RNA-guided Cascade Complex for target site recognition and a Cas3 protein for target degradation. Unlike the widely used type II CRISPR-Cas9 systems, which generate a double strand DNA break at the local target site, the type I CRISPR machinery induces heterogenous deletions of very large DNA segments. This is especially useful for eliminating disease causing large genomic loci, such as parasitic sequence, non-coding RNA, or enhancers. Since the deletions introduced by Cascade/Cas3 vary in length, this system can also be used as a screening tool to scan the large mammalian genome for key regulatory elements (e.g., enhancers, insulators, or repressors).

A subtype of a type I CRISPR system from *T. fusca* (type I-E) has been used for genome editing in mammalian cells (see, e.g., International Patent Application Publication WO 2019/246555A1 and Dolan et al., *Mol Cell,* 74(5): 936-950.e5 (2019); doi: 10.1016/j.molcel.2019.03.014). However, the larger gene size of type I-E CRISPR loci (i.e., six Cas genes and 1 CRISPR array, for a total size of about 8.5 kb) makes delivery into mammalian cells and animals challenging; and the larger number of Cas proteins in the type I-E Cascade complex makes ribonucleotide (RNP) preparation tedious and inefficient.

Thus, there remains a need for more compact CRISPR-Cas systems and methods for inducing long-range deletions of target genomic regions.

SUMMARY

The disclosure provides a method of altering a target DNA sequence (e.g., a genomic DNA sequence). In some embodiments, the target DNA sequence is in a host cell. In some embodiments, the method comprises introducing into a host cell comprising a target DNA sequence: (a) a synthetic guide RNA sequence that is complementary to a target DNA sequence in a host cell (e.g., wherein the target genomic DNA sequence encodes at least one gene product); and (b) a combination of two or more *Neisseria lactamica* proteins selected from Cas3, Cas5, Cas8c, and Cas7. In some embodiments, the guide RNA sequence binds to the target DNA sequence, and the combination of two or more *N. lactamica* proteins induces cleavage of one or both strands in the target DNA sequence, thereby altering the target DNA sequence.

BRIEF DESCRIPTION OF THE DRAWING(S)

Figure 1B:
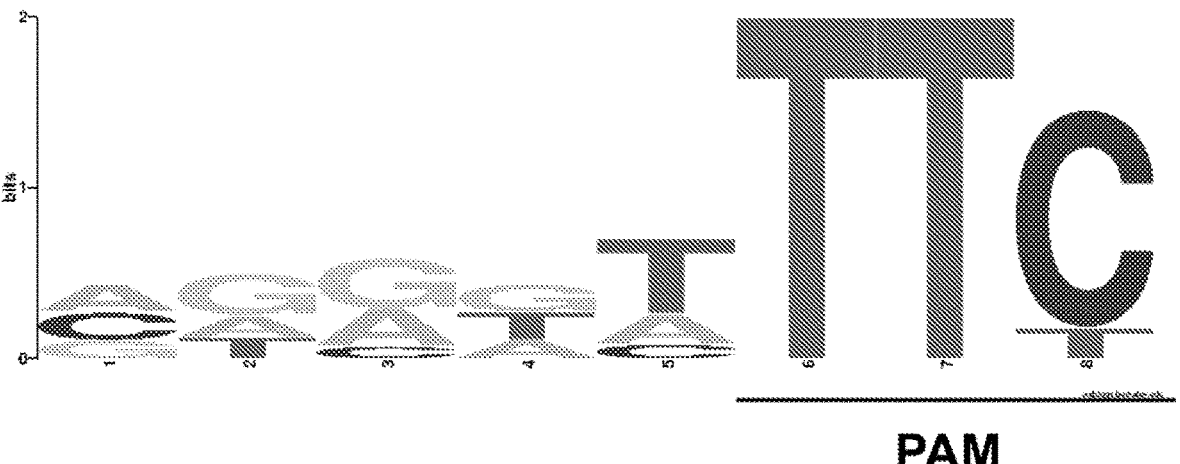

FIG. 1A is a schematic diagram illustrating the type I-C CRISPR-Cas locus from *Neisseria lactamica* (Nla) strain ATCC 23970. FIG. 1B is schematic diagram illustrating the prediction of the 5' protospacer-adjacent motif (PAM) required for Nla type I-C CRISPR interference.

Figure 2A:
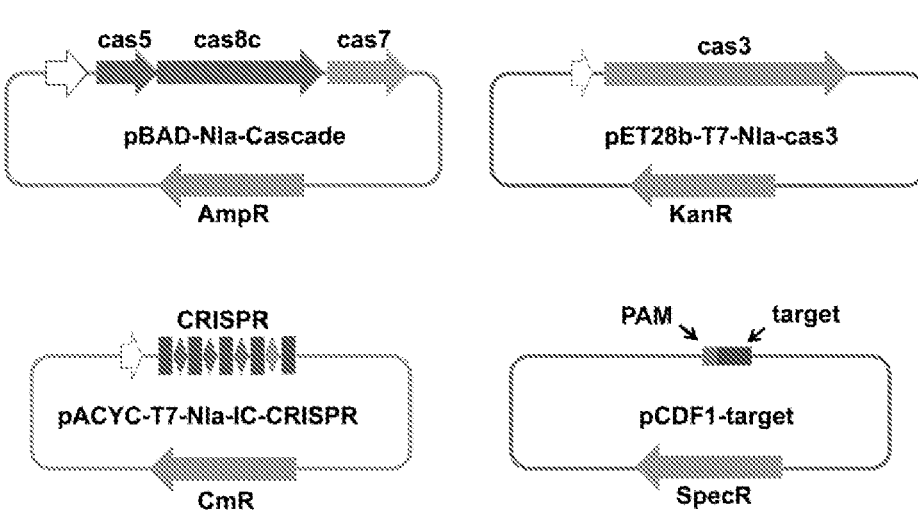
Figure 2B:
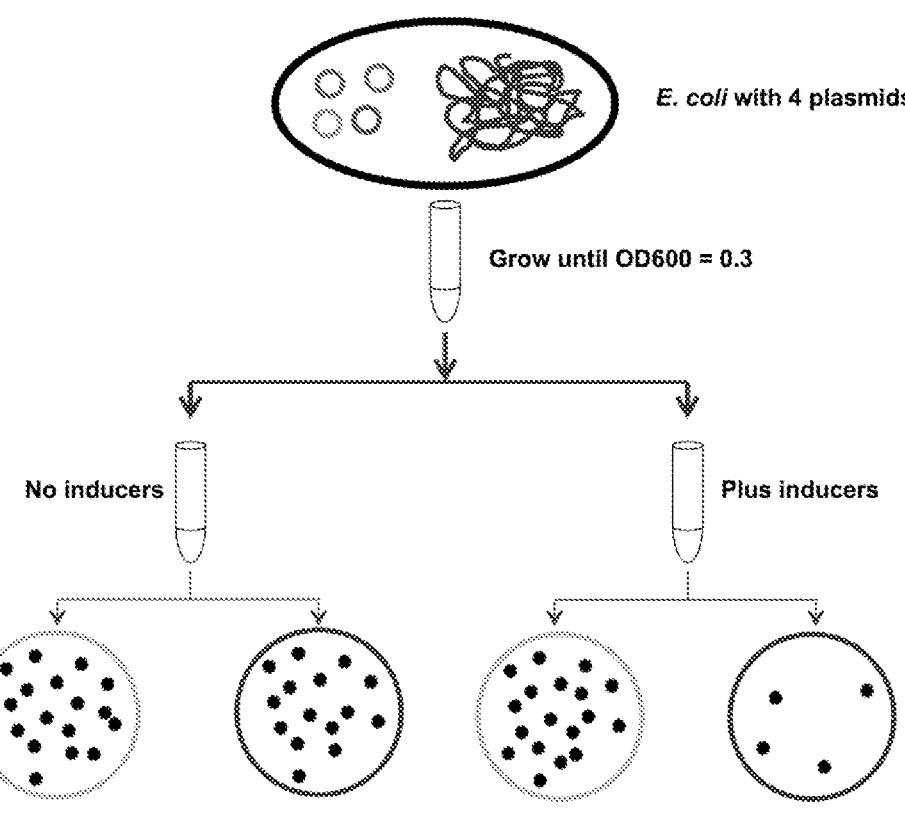
Figures 2C, 2D:
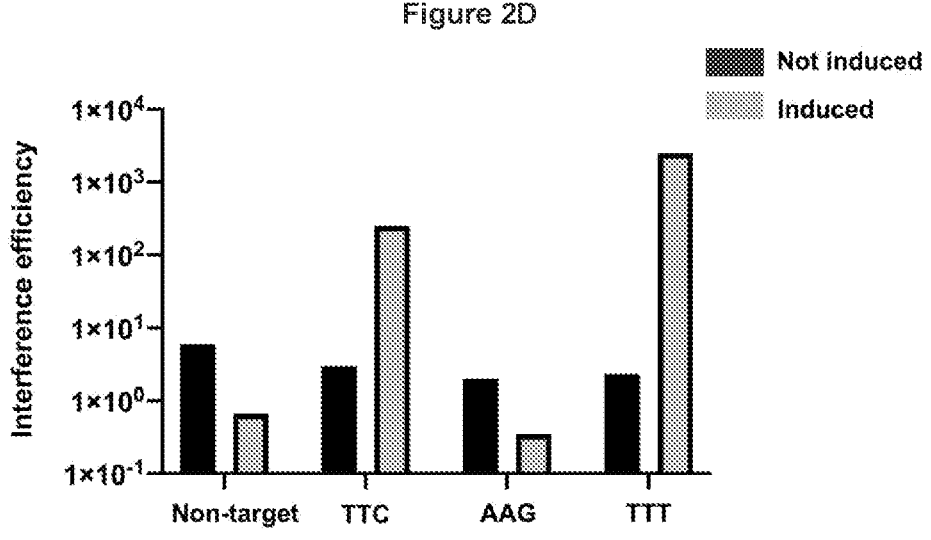
Figure 2E:
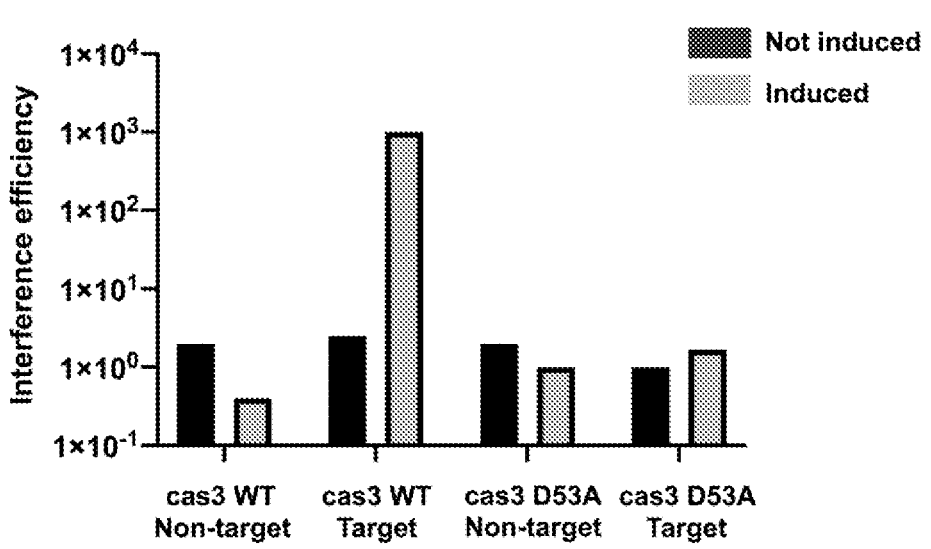

FIG. 2A is a schematic diagram showing the plasmids used for the *E. coli* plasmid interference assay described in the Examples. The Nla cas5-cas8c-cas7 operon was under control of an arabinose inducible promoter. Nla cas3 expression was driven by a T7 promoter. The CRISPR array was also under control of a T7 promoter. FIG. 2B is a schematic diagram illustrating the plasmid interference assay. When a CRISPR-complementary target with a 5'-TTC-3' or 5'-TTT-3' PAM is present on the target plasmid, induction of Nla I-C CRISPR-cas expression leads to destruction of the target plasmid, which in turn results in low numbers of colonies on LB plates (black) that select for the co-presence of all four plasmids/antibiotics. The plates (grey) that select for plasmids other than the target plasmid served as a control. The ratio of colony forming units between the two plates (non-target selection vs target selection) represents the efficiency of CRISPR interference. FIG. 2C is a graph showing that the Nla type I-C system enables a robust CRISPR interference phenotype. FIG. 2D is a graph showing that DNA interference by type I-C CRISPR-cas is dependent on a functional PAM. FIG. 2E is a graph showing that DNA interference requires the nuclease activity of Cas3.

Figure 3A:
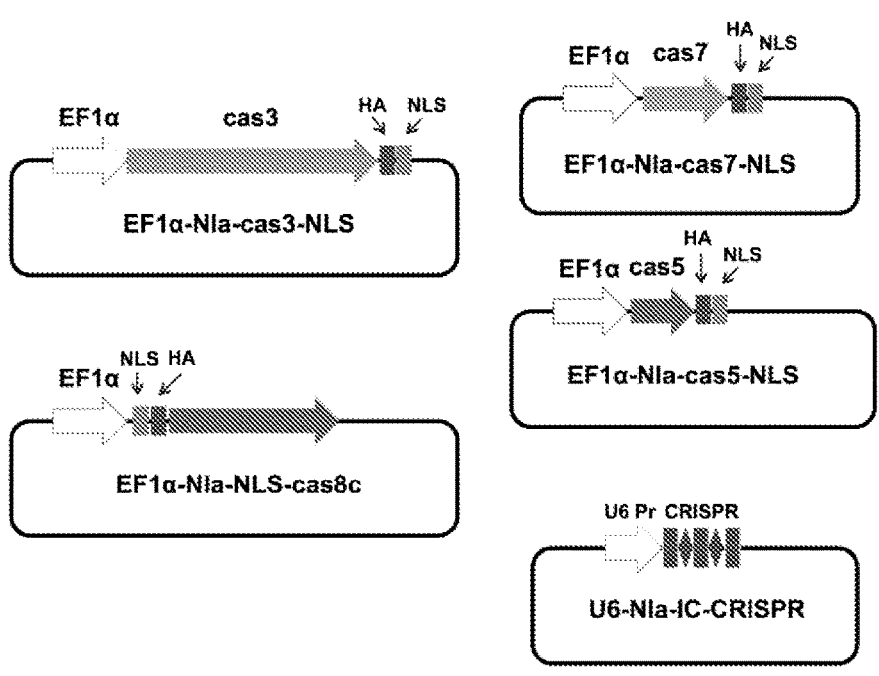
Figure 3B:
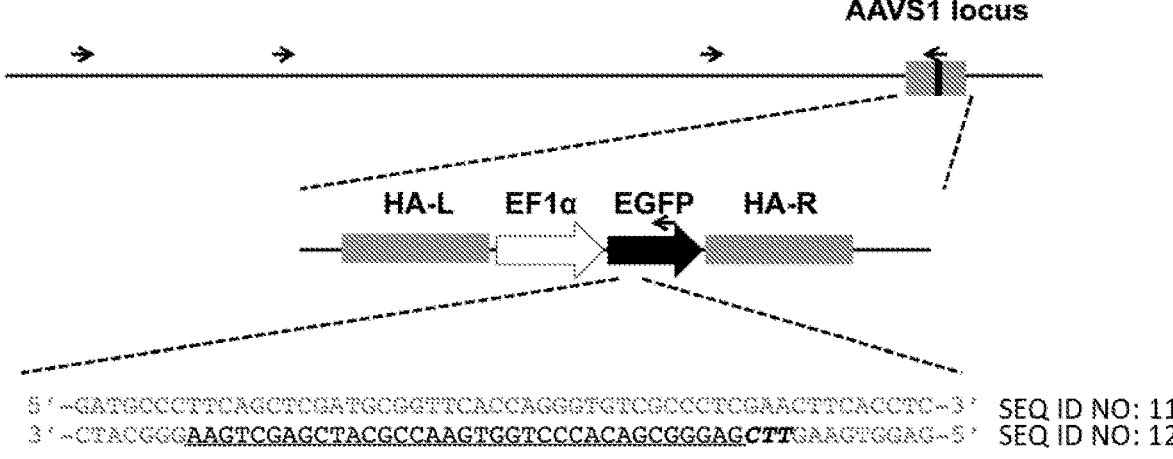
Figure 3F:
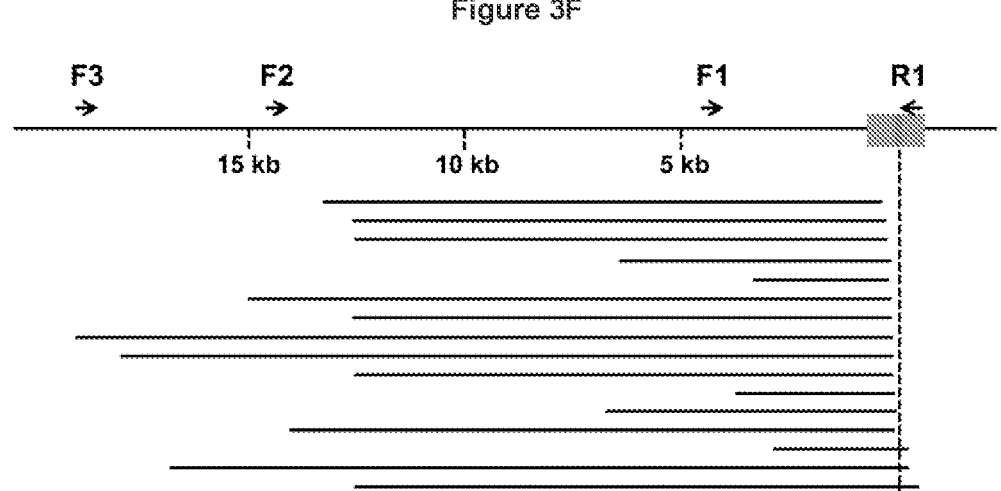

FIG. 3A is a schematic diagram illustrating the plasmid design for expressing Nla type I-C CRISPR-cas components in human cells. FIG. 3B is a schematic diagram of the targeted genomic locus in the HAP1-AAVS1-EGFP reporter cell line. The spacer-commentary target sequence within EGFP is underlined and its flanking 5'-TTC PAM is italicized. Successful targeting by the Nla type I-C CRISPR system should lead to GFP negative cells. FIGS. 3C and 3D are images of flow cytometry analyses of the HAP1-AAVS1-EGFP cells before (FIG. 3C) and after (FIG. 3D) editing by Nla type I-C CRISPR-Cas. FIG. 3E is an image of PCR analysis of DNA deletions induced by Nla type I-C CRISPR-Cas. FIG. 3F is a schematic diagram showing the PCR primer pairs used and depicts their annealing sites. FIG. 3F also reveals the boundaries of the unique deletion events on the genome induced by Nla type I-C CRISPR-Cas. Each solid black line represents a deleted genomic region for one event. The dashed black line marks the targeted GFP sequence.

Figure 4A:
Figure 4A:
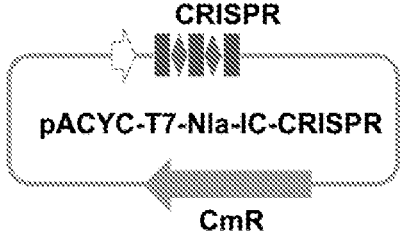
Figure 4B:
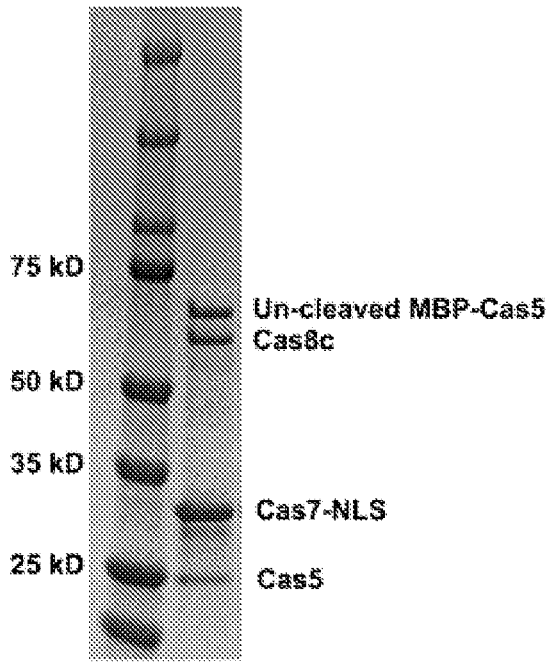
Figures 4C, 4D, 4E:
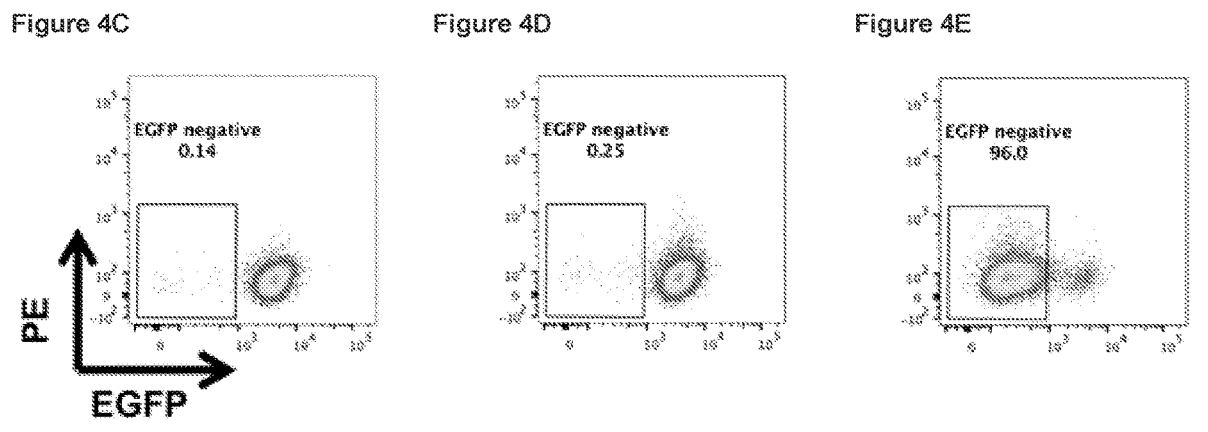

FIG. 4A is a schematic diagram showing the plasmids used to express and purify NLS-Cascade from *E. coli* BL21 (DE3) cells. The CRISPR array contains three repeats and two identical spacers targeting the EGFP site. FIG. 4B is an image of Coomassie-stained, SDS-PAGE analysis of the purified Cascade complex. FIGS. 4C-4E are images of flow cytometry analyses of HAP1-AAVS1-EGFP reporter cells that were either unedited (FIG. 4C), or electroporated with EGFP-targeting Cascade RNP without (FIG. 4D) or with (FIG. 4E) mRNA encoding cas3.

Figure 5A:
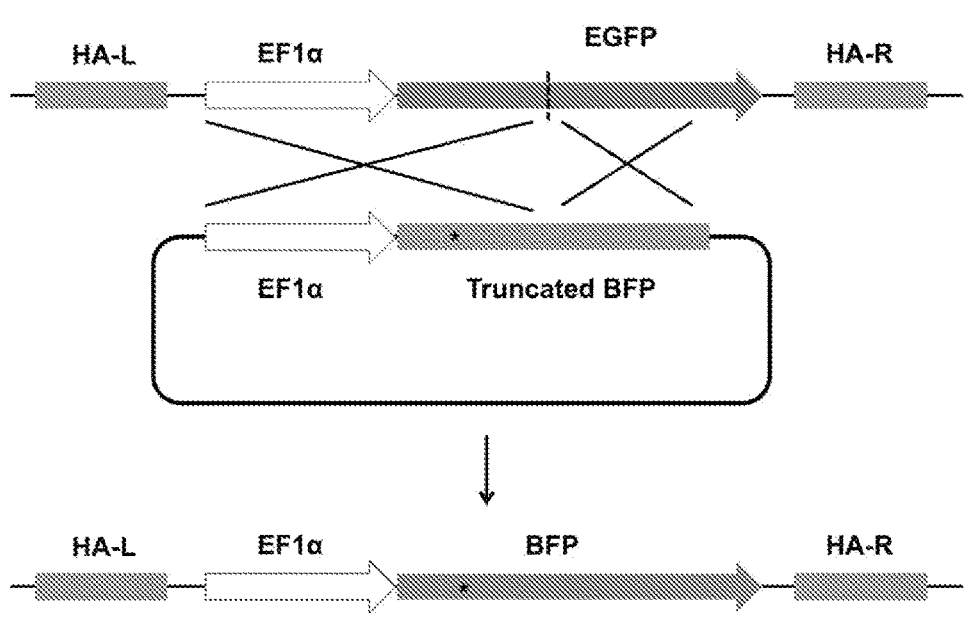
Figures 5B, 5C, 5D:
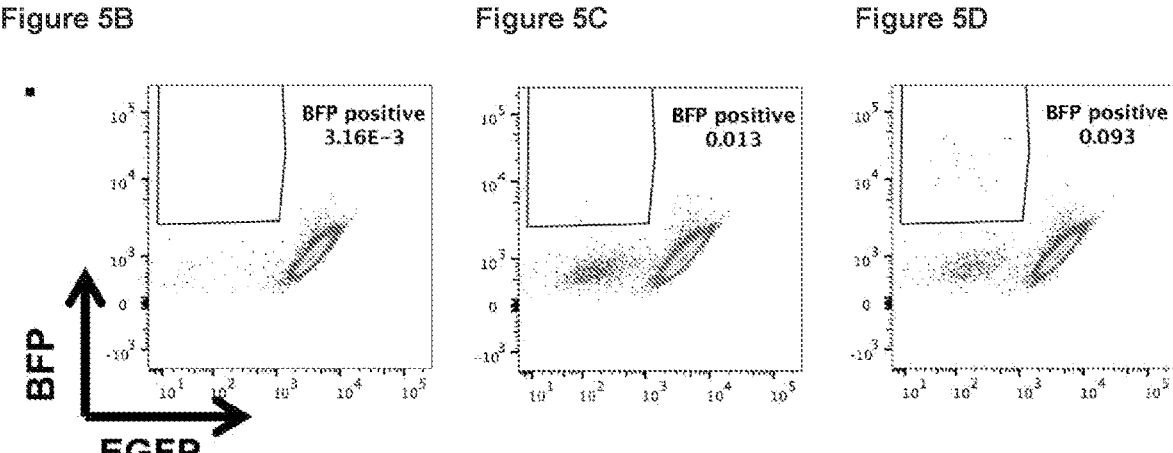

FIG. 5A includes schematic diagrams of the targeted AAVS1-EF1α-EGFP locus (top panel) and the HDR donor plasmid (middle panel). The HDR donor DNA template contains a truncated, non-functional BFP fragment and an EF1a promoter. The star * indicates the 2 nt sequence difference between the ORFs of EGFP and BFP. Upon successful HDR, the 2 nt change converts AAVS1-EF1α-EGFP to AAVS1-EF1α-BFP (bottom panel). Black dotted line, EGFP target site recognized by Nla I-C CRISPR-Cas. FIGS. 5B-5D are images of flow cytometry analyses of the HAP1-AAVS1-EGFP reporter cells that were unedited (FIG. 5B) or transfected with CRISPR-Cas plasmids without (FIG. 5C) or with (FIG. 5D) the HDR donor template.

Figure 6C:
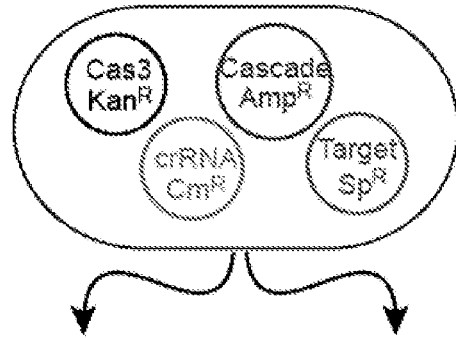
Figure 6C:
Figure 6C:
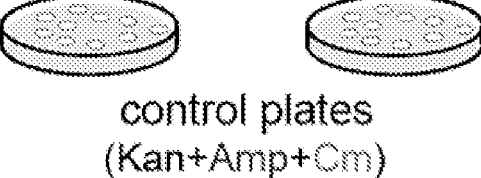
Figure 6D:
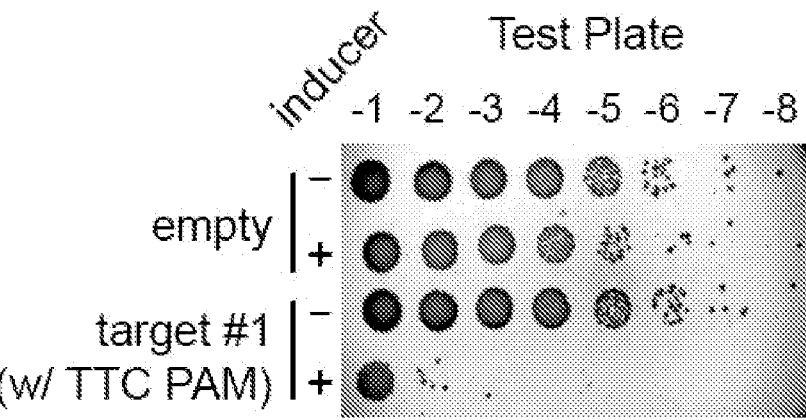
Figure 6E:
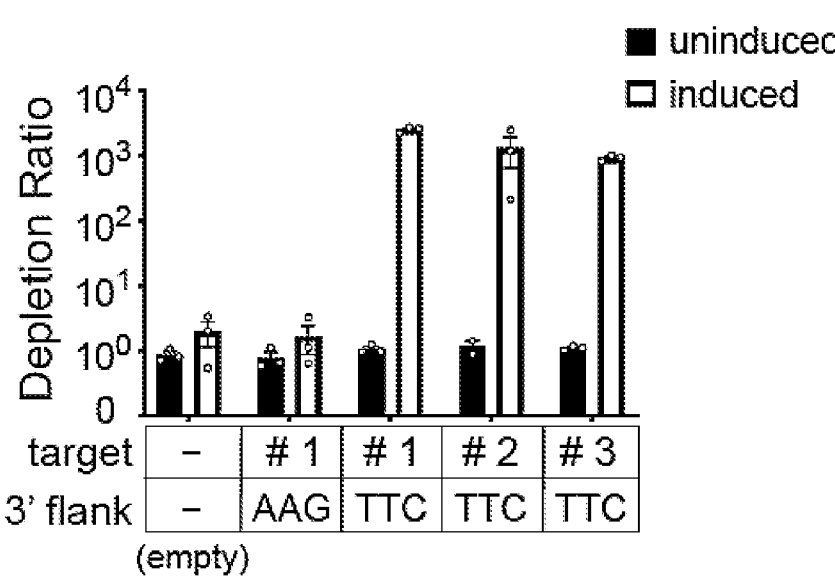
Figure 6F:
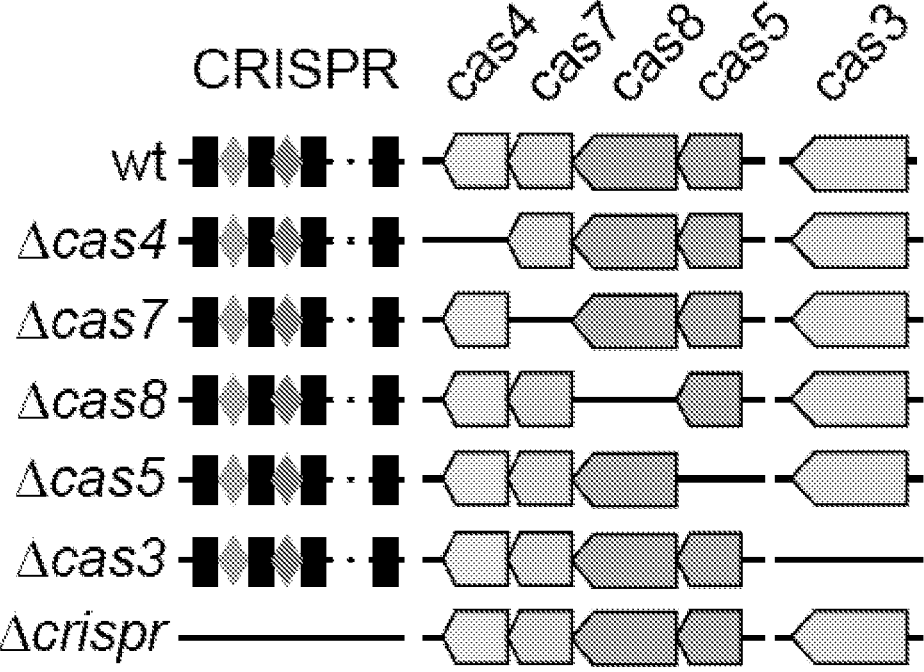
Figure 6G:
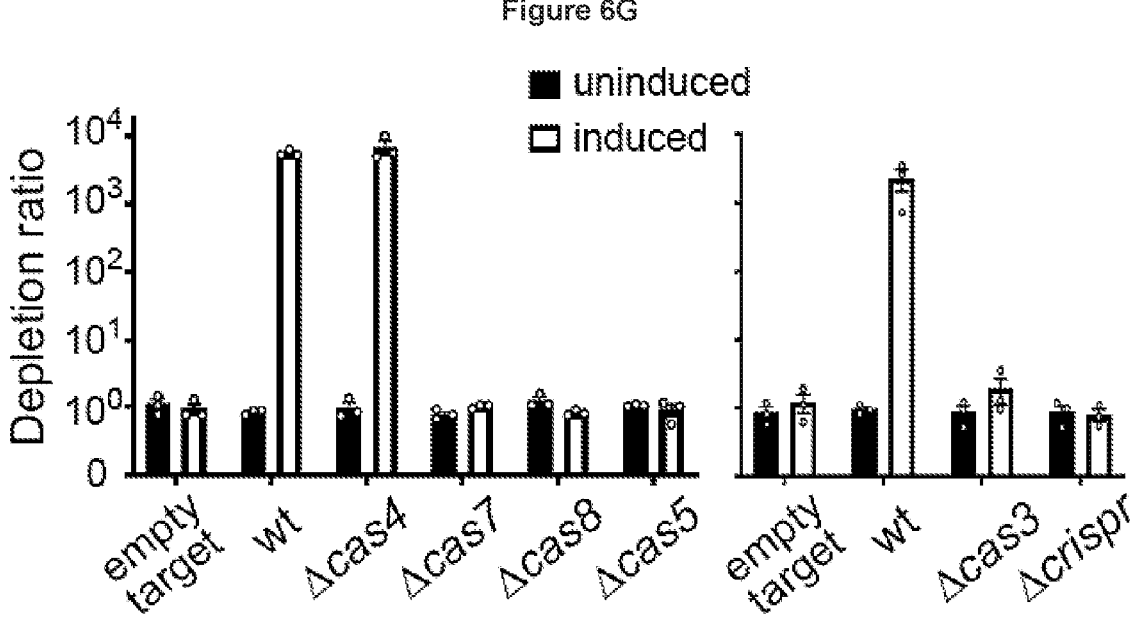

FIG. 6A is a schematic of the miniature type I-C CRISPR-Cas locus from *N. lactamica*, with cas1, cast and cas4, cas7, cas8, cas5, and cas3. Rectangles, CRISPR repeats; diamonds, CRISPR spacers. Cas genes are drawn to scale, while the CRISPR array is enlarged for clarity. FIG. 6B is an informatic prediction defining a 5'-TTC PAM. Potential natural targets for native spacers of *N. lactamica* ATCC 23970 were defined using CRISPRTarget, with up to 1 nt mismatch in spacer-target complementarity allowed and denoted in bold. The target sequences (SEQ ID NOs: 31-53) and their 10-nt flanks on both 5' (SEQ ID NOs: 13-30) and 3' (SEQ ID NOs: 54-77) sides were aligned using Weblogo, and the resulting sequence logos were shown at the top. FIG. 6C is a schematic overview of the plasmid interference assay in *E. coli*. BL21-AI derivative strains harboring four plasmids encoding crispr, cas3, cascade genes, and a target-PAM sequence were cultured with or without induction of crispr-cas expression, serial diluted, and plated on LB plates with triple or quadruple antibiotics to track cell survival. Reduced colony count on quadruple antibiotics plate for the induced culture indicates a CRISPR interference phenotype. FIG. 6D is a representative image of an interference assay where isogenic *E. coli* strains were titered on a quadruple antibiotics plate in 10-fold serial dilutions. Under induced conditions, a matching target with 5'-TTC PAM led to drastic reduction in colony counts compared to the empty target control, indicative of robust CRISPR interference in vivo. FIG. 6E is a graph of the induction of crispr-cas expression which led to robust interference for three different targets flanked by a 5' TTC PAM, but not for the controls containing either no target or a 5'AAG-flanked target. Depletion ratio was calculated as the colony-forming units (CFUs) from triple antibiotic control plate divided by CFUs from quadruple antibiotic test plate. Data are displayed as log scale plots of the mean depletion ratio±SEM, n=3. FIG. 6F is a schematic of the crispr-cas loci in isogenic mutant strains used in FIG. 6G. FIG. 6G is a graph of CRISPR Interference mediated by the Nla type I-C system utilizing the cas7, cas8, cas5, cas3 and crispr genes but not cas4. Data are quantified and shown as in FIGS. 6D and 6E.

Figure 7A:
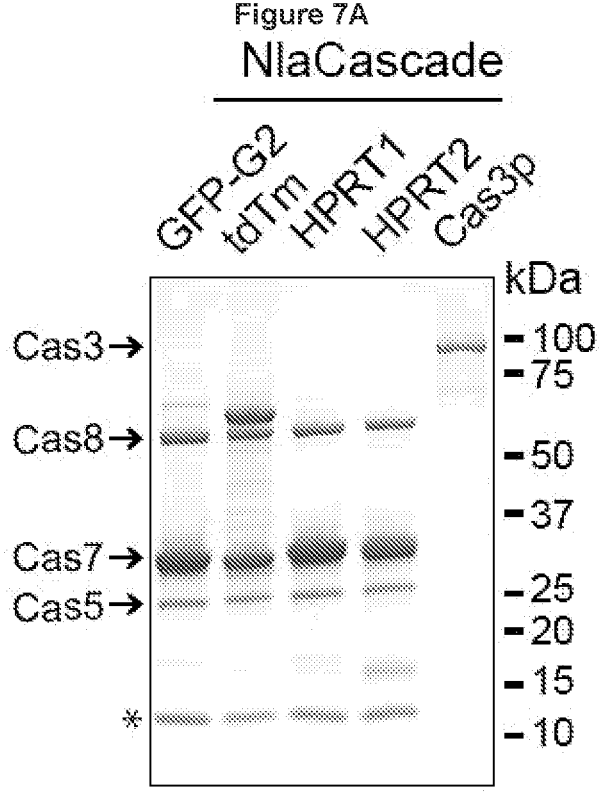
Figures 7B, 7C:
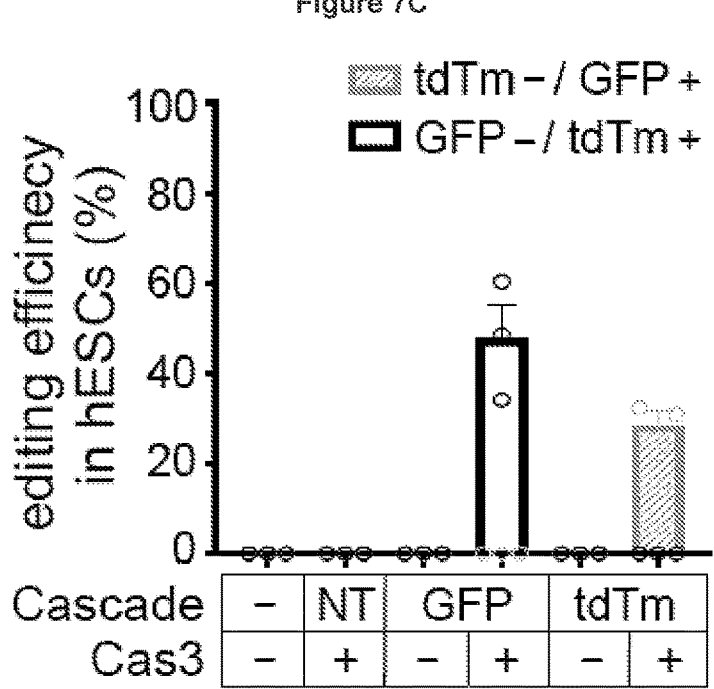
Figure 7D:
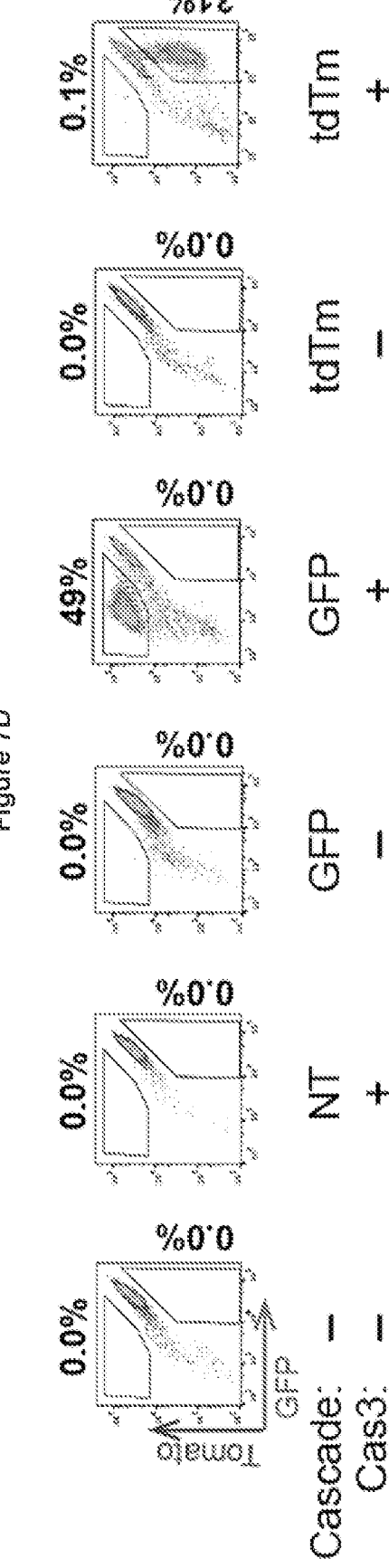
Figures 7E, 7F:
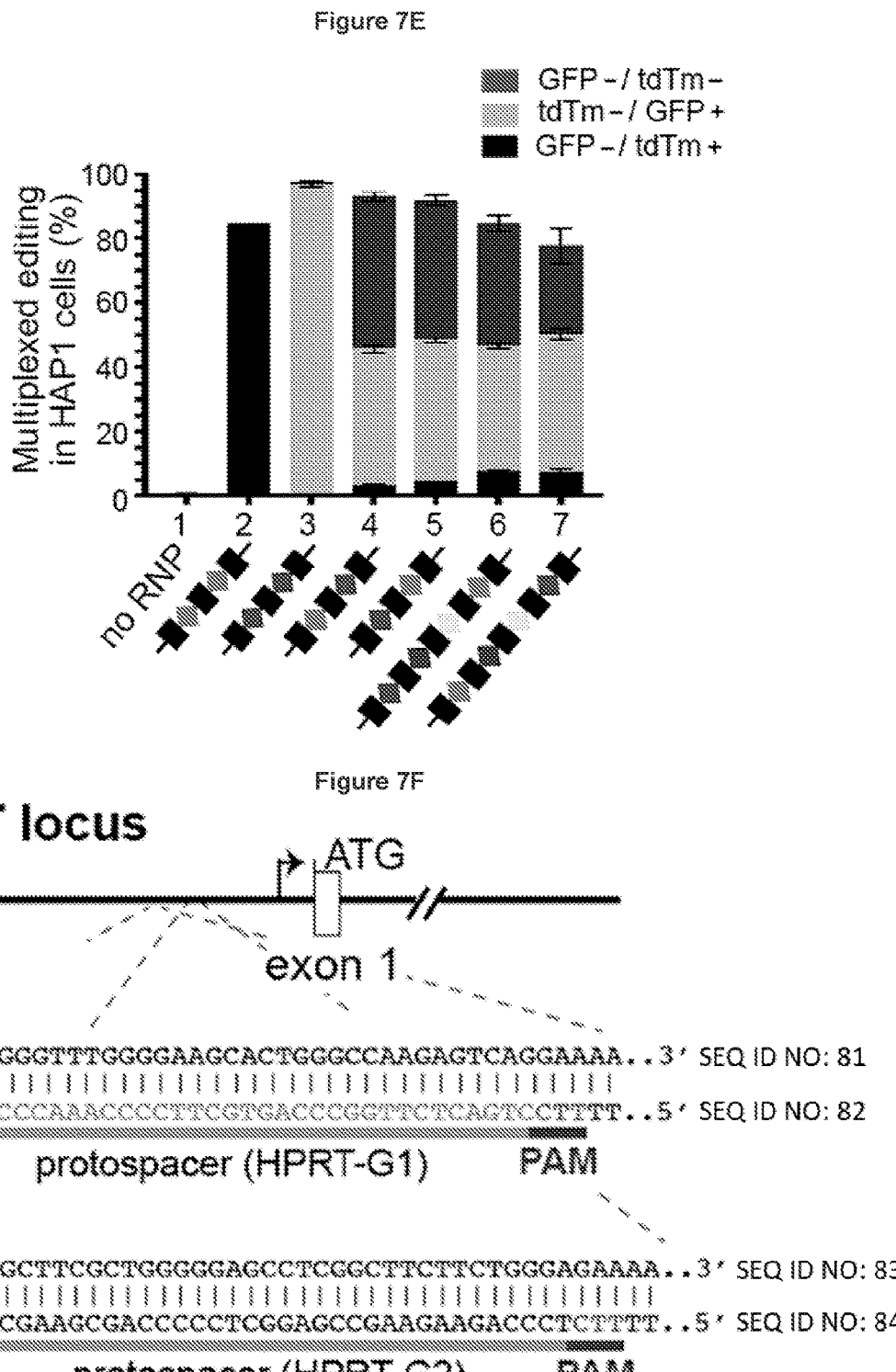
Figures 7G, 7H:
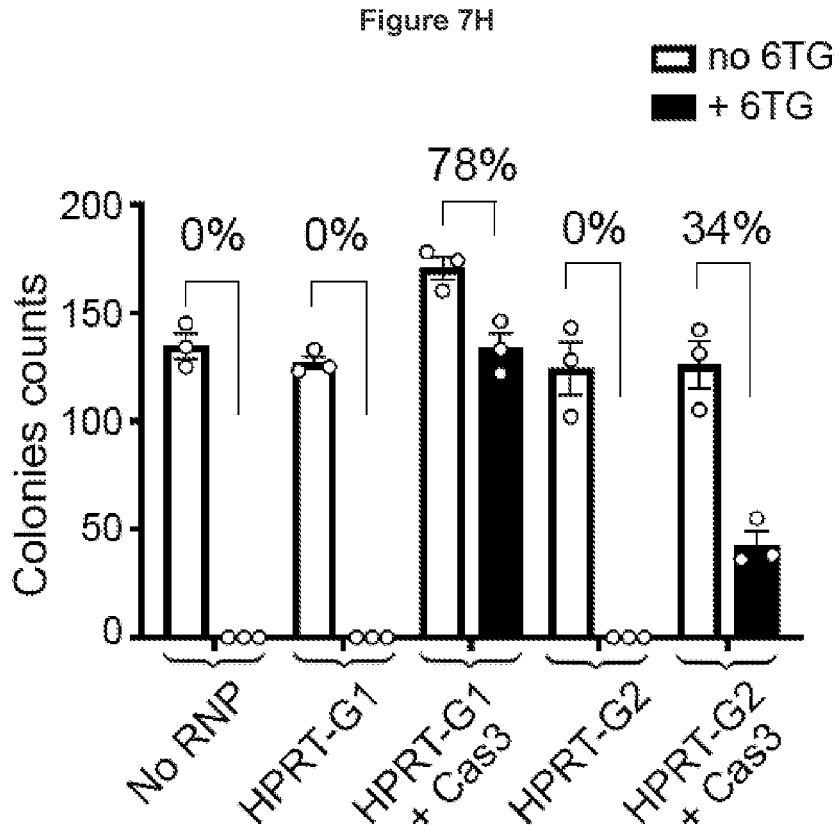

FIG. 7A is an SDS-PAGE of purified Nla Cas3 protein and Cascade RNP samples targeting different genes (GFP-G2, tdTomato (tdTm), and HPRT1&2). Note: Cascade tdTm was purified using a slightly different strategy, and therefore contains an extra band of ~68 KDa corresponding to His-MBP-Cas5. FIG. 7B is a schematic of the hESC dual-reporter cells used in FIGS. 7C and 7D, with protospacers for the EGFP− or tdTm− targeting Cascade indicated in with corresponding PAMs. FIG. 7C is a graph of Cascade RNP targeting either EGFP, tdTm or a control locus (Non-targeting (NT), e.g., HPRT1) electroporated into hESCs with or without purified Cas3. The gene editing efficiency was shown as the percentage of EGFP−/tdTm+ or tdTm−/EGFP+ cells in the total population. Data are shown as mean±SEM, n=3. FIG. 7D is representative flow cytometry plots from experiments in FIG. 7C, with percentages of EGFP−/tdTm+ or EGPF+/tdTm− cells shown on the top or to the right, respectively. FIG. 7E is a graph of robust multiplexed RNP editing in HAP1 dual reporter cells. Cascade RNP purified using each multi-spacer CRISPR array depicted at the bottom was electroporated into HAP1 reporter cells together with Cas3. The reporter gene editing efficiencies were shown as the percentage of GFP−/tdTm+, tdTm−/GFP+, and GFP−/tdTm− cells in the total population. Data are shown as mean±SEM, n=3. The spacers represent Nla guides targeting EGFP, tdTm, HPRT, and CCR5 genes, respectively. FIG. 7F is a schematic of the HPRT1 locus in HAP1 cells, with protospacers for the two HPRT-targeting Cascades shown with corresponding PAMs. FIG. 7G is a chart of the HPRT1 editing efficiency measured by single clone 6-TG survival assay. The survival rate is the ratio between the average colony counts of 6-TG+ vs. 6-TG− conditions. FIG. 7H is a bar graph plotting the colony counts from FIG. 7G. Data are shown as mean±SEM, n=3.

Figures 8D, 8E:
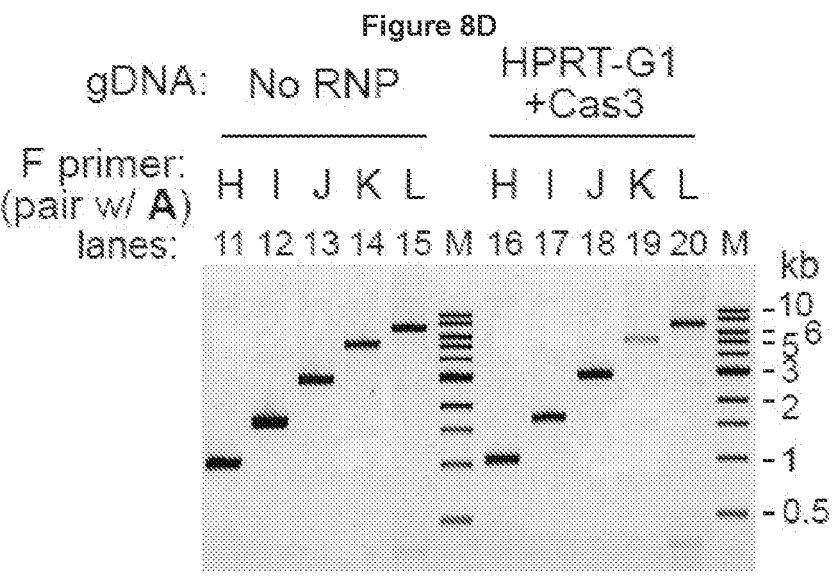

FIG. 8A is a schematic of the HPRT1 locus and annealing sites for PCR primers used in FIGS. 8B, 8D, and 8E. All positions indicated are relative to HPRT1 translation start site (+1). The dashed line marks the recognition site (3rd nt of the TTC PAM) for guide HPRT1-G1. Hatched arrow, presumed direction of NlaCas3 translocation. FIGS. 8B, 8D, and 8E show the characterization of genomic lesions by long-range PCRs, using primers amplifying regions downstream (FIG. 8B) or upstream (FIG. 8D) of the CRISPR-targeted site, or regions spanning both directions (FIG. 8E). A spectrum of large, unidirectional deletions was detected in the PAM-proximal genomic region, from cells treated with Cas3 and Cascade HPRT-G1, but not the untreated control (no RNP) cells. PCR primers used are listed and their annealing sites depicted in FIG. 8A. Smaller-than-full-length amplicons indicate large genomic deletions. M, DNA size markers. FIG. 8C is a schematic of the deletion locations at the HPRT1 locus, revealed by TOPO cloning of pooled tiling PCRs from lanes 6-10 in FIG. 8B and Sanger sequencing. Lines, deleted genomic regions.

Figure 9A:
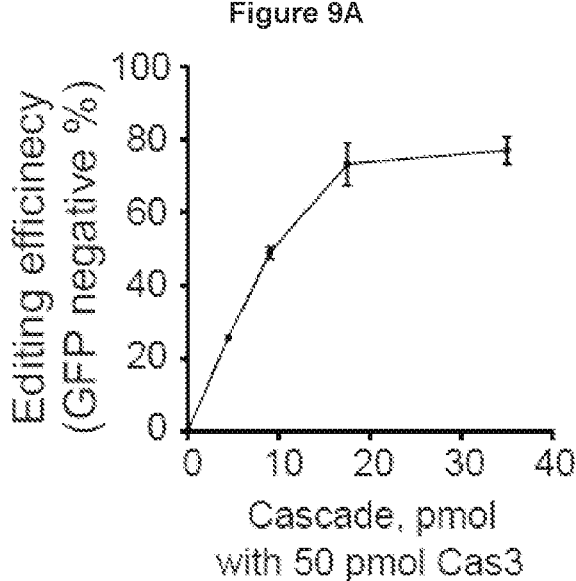
Figure 9B:
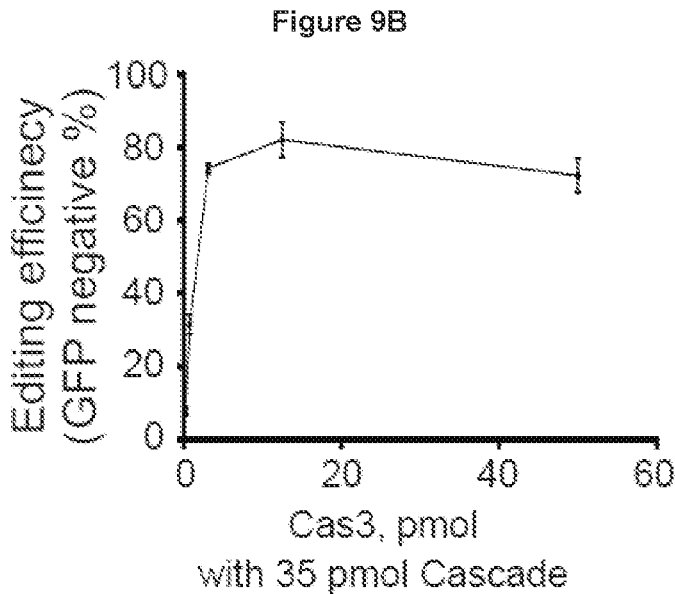

FIG. 9A is a graph of RNP editing experiments in HAP1 reporter cells with 50 pmol NlaCas3 and increasing amount of GFP-targeting NlaCascade. Cascade amount electroporated was titrated from 4.5 pmol to 35 pmol. FIG. 9B is a graph of RNP editing in HAP1 reporter cells with 35 pmol GFP-targeting NlaCascade and increasing amount of Cas3. NlaCas3 protein electroporated was 0, 0.2, 0.8, 3.1, 12.5, and 50 pmol. FIGS. 9C and 9D are representative flow cytometry plots from experiments in (FIG. 9C) and (FIG. 9D), respectively, with percentages of EGFP− in the total population shown on the top.

Figure 10A:
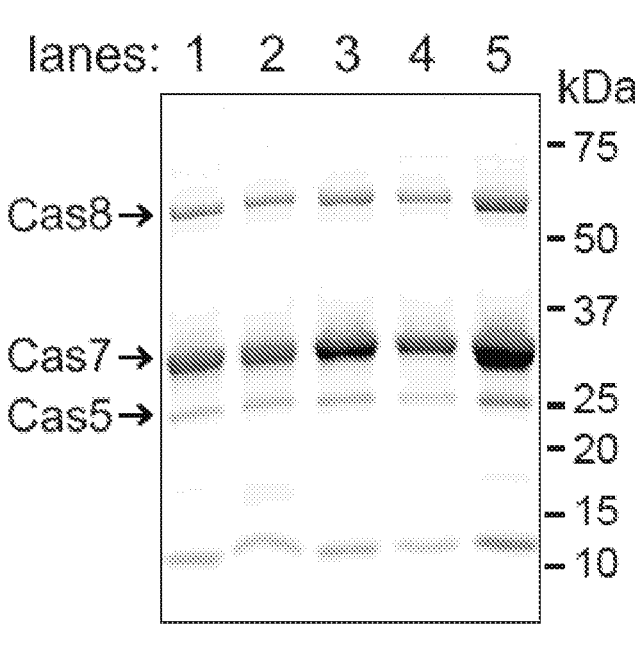
Figure 10A:
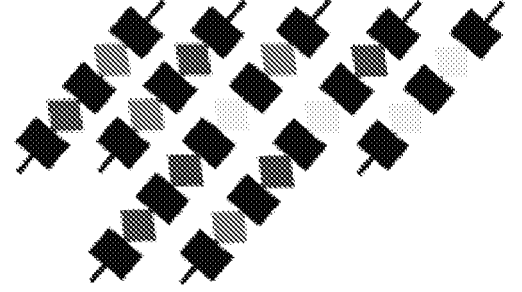
Figure 10B:
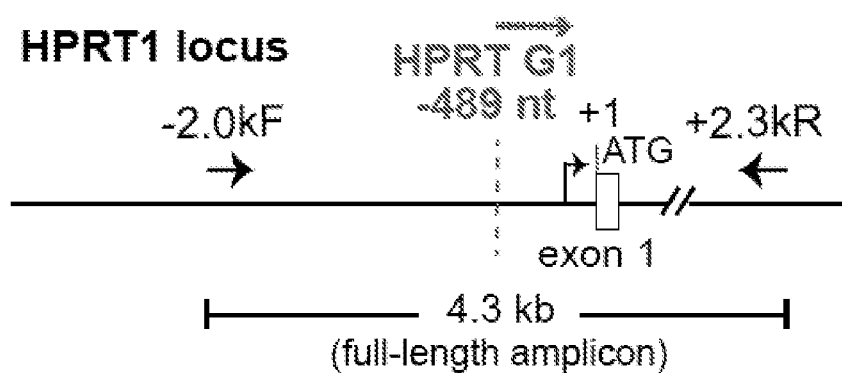
Figure 10B:
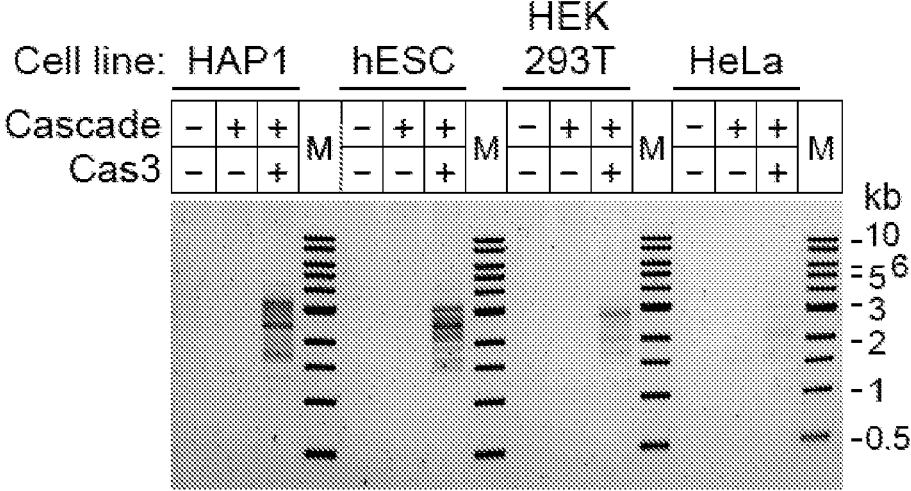
Figure 10C:
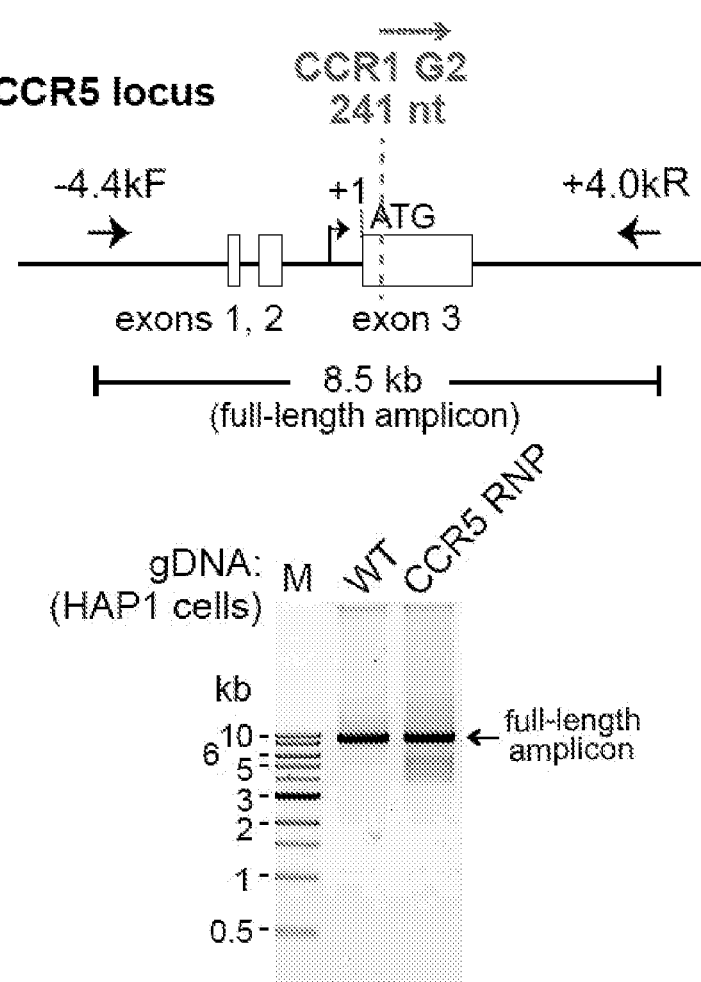

FIG. 10A is an SDS-PAGE of purified NlaCascade samples used for multiplexed editing in FIG. 7E and for CCR5 targeting. FIG. 10B, Top, is a schematic of HPRT1 locus. Big arrows, annealing sites for two primers used in genomic PCR. All positions indicated are relative to HPRT1 translation start site (+1). The dashed line marks the recognition site (3rd nt of the TTC PAM) for guide HPRT1-G1. Hatched arrow, presumed direction of NlaCas3 translocation. FIG. 10B, Bottom, shows long-range PCR using genomic DNA extracted from various human cell types (HAP1, hESCs, HEK293T, and Hela) edited with Cas3 and HPRT-targeting Cascade RNP. Smaller-than-full-length amplicons indicate large genomic deletions caused by HPRT1 targeting. M, DNA size markers. FIG. 10C, Top, is a schematic of CCR5 locus. Big arrows, annealing sites for two primers used in genomic PCR. All positions indicated are relative to CCR5 translation start site (+1). The dashed line marks the recognition site (3rd nt of the TTC PAM) for guide CCR5-G2. Hatched arrow, presumed direction of NlaCas3 translocation. FIG. 10C, Bottom, is long-range PCR as described in (FIG. 10A), using genomic DNA extracted from HAP1 cells edited with Cas3 and CCR5-targeting Cascade RNP. Smaller-than-full-length amplicons indicate large genomic deletions resulted from successful CCR5 targeting.

Figure 11A:
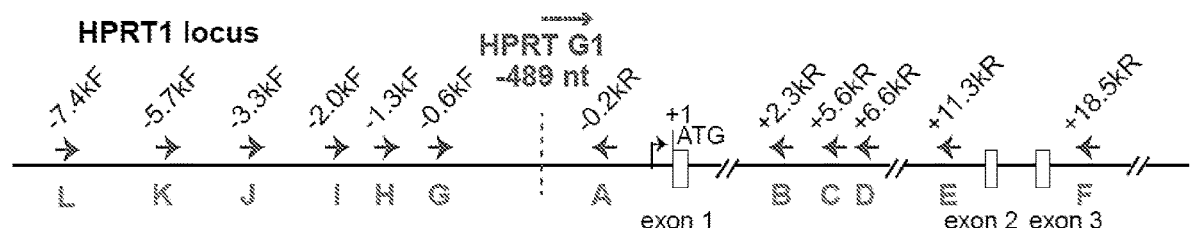
Figure 11B:
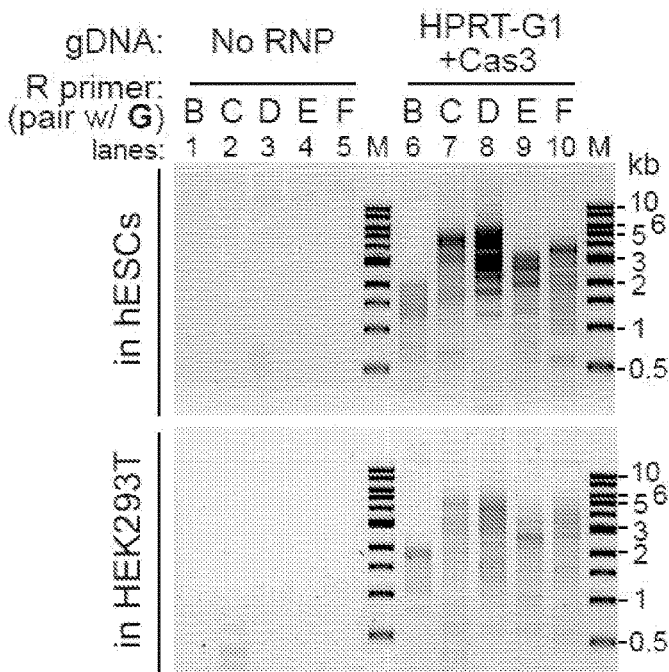
Figures 11C, 11D:
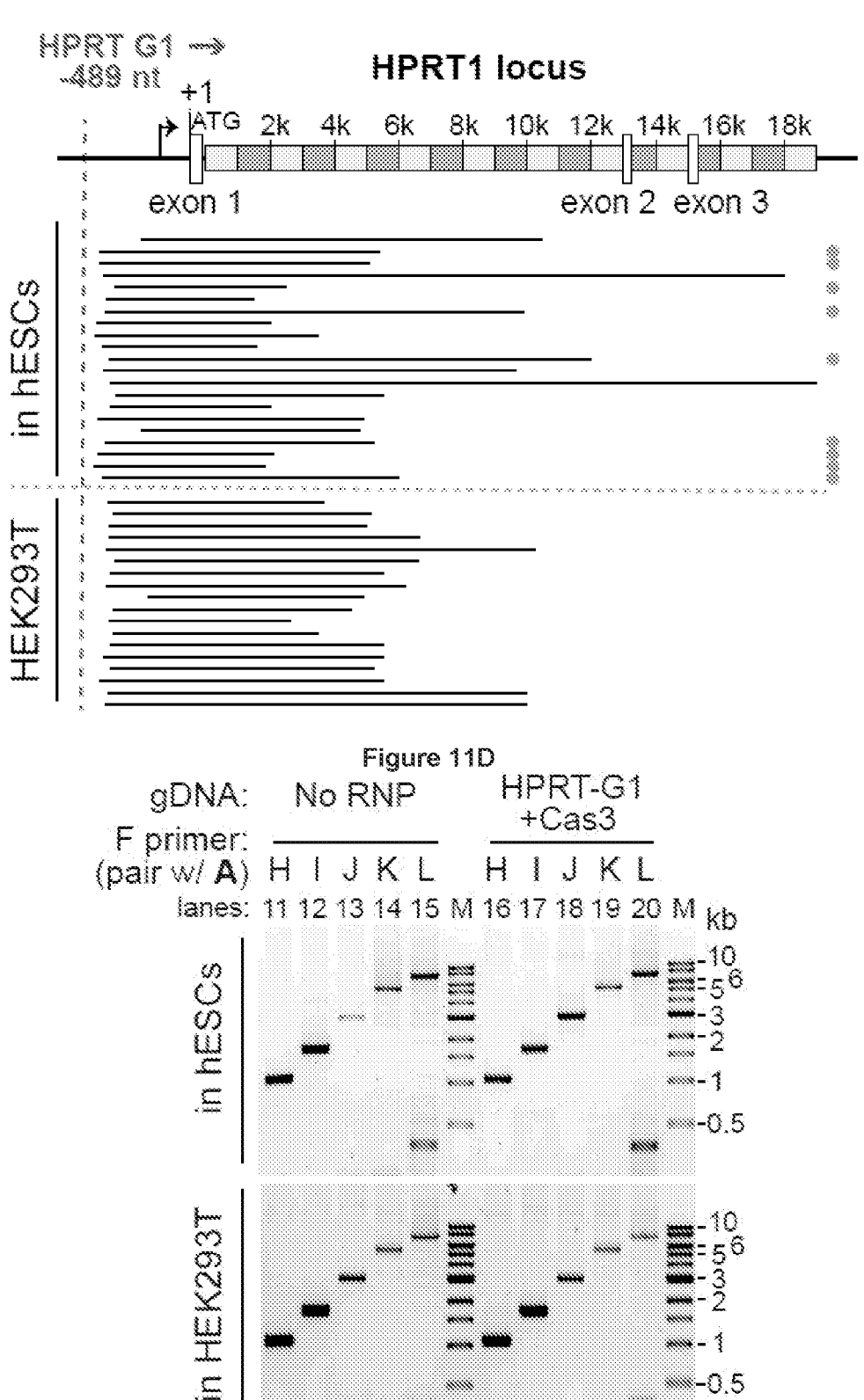
Figure 11E:
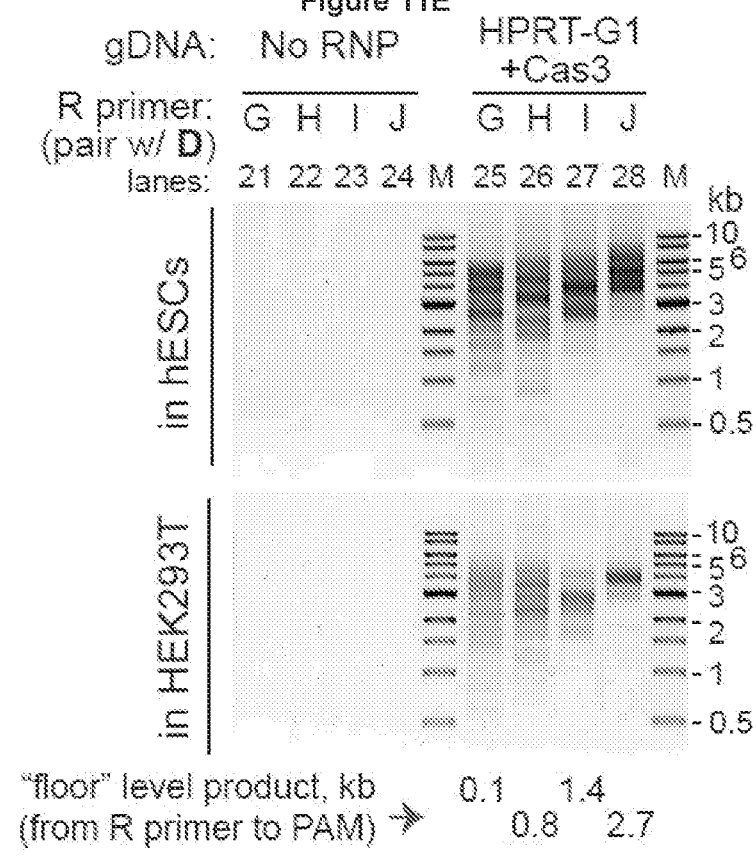

FIG. 11A is a schematic of HPRT1 locus and annealing sites of PCR primers used in FIGS. 11B, 11D, and 11E. All positions indicated are relative to HPRT1 translation start site (+1). The dashed line marks the recognition site (3rd nt of the TTC PAM) for guide HPRT1-G1. Hatched arrow, presumed direction of NlaCas3 translocation. FIGS. 11B, 11D, and 11E show genomic lesion analysis via long-range PCRs, using primers amplifying regions downstream (FIG. 11B) or upstream (FIG. 11D) of the CRISPR-targeted HPRT site, or regions spanning both directions (FIG. 11E). The genomic DNA samples used as PCR template were extracted from hESCs and HEK293T cells. A spectrum of large, unidirectional deletions was detected in the PAM-proximal genomic region, from cells treated with Cas3 and Cascade HPRT-G1, but not the untreated control (no RNP) cells. Smaller-than-expected-full-length amplicons indicate large DNA deletions. The lack of full-length PCR product from the un-edited control is likely due to a GC-rich region in exon 1 (~400 bp downstream of the target site) that prevents PCR amplification. Smaller-than-full-length amplicons indicate large genomic deletions. M, DNA size markers. FIG. 11C is a schematic of HPRT1 deletion locations, revealed by TOPO cloning of pooled tiling PCRs from lanes 6-10 in FIG. 11B and Sanger sequencing of randomly selected individual clones. Lines, deleted genomic regions.

Figures 12A, 12B:
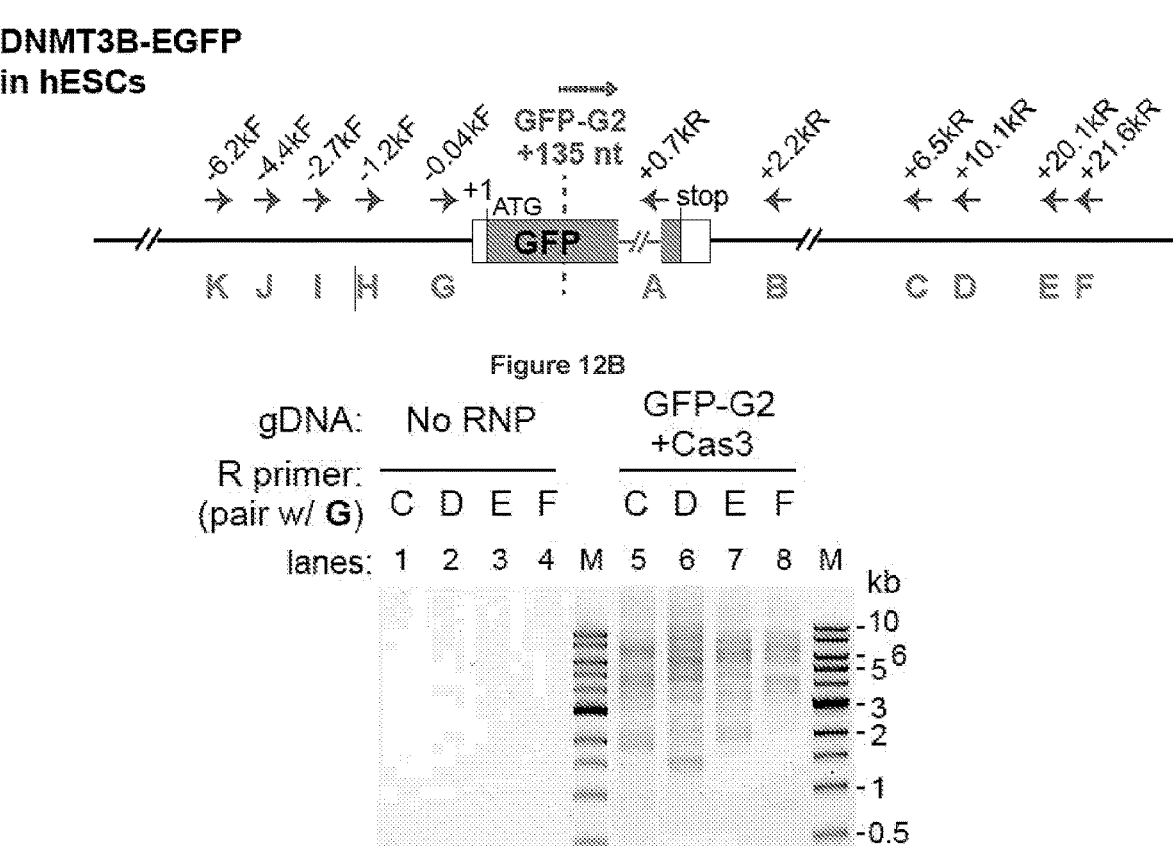
Figure 12C:
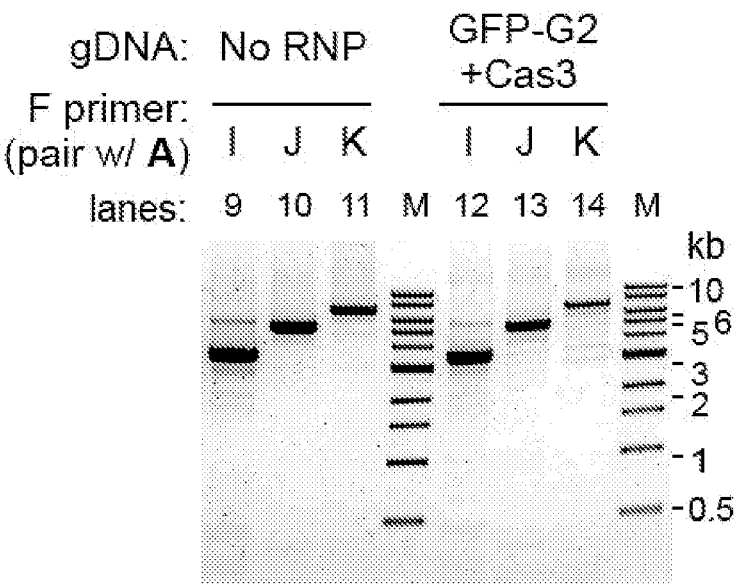
Figure 12D:
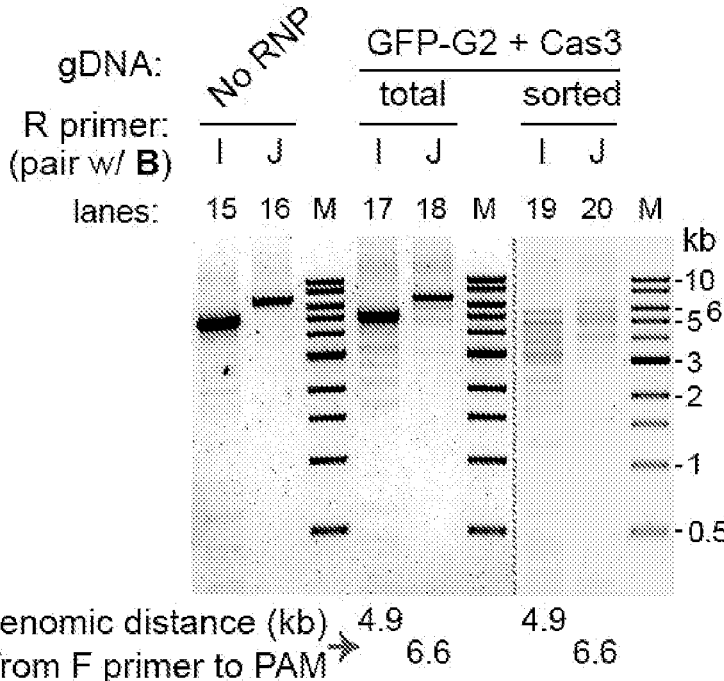
Figure 12E:
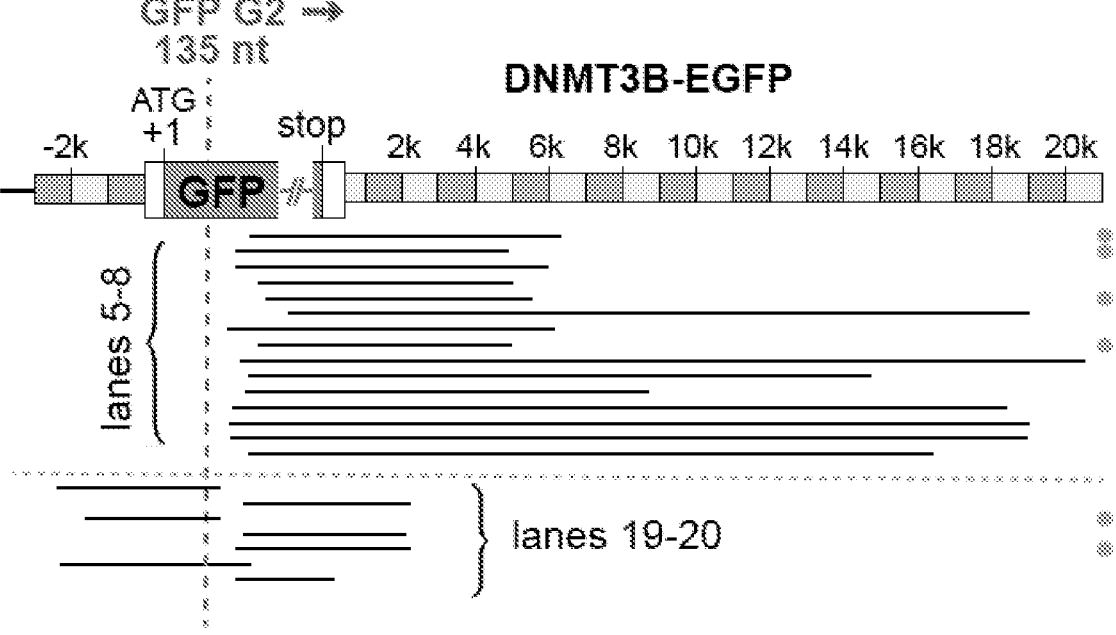

FIG. 12A is a schematic of DNMT3b-EGFP locus in hESC reporter cell line. Annealing sites of PCR primers used in FIGS. 12B-12E are indicated. All positions indicated are relative to EGFP translation start site (+1). The dashed line marks the recognition site (3rd nt of the TTC PAM) for guide EGFP-G2. Hatched arrow, presumed direction of NlaCas3 translocation. FIGS. 12B-12D show genomic lesion analysis via long-range PCRs, using primers amplifying regions downstream (FIG. 12B) or upstream (FIG. 12C) of the CRISPR-targeted GFP site, or regions spanning both directions (FIG. 12D). Genomic DNA used as PCR template was extracted from a hESC reporter line bearing EGFP and tdTm at the endogenous DNMT3b locus. A spectrum of large, unidirectional deletions was detected in the PAM-proximal region, from cells edited with Cas3 and Cascade GFP-G2, but not "no RNP" control cells. Smaller-than-expected-full-length amplicons indicate large DNA deletions. M, DNA size markers. Discontinuous lanes from the same gel are separated by the dashed line. FIG. 12E is a schematic of deletion locations revealed by TOPO cloning of pooled tiling PCRs from lanes 5-8 from FIG. 12B and 19-20 from FIG. 12D. Randomly selected individual clones are Sanger sequenced. Black lines, deleted genomic regions. Note the existence of three bi-directional deletion events from PCR of lanes 19-20.

DETAILED DESCRIPTION OF THE INVENTION

The present disclosure is predicated, at least in part, on the characterization of a miniature subtype of the type I CRISPR system from *Neisseria lactamica* (Nla). The Nla type I-C CRISPR system provides several advantages over previously characterized type I-E CRISPR-Cas systems. For example, the type I-C CRISPR gene region is the most streamlined and compact among all type I CRISPRs, requiring only four Cas genes and one CRISPR array, with a total gene size of about 5.8 kb. The reduced size of type I-C CRISPR loci as compared to type I-E systems (~8.5 kb) makes type I-C CRISPR-Cas systems more amenable to viral vector-based mammalian delivery. In addition, when delivered as a ribonucleoprotein (RNP) complex, the Nla type I-C system exhibits extremely high genome editing activity (50-96%) in various human cell lines, inducing large genome deletions that are unidirectional, heterogenous, and are created in a CRISPR-reprogrammable fashion. The Nla type I-C CRISPR-Cas system may also be transfected into human cells via plasmid vectors or as naked mRNA. Purification and preparation of the Nla type I-C RNP is also easier than purification of type I-E CRISPR-Cas systems, favoring large-scale production.

Definitions

To facilitate an understanding of the present technology, a number of terms and phrases are defined below. Additional definitions are set forth throughout the detailed description.

As used herein, a "nucleic acid" or a "nucleic acid sequence" refers to a polymer or oligomer of pyrimidine and/or purine bases, preferably cytosine, thymine, and uracil, and adenine and guanine, respectively (See Albert L. Lehninger, *Principles of Biochemistry*, at 793-800 (Worth Pub. 1982)). The present technology contemplates any deoxyribonucleotide, ribonucleotide, or peptide nucleic acid component, and any chemical variants thereof, such as methylated, hydroxymethylated, or glycosylated forms of these bases, and the like. The polymers or oligomers may be heterogenous or homogenous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. In some embodiments, a nucleic acid or nucleic acid sequence comprises other kinds of nucleic acid structures such as, for instance, a DNA/RNA helix, peptide nucleic acid (PNA), morpholino nucleic acid (see, e.g., Braasch and Corey, *Biochemistry*, 41(14): 4503-4510 (2002)) and U.S. Pat. No. 5,034,506), locked nucleic acid (LNA; see Wahlestedt et al., *Proc. Natl. Acad. Sci. U.S.A.*, 97: 5633-5638 (2000)), cyclohexenyl nucleic acids (see Wang, *J. Am. Chem. Soc.*, 122: 8595-8602 (2000)), and/or a ribozyme. Hence, the term "nucleic acid" or "nucleic acid sequence" may also encompass a chain comprising non-natural nucleotides, modified nucleotides, and/or non-nucleotide building blocks that can exhibit the same function as natural nucleotides (e.g., "nucleotide analogs"); further, the term "nucleic acid sequence" as used herein refers to an oligonucleotide, nucleotide or polynucleotide, and fragments or portions thereof, and to DNA or RNA of genomic or synthetic origin, which may be single or double-stranded, and represent the sense or antisense strand. The terms "nucleic acid," "polynucleotide," "nucleotide sequence," and "oligonucleotide" are used interchangeably. They refer to a polymeric form of nucleotides of any length, either deoxyribonucleotides or ribonucleotides, or analogs thereof.

The terms "complementary" and "complementarity" refer to the ability of a nucleic acid to form hydrogen bond(s) with another nucleic acid sequence by either traditional Watson-Crick base-paring or other non-traditional types of pairing. The degree of complementarity between two nucleic acid sequences can be indicated by the percentage of nucleotides in a nucleic acid sequence which can form hydrogen bonds (e.g., Watson-Crick base pairing) with a second nucleic acid sequence (e.g., 50%, 60%, 70%, 80%, 90%, and 100% complementary). Two nucleic acid sequences are "perfectly complementary" if all the contiguous nucleotides of a nucleic acid sequence will hydrogen bond with the same number of contiguous nucleotides in a second nucleic acid sequence. Two nucleic acid sequences are "substantially complementary" if the degree of complementarity between the two nucleic acid sequences is at least 60% (e.g., 65%, 70%, 75%, 80%, 85%, 90%, 95%. 97%, 98%, 99%, or 100%) over a region of at least 8 nucleotides (e.g., 9, 10, 11, 12, 13, 14, 15, 16, 17, 18, 19, 20, 21, 22, 23, 24, 25, 30, 35, 40, 45, 50, or more nucleotides), or if the two nucleic acid sequences hybridize under at least moderate, preferably high, stringency conditions. Exemplary moderate stringency conditions include overnight incubation at 37° C. in a solution comprising 20% formamide, 5×SSC (150 mM NaCl, 15 mM trisodium citrate), 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C., or substantially similar conditions, e.g., the moderately stringent conditions described in Sambrook et al., infra. High stringency conditions are conditions that use, for example

8

(1) low ionic strength and high temperature for washing, such as 0.015 M sodium chloride/0.0015 M sodium citrate/0.1% sodium dodecyl sulfate (SDS) at 50° C., (2) employ a denaturing agent during hybridization, such as formamide, for example, 50% (v/v) formamide with 0.1% bovine serum albumin (BSA)/0.1% Ficoll/0.1% polyvinylpyrrolidone (PVP)/50 mM sodium phosphate buffer at pH 6.5 with 750 mM sodium chloride and 75 mM sodium citrate at 42° C., or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at (i) 42° C. in 0.2×SSC, (ii) 55° C. in 50% formamide, and (iii) 55° C. in 0.1×SSC (preferably in combination with EDTA). Additional details and an explanation of stringency of hybridization reactions are provided in, e.g., Sambrook et al., *Molecular Cloning: A Laboratory Manual,* 3rd ed., Cold Spring Harbor Press, Cold Spring Harbor, N.Y. (2001); and Ausubel et al., *Current Protocols in Molecular Biology*, Greene Publishing Associates and John Wiley & Sons, New York (1994).

As used herein, the term "percent sequence identity" refers to the percentage of nucleotides or nucleotide analogs in a nucleic acid sequence, or amino acids in an amino acid sequence, that is identical with the corresponding nucleotides or amino acids in a reference sequence after aligning the two sequences and introducing gaps, if necessary, to achieve the maximum percent identity. Hence, in case a nucleic acid according to the technology is longer than a reference sequence, additional nucleotides in the nucleic acid, that do not align with the reference sequence, are not taken into account for determining sequence identity. Methods and computer programs for alignment are well known in the art, including BLAST, Align 2, and FASTA.

The term "homology" and "homologous" refers to a degree of identity. There may be partial homology or complete homology. A partially homologous sequence is one that is less than 100% identical to another sequence.

As used herein, the term "hybridization" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, and the Tm of the formed hybrid. Hybridization methods involve the annealing of one nucleic acid to another, complementary nucleic acid, e.g., a nucleic acid having a complementary nucleotide sequence. The ability of two polymers of nucleic acid containing complementary sequences to find each other and "anneal" or "hybridize" through base pairing interaction is a well-recognized phenomenon. The initial observations of the "hybridization" process by Marmur and Lane, *Proc. Natl. Acad. Sci. USA,* 46: 453 (1960) and Doty et al., *Proc. Natl. Acad. Sci. USA,* 46: 461 (1960), have been followed by the refinement of this process into an essential tool of modern biology. For example, hybridization and washing conditions are now well known and exemplified in Sambrook et al., supra. The conditions of temperature and ionic strength determine the "stringency" of the hybridization.

As used herein, a "double-stranded nucleic acid" may be a portion of a nucleic acid, a region of a longer nucleic acid, or an entire nucleic acid. A "double-stranded nucleic acid" may be, e.g., without limitation, a double-stranded DNA, a double-stranded RNA, a double-stranded DNA/RNA hybrid, etc. A single-stranded nucleic acid having secondary structure (e.g., base-paired secondary structure) and/or higher order structure (e.g., a stem-loop structure) may also be considered a "double-stranded nucleic acid." For example, triplex structures are considered to be "double-stranded." In some embodiments, any base-paired nucleic acid is a "double-stranded nucleic acid."

The term "gene" refers to a DNA sequence that comprises control and coding sequences necessary for the production of an RNA having a non-coding function (e.g., a ribosomal or transfer RNA), a polypeptide, or a precursor of any of the foregoing. The RNA or polypeptide can be encoded by a full length coding sequence or by any portion of the coding sequence so long as the desired activity or function is retained. Thus, a "gene" refers to a DNA or RNA, or portion thereof, that encodes a polypeptide or an RNA chain that has functional role to play in an organism. For the purpose of this disclosure, it may be considered that genes include regions that regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, and locus control regions.

The term "wild-type" refers to a gene or a gene product that has the characteristics of that gene or gene product when isolated from a naturally occurring source. A wild-type gene is that which is most frequently observed in a population and is thus arbitrarily designated the "normal" or "wild-type" form of the gene. In contrast, the term "modified," "mutant," or "polymorphic" refers to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the term "variant" refers to the exhibition of qualities that have a pattern that deviates from what occurs in nature. In some embodiments, a variant may also be a mutant.

The terms "non-naturally occurring," "engineered," and "synthetic" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

The term "oligonucleotide" as used herein is defined as a molecule comprising two or more deoxyribonucleotides or ribonucleotides, preferably at least 5 nucleotides, more preferably at least about 10 to 15 nucleotides and more preferably at least about 15 to 50 nucleotides (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more nucleotides). The exact size will depend on many factors, which in turn depend on the ultimate function or use of the oligonucleotide. The oligonucleotide may be generated in any manner, including chemical synthesis, DNA replication, reverse transcription, PCR, or a combination thereof.

The terms "peptide" and "polypeptide" and "protein" are used interchangeably herein, and refer to a polymeric form of amino acids of any length, which can include coded and non-coded amino acids, chemically or biochemically modified or derivatized amino acids, and polypeptides having modified peptide backbones.

"Binding" as used herein (e.g., with reference to an RNA-binding domain of a polypeptide) refers to a non-covalent interaction between macromolecules (e.g., between a protein and a nucleic acid). While in a state of non-covalent interaction, the macromolecules are said to be "associated" or "interacting" or "binding" (e.g., when a molecule X is said to interact with a molecule Y, it is meant the molecule X binds to molecule Y in a non-covalent manner). Not all components of a binding interaction need be sequence-specific (e.g., contacts with phosphate residues in a DNA backbone), but some portions of a binding interaction may be sequence specific. Binding interactions are generally characterized by a dissociation constant ($K_d$) of less than $10^{-6}$ M, less than $10^{-7}$ M, less than $10^{-8}$ M, less than $10^{-9}$ M, less than $10^{-10}$ M, less than $10^{-11}$M, less than $10^{-12}$M, less than $10^{-13}$ M, less than $10^{-14}$M, or less than $10^{-15}$ M. "Affinity" refers to the strength of binding, increased binding affinity being correlated with a lower $K_d$.

By "binding domain" it is meant a protein domain that is able to bind non-covalently to another molecule. A binding domain can bind to, for example, a DNA molecule (a DNA-binding protein), an RNA molecule (an RNA-binding protein) and/or a protein molecule (a protein binding protein). In the case of a protein domain-binding protein, it can bind to itself (to form homodimers, homotrimers, etc.) and/or it can bind to one or more molecules of a different protein or proteins.

"Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms). Alternatively, DNA sequences encoding RNA (e.g., DNA-targeting RNA) that is not translated may also be considered recombinant. Thus, the term "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques. When a recombinant polynucleotide encodes a polypeptide, the sequence of the encoded polypeptide can be naturally occurring ("wild type") or can be a variant (e.g., a mutant) of the naturally occurring sequence. Thus, the term "recombinant" polypeptide does not necessarily refer to a polypeptide whose sequence does not naturally occur. Instead, a "recombinant" polypeptide is encoded by a recombinant DNA sequence, but the sequence of the polypeptide can be naturally occurring ("wild type") or non-naturally occurring (e.g., a variant, a mutant, etc.). Thus, a "recombinant" polypeptide is the result of human intervention, but may be a naturally occurring amino acid sequence.

A "vector" or "expression vector" is a replicon, such as plasmid, phage, virus, or cosmid, to which another DNA segment, i.e., an "insert," may be attached or incorporated so as to bring about the replication of the attached segment in a cell.

A cell has been "genetically modified," "transformed," or "transfected" by exogenous DNA, e.g., a recombinant expression vector, when such DNA has been introduced inside the cell. The presence of the exogenous DNA results in permanent or transient genetic change. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones that comprise a population of daughter cells containing the transforming DNA. A "clone" is a population of cells derived from a single cell or common ancestor by mitosis. A "cell line" is a clone of a primary cell that is capable of stable growth in vitro for many generations.

As used herein, "CRISPR-Cas system" refers collectively to transcripts and other elements involved in the expression of and/or directing the activity of CRISPR-associated ("Cas") genes, including sequences encoding a Cas gene, Cas protein, a cr (CRISPR) sequence (e.g., crRNA or an active partial crRNA), or other sequences and transcripts from a CRISPR locus. In some embodiments, one or more elements of a CRISPR system is derived from a type I, type II, or type III CRISPR system.

The term "cascade (CRISPR-Associated Complex for Anti-viral Defense)," as used herein, refers to a ribonucleoprotein complex comprised of multiple protein subunits and is used naturally in bacteria as a mechanism for nucleic acid-based immune defense. Cascade complexes are characteristic of the type I CRISPR systems. The cascade complex recognizes nucleic acid targets via direct base-pairing to guide RNA contained in the complex. Acceptance of target recognition by Cascade results in a conformational change which, in E. coli and other bacteria, recruits a protein component referred to as Cas3. Cas3 may comprise a single protein unit which contains helicase and nuclease domains. After target validation by Cascade, Cas3 nicks the strand of DNA that is looped out by the R-loop formed by Cascade approximately 9-12 nucleotides inward from the PAM site. Cas3 then uses its helicase/nuclease activity to processively degrade substrate nucleic acids, moving in a 3' to 5' direction.

Methods of Altering Genomic DNA

The disclosure provides a method of altering a target genomic DNA sequence in a host cell, which method comprises introducing into a host cell comprising a target DNA sequence (e.g., genomic sequence): (a) a synthetic guide RNA sequence(s) that is complementary to a target DNA sequence(s) in a host cell (e.g., wherein the target DNA sequence(s) encodes at least one gene product); and (b) a combination of two or more Neisseria lactamica proteins selected from Cas3, Cas5, Cas8c, and Cas7, wherein the synthetic guide RNA sequence binds to the target DNA sequence in the host cell, and the combination of two or more N. lactamica proteins induces cleavage of one or both strands in the target DNA sequence, thereby altering the target DNA sequence in the host cell.

As discussed above, CRISPR-Cas gene editing systems have been developed to enable targeted modifications to a specific gene of interest in eukaryotic cells. In bacteria and archaea, CRISPR-Cas systems provide immunity by incorporating fragments of invading phage, virus, and plasmid DNA into CRISPR loci and using corresponding CRISPR RNAs ("crRNAs") to guide the degradation of homologous sequences. Each CRISPR locus encodes acquired "spacers" that are separated by repeat sequences. Transcription of a CRISPR locus produces a "pre-crRNA," which is processed to yield crRNAs containing spacer-repeat fragments that guide effector nuclease complexes to cleave dsDNA sequences complementary to the spacer. The most widely used CRISPR-Cas gene editing systems are based on the RNA-guided Cas9 nuclease from the type II prokaryotic CRISPR adaptive immune system (see, e.g., Jinek et al., Science, 337: 816 (2012); Gasiunas et al., Proc. Natl. Acad. Sci. U.S.A., 109, E2579 (2012); Garneau et al., Nature, 468: 67 (2010); Deveau et al., Annu. Rev. Microbiol., 64: 475 (2010); Horvath and Barrangou, Science, 327: 167 (2010); Makarova et al., Nat. Rev. Microbiol., 9, 467 (2011); Bhaya et al., Annu. Rev. Genet., 45: 273 (2011); and Cong et al., Science, 339: 819-823 (2013)). CRISPR-Cas systems generally are classified into two major classes, six distinct main types, and over twenty subtypes, and signature genes have been identified for most major types (Marakova, K. S. and Koonin, E. V., Methods Mol Biol., 1311: 47-75 (2015); Makarova et al., Nature Reviews Microbiology, 18: 67-83 (2020)). The main types are readily distinguishable by virtue of the presence of their unique signature genes: cas3, cas9, cas10, cas12, and cas13, in types I, II, III, V, and VI systems, respectively (Marakova, K. S. and Koonin, E. V., Methods Mol Biol., 1311: 47-75 (2015)).

A CRISPR-Cas system of any type or subtype may be used in the context of the present disclosure; however, a type I CRISPR-Cas system is preferred. All type I CRISPR loci contain the signature cas3 gene, which encodes a large protein with a helicase possessing a single-stranded DNA (ssDNA)-stimulated ATPase activity coupled to unwinding of DNA-DNA and RNA-DNA duplexes (Sinkunas et al., EMBO J., 30: 1335-1342 (2011)). Type I systems are divided into seven subtypes, I-A to I-G, each of which has its distinct features of operon organization (see, e.g., Marakova and Koonin, supra; and Makarova et al., Nature Reviews Microbiology, 18: 67-83 (2020)). Unlike other subtypes, I-E and I-F lack the cas4 gene. In type II systems, crRNA processing is mediated by a host factor, RNase III, and a second small non-coding RNA cofactor called tracrRNA (Deltcheva et al., Nature, 471: 602-607 (2011)). In contrast, class I systems use a dedicated Cas protein as the crRNA processing endonuclease and do not employ an auxiliary tracrRNA (Brouns et al., Science, 321: 960-964 (2008); Carte et al., Genes Dev., 22: 3489-3496 (2008)).

Elements or sequences from any suitable type I-C CRISPR-Cas system may be used in the context of the disclosed methods. In some embodiments, the type I-C CRISPR-Cas system may be based on CRISPR-Cas elements (e.g., Cascade-Cas3 proteins or variants thereof) from a *Neisseria* species (e.g., *Neisseria lactamica*). The genus *Neisseria* comprises many gram-negative β-proteobacteria that interact with eukaryotic hosts, but only two organisms, the gonococcus (Gc) and its close relative the meningococcus (Mc), are human pathogens, both of which colonize mucosal surfaces (Bratcher, Bennett, and Maiden, *Future Microbiol.*, 7: 873-885 (2012); Rotman and Seifert, *Annu Rev Genet*, 48: 405-31(2014)). Many non-pathogenic *Neisseria* species also colonize the human nasopharynx, and among them *N. lactamica* is the most widely studied commensal bacterium (Rotman and Seifert, supra).

The CRISPR-Cas system used in the context of the present disclosure desirably is based on the type I-C system of *Neisseria lactamica* (Nla), or variants thereof.

The type I-C CRISPR locus of *N. lactamica* comprises four genes encoding Cas7, Cas8c, Cas5, and Cas3 proteins, and one CRISPR RNA (also referred to as CRISPR array or "crRNA"). The native Nla CRISPR array contains multiple identical repeats separated by unique spacers. Proteins Cas7, Cas8c, Cas5 and CRISPR RNA form the Cascade complex, which recognizes its CRISPR-complementary DNA target site. The Cas3 nuclease-helicase is then recruited to the PAM-flanked target site to initiate DNA destruction. The *N. lactamica* CRISPR locus is schematically illustrated in FIG. 1. Variants of *N. lactamica* Cascade-Cas3 proteins include any protein having an amino acid sequence that is at least about 85% identical (e.g., about 86%, about 87%, about 88%, about 89%, about 90%, about 91%, about 92%, about 93%, about 94%, about 95%, about 96%, about 97%, about 98%, about 99%, or about 100%) to the amino acid sequence of any protein of the *N. lactamica* type I-C Cascade-Cas3 complex.

The *N. lactamica* CRISPR-Cas3 elements typically are active in a host cell genome which comprises a protospacer adjacent motif (PAM) comprising the nucleic acid sequence 5'-TTC-3' or 5'-TTT-3' located adjacent to the target genomic DNA sequence. The PAM for type I CRISPR is "adjacent to" the target genomic DNA sequence in that it typically immediately precedes the target sequence.

In certain embodiments, engineering the type I-C CRISPR-Cas system for use in eukaryotic cells involves reconstitution of the Cascade-Cas3 complex. In human cells, for example, each of the nucleic acid sequences encoding Cas7, Cas8c, Cas5, and Cas3 proteins may be codon-optimized and/or modified to include an appropriate nuclear localization signal (NLS) or purification tag, and expressed on separate plasmids. Alternatively, the Cascade proteins Cas7, Cas8c, and Cas5 may be expressed from a single plasmid, with the Cas3 protein expressed on a different plasmid. It will be appreciated that any combination of two or more *Neisseria lactamica* proteins selected from Cas3, Cas5, Cas8c, and Cas7 may be introduced into a host cell; however, the Cas3 protein preferably is included to initiate DNA cleavage. In some embodiments, all of the *Neisseria lactamica* proteins Cas3, Cas5, Cas8c, and Cas7 are introduced into host cells. Furthermore, in some embodiments, engineering the type I-C CRISPR-Cas involves incorporating elements of the native *Neisseria lactamica* CRISPR array into the reconstituted Nla CRISPR-Cas3 complex. For example, an engineered Nla CRISPR may comprise contains two repeats and one spacer, or three repeats and two identical spacers. An exemplary Nla-CRISPR-repeat amino acid sequence may comprise SEQ ID NO: 5.

The crRNA may also be expressed separately via an RNA polymerase III promoter (e.g., a U6 promoter). Typically, the reconstituted crRNA sequence is referred to as "guide RNA" (gRNA). Thus, the terms "guide RNA" and "synthetic guide RNA," are used interchangeably herein and refer to a nucleic acid sequence comprising a pre-crRNA array containing a guide sequence. The terms "guide sequence," "guide," and "spacer," are used interchangeably herein and refer to the nucleotide sequence within a guide RNA that specifies the target site. Collectively, the Nla CRISPR-Cas3 components reconstituted for gene editing in eukaryotic cells is referred to herein as the "Nla CRISPR-Cas3 system."

The phrase "altering a DNA sequence," as used herein, refers to modifying at least one physical feature of a wild-type DNA sequence of interest. DNA alterations include, for example, single or double strand DNA breaks, deletion, or insertion of one or more nucleotides, and other modifications that affect the structural integrity or nucleotide sequence of the DNA sequence. In one embodiment, the method introduces a single strand or double strand break in the target DNA sequence. In this respect, the Nla CRISPR-Cas3 system may direct cleavage of one or both strands of a target DNA sequence, such as within the target genomic DNA sequence and/or within the complement of the target sequence. In some embodiments, The Nla CRISPR-Cas3 system introduces a long range and unidirectional genomic DNA deletion upstream of the PAM without prominent off-target activity. The deletion of the target genomic DNA sequence may be of any size. For example, in some embodiments the deletion of genomic DNA comprises from about 500 nucleotides to about 100,000 nucleotides (e.g., about 1,000, 5,000, 10,000, or 50,000 nucleotides, or a range defined by any two of the foregoing values). In other embodiments, the deletion of genomic DNA comprises from about 5,000 nucleotides to about 20,000 nucleotides (e.g., about 6,000, 6,500, 7,000, 7,500, 8,000, 8,500, 9,000, 9,500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, or 19,500 nucleotides, or a range defined by any two of the foregoing values).

The terms "target sequence," "target nucleic acid," and "target site" (e.g., a "target genomic DNA sequence") are used interchangeably herein to refer to a polynucleotide (nucleic acid, gene, chromosome, genome, etc.) in a host cell to which a guide sequence (e.g., a synthetic guide RNA) is designed to have complementarity, wherein hybridization between the target sequence and a guide sequence promotes the formation of a CRISPR complex, provided sufficient conditions for binding exist. The term "genomic," as used herein, refers to a nucleic acid sequence (e.g., a gene or locus) that is located on a chromosome in a cell. The target sequence and guide sequence need not exhibit complete complementarity, provided that there is sufficient complementarity to cause hybridization and promote formation of a CRISPR complex. A target sequence may comprise any polynucleotide, such as DNA or RNA. Suitable DNA/RNA binding conditions include physiological conditions normally present in a cell. Other suitable DNA/RNA binding conditions (e.g., conditions in a cell-free system) are known in the art; see, e.g., Sambrook, supra. The strand of the target DNA that is complementary to and hybridizes with the DNA-targeting RNA is referred to as the "complementary strand" and the strand of the target DNA that is complementary to the "complementary strand" (and is therefore not complementary to the DNA-targeting RNA) is referred to as the "noncomplementary strand" or "non-complementary strand."

The target genomic DNA sequence desirably encodes a gene product. The term "gene product," as used herein, refers to any biochemical product resulting from expression of a gene. Gene products may be RNA or protein. RNA gene products include non-coding RNA, such as tRNA, rRNA, micro RNA (miRNA), and small interfering RNA (siRNA), and coding RNA, such as messenger RNA (mRNA). In some embodiments, the target genomic DNA sequence encodes a protein or polypeptide. However, the invention is not limited to editing of gene products. Any target DNA sequence may be edited, as desired.

Desirably, the disclosed method alters a target genomic DNA sequence in a host cell so as to modulate expression of the target DNA sequence, i.e., expression of the target DNA sequence is increased, decreased, or completely eliminated (e.g., via deletion of a gene). In one embodiment, the Nla CRISPR-Cas3 system cleaves a target DNA sequence of the host cell to produce double strand DNA breaks. The double strand breaks can be repaired by the host cell by either non-homologous end joining (NHEJ) or homologous recombination. In NHEJ, the double-strand breaks are repaired by direct ligation of the break ends to one another. In homologous recombination repair, a donor nucleic acid molecule comprising a second DNA sequence with homology to the cleaved target DNA sequence is used as a template for repair of the cleaved target DNA sequence, resulting in the transfer of genetic information from the donor nucleic acid molecule to the target DNA. As a result, new nucleic acid material is inserted/copied into the DNA break site. The modifications of the target sequence due to NHEJ and/or homologous recombination repair lead to, for example, gene correction, gene replacement, gene tagging, transgene insertion, nucleotide deletion, gene disruption, gene mutation, gene knockdown, etc.

In some embodiments, the systems and methods described herein may be used to correct one or more defects or mutations in a gene (referred to as "gene correction"). In such cases, the target genomic DNA sequence encodes a defective version of a gene, and the Nla CRISPR-Cas3 system further comprises a donor nucleic acid molecule which encodes a wild-type or corrected version of the gene. Thus, in other words, the target genomic DNA sequence is a "disease-associated" gene. The term "disease-associated gene," refers to any gene or polynucleotide whose gene products are expressed at an abnormal level or in an abnormal form in cells obtained from a disease-affected individual as compared with tissues or cells obtained from an individual not affected by the disease. A disease-associated gene may be expressed at an abnormally high level or at an abnormally low level, where the altered expression correlates with the occurrence and/or progression of the disease. A disease-associated gene also refers to a gene, the mutation or genetic variation of which is directly responsible or is in linkage disequilibrium with a gene(s) that is responsible for the etiology of a disease. Examples of genes responsible for such "single gene" or "monogenic" diseases include, but are not limited to, adenosine deaminase, α-1 antitrypsin, cystic fibrosis transmembrane conductance regulator (CFTR), β-hemoglobin (HBB), oculocutaneous albinism II (OCA2), Huntingtin (HTT), dystrophia myotonica-protein kinase (DMPK), low-density lipoprotein receptor (LDLR), apolipoprotein B (APOB), neurofibromin 1 (NF1), polycystic kidney disease 1 (PKD1), polycystic kidney disease 2 (PKD2), coagulation factor VIII (F8), dystrophin (DMD), phosphate-regulating endopeptidase homologue, X-linked (PHEX), methyl-CpG-binding protein 2 (MECP2), and ubiquitin-specific peptidase 9Y, Y-linked (USP9Y). Other single gene or monogenic diseases are known in the art and described in, e.g., Chial, H. *Rare Genetic Disorders: Learn-* ing *About Genetic Disease Through Gene Mapping, SNPs, and Microarray Data*, Nature Education 1 (1): 192 (2008); Online Mendelian Inheritance in Man (OMIM) (ncbi.nim-.nih.gov/entrez/query.fcgi?db=OMIM); and the Human Gene Mutation Database (HGMD) (hgmd.cf.ac.uk). In another embodiment, the target genomic DNA sequence can comprise a gene, the mutation of which contributes to a particular disease in combination with mutations in other genes. Diseases caused by the contribution of multiple genes which lack simple (i.e., Mendelian) inheritance patterns are referred to in the art as a "multifactorial" or "polygenic" disease. Examples of multifactorial or polygenic diseases include, but are not limited to, asthma, diabetes, epilepsy, hypertension, bipolar disorder, and schizophrenia. Certain developmental abnormalities also can be inherited in a multifactorial or polygenic pattern and include, for example, cleft lip/palate, congenital heart defects, and neural tube defects.

In another embodiment, the method of altering a target genomic DNA sequence can be used to delete nucleic acids from a target sequence in a host cell by cleaving the target sequence and allowing the host cell to repair the cleaved sequence in the absence of an exogenously provided donor nucleic acid molecule. Deletion of a nucleic acid sequence in this manner can be used in a variety of applications, such as, for example, to remove disease-causing trinucleotide repeat sequences in neurons, to create gene knock-outs or knock-downs, and to generate mutations for disease models in research.

The various components of the Nla CRISPR-Cas3 system described herein may be introduced into a host cell in any suitable manner. In some embodiments, nucleic acid sequences encoding the various components of the Nla CRISPR-Cas3 system may be introduced into host cells as part of vector, optionally operably linked to one or more expression control sequences (e.g., promoters, enhancers, polyadenylation signals, transcription terminators, internal ribosome entry sites (IRES), and the like) that provide for the expression of a nucleic acid sequence in a host cell (e.g., a mammalian cell). The vector can be, for example, a plasmid, episome, cosmid, viral vector (e.g., retrovirus, adenovirus, lentivirus, or adeno-associated virus vector), or phage. Suitable vectors and methods of vector preparation are well known in the art (see, e.g., Sambrook et al., *Molecular Cloning, a Laboratory Manual*, 3rd edition, Cold Spring Harbor Press, Cold Spring Harbor, N.Y. (2001), and Ausubel et al., *Current Protocols in Molecular Biology*, Greene Publishing Associates and John Wiley & Sons, New York, N.Y. (1994)). Exemplary expression control sequences for control of gene expression in vector systems include prokaryotic and eukaryotic sequences described in, for example, Goeddel, *Gene Expression Technology: Methods in Enzymology*, Vol. 185, Academic Press, San Diego, Calif. (1990), Sambrook et al., supra; and Ausubel et al., supra.

The choice of expression control sequences, such as promoters, depends on the particular application of the vector and systems described herein. A large number of promoters, including constitutive, inducible, and repressible promoters, from a variety of different sources are well known in the art. Representative sources of promoters include for example, virus, mammal, insect, plant, yeast, and bacteria, and suitable promoters from these sources are readily available, or can be made synthetically, based on sequences publicly available, for example, from depositories such as the ATCC as well as other commercial or individual sources. Promoters can be unidirectional (i.e., initiate transcription in one direction) or bi-directional (i.e., initiate transcription in either a 3' or 5' direction). The majority of CRISPR-Cas gene editing systems utilize RNA Polymerase III (Pol III) promoters for transcription of guide RNA sequences (Cong et al., *Science,* 339: 819-823 (2013); and Mali et al., *Science,* 339: 823-826 (2013)). RNA Pol III promoters normally transcribe ribosomal 5S rRNA genes, tRNA genes, and some small nuclear RNA genes such as U6 and U3 snRNA genes. Thus, promoters for any of these genes may be operably linked to one or more nucleic acid sequences encoding components of the Nla CRISPR-Cas3 system. Non-limiting examples of other promoters that may be used include the T7 bacterial expression system, pBAD (araA) bacterial expression system, the cytomegalovirus (CMV) promoter, or the SV40 promoter. Inducible promoters may also be employed.

As discussed above, nucleic acid sequences encoding the components of the Nla CRISPR-Cas3 system (e.g., Cas3, Cas7, Cas8c, Cas5) can be provided to a cell on the same vector (i.e., in cis) as the synthetic guide RNA sequence. In such embodiments, a unidirectional promoter can be used to control expression of each nucleic acid sequence. In another embodiment, a combination of bidirectional and unidirectional promoters can be used to control expression of multiple nucleic acid sequences. Alternatively, when nucleic acid sequences encoding the components of the Nla CRISPR-Cas3 system (e.g., Cas3, Cas7, Cas8c, Cas5) and the synthetic guide RNA sequence are provided to a cell on separate vectors (i.e., in trans), each of the nucleic acid sequences in each of the separate vectors can comprise the same or different expression control sequences. For example, the synthetic guide RNA sequence may be introduced into the host cell as part of a first vector and one or more nucleic acid sequences encoding the two or more of the *N. lactamica* Cas3, Cas5, Cas8c, or Cas7 proteins are introduced into the host cell as part of a second vector, wherein the first vector and the second vector are different. The separate vectors can be provided to cells simultaneously or sequentially.

In other embodiments, various components of the Nla CRISPR-Cas3 system may be introduced into a host cell as a ribonucleoprotein (RNP) complex. The term "ribonucleoprotein complex," as used herein, refers to a complex of ribonucleic acid and RNA-binding protein(s). In the context of CRISPR-Cas systems, an RNP complex typically comprises Cas protein(s) (e.g., Cas5, Cas7, and Cas8) in complex with a gRNA. RNPs may be assembled in vitro and can be delivered directly to cells using standard electroporation, cationic lipids, gold nanoparticles, or other transfection techniques (see, e.g., Kim et al., *Genome Res.,* 24: 1012-1019 (2014); Zuris et al., *Nat. Biotechnol.,* 33: 73-80 (2015); and Mout et al., *ACS Nano.,* 11: 2452-2458 (2017)). Alternatively, the two or more *N. lactamica* Cas proteins may be introduced into a host cell by contacting the host cell with one or more mRNA sequences encoding the two or more *N. lactamica* proteins (i.e., as "naked" RNA) in combination with a separate synthetic guide RNA sequence.

A vector, RNP complex, or naked RNA can be introduced into a host cell that is capable of expressing the proteins encoded thereby, including any suitable prokaryotic or eukaryotic cell. As such, the disclosure provides an isolated cell comprising the vector, RNP complex, or naked RNA disclosed herein. Preferred host cells are those that can be easily and reliably grown, have reasonably fast growth rates, have well characterized expression systems, and can be transformed or transfected easily and efficiently. Examples of suitable prokaryotic cells include, but are not limited to, cells from the genera *Bacillus* (such as *Bacillus subtilis* and *Bacillus brevis*), *Escherichia* (such as *E. coli*), *Pseudomonas, Streptomyces, Salmonella,* and *Envinia.* Suitable eukaryotic cells are known in the art and include, for example, yeast cells, insect cells, and mammalian cells. Examples of suitable yeast cells include those from the genera *Kluyveromyces, Pichia, Rhino-sporidium, Saccharomyces,* and *Schizosaccharomyces.* Exemplary insect cells include Sf-9 and HIS (Invitrogen, Carlsbad, Calif.) and are described in, for example, Kitts et al., *Biotechniques,* 14: 810-817 (1993); Lucklow, *Curr. Opin. Biotechnol.,* 4: 564-572 (1993); and Lucklow et al., *J. Virol.,* 67: 4566-4579 (1993). Desirably, the host cell is a mammalian cell, and in some embodiments, the host cell is a human cell. A number of suitable mammalian and human host cells are known in the art, and many are available from the American Type Culture Collection (ATCC, Manassas, Va.). Examples of suitable mammalian cells include, but are not limited to, Chinese hamster ovary cells (CHO) (ATCC No. CCL61), CHO DHFR-cells (Urlaub et al., *Proc. Natl. Acad. Sci. USA,* 97: 4216-4220 (1980)), human embryonic kidney (HEK) 293 or 293T cells (ATCC No. CRL1573), and 3T3 cells (ATCC No. CCL92). Other suitable mammalian cell lines are the monkey COS-1 (ATCC No. CRL1650) and COS-7 cell lines (ATCC No. CRL1651), as well as the CV-1 cell line (ATCC No. CCL70). Further exemplary mammalian host cells include primate, rodent, and human cell lines, including transformed cell lines. Normal diploid cells, cell strains derived from in vitro culture of primary tissue, as well as primary explants, are also suitable. Other suitable mammalian cell lines include, but are not limited to, mouse neuroblastoma N2A cells, HeLa, mouse L-929 cells, and BHK or HaK hamster cell lines, all of which are available from the ATCC. Methods for selecting suitable mammalian host cells and methods for transformation, culture, amplification, screening, and purification of cells are known in the art.

It will be appreciated that changing all of the native *N. lactamica* codons to those most frequently used in mammals allows for maximum expression of *N. lactamica* Cas proteins in mammalian cells (e.g., human cells). Such modified nucleic acid sequences are commonly described in the art as "codon-optimized," or as utilizing "mammalian-preferred" or "human-preferred" codons. In embodiments of the invention, an *N. lactamica* nucleic acid sequence is said to be "codon-optimized" if at least about 60% (e.g., at least about 70%, at least about 80%, or at least about 90%) of the wild-type codons in the nucleic acid sequence are modified to encode mammalian-preferred codons. That is, an *N. lactamica* nucleic acid sequence is codon-optimized if at least about 60% of the codons encoded therein are mammalian preferred codons.

In certain embodiments, the Cas3 protein is encoded by the nucleic acid sequence of SEQ ID NO: 1 or SEQ ID NO: 7, the Cas5 protein is encoded by the nucleic acid sequence of SEQ ID NO: 2 or SEQ ID NO: 8, the Cas8c protein is encoded by the nucleic acid sequence of SEQ ID NO: 3 or SEQ ID NO: 9, and the Cas7 protein is encoded by the nucleic acid sequence of SEQ ID NO: 4 or SEQ ID NO: 10. However, the invention is not limited to these exemplary sequences. Indeed, genetic sequences can vary between different strains, and this natural scope of allelic variation is included within the scope of the invention.

Additionally and alternatively, a nucleic acid sequence encoding *N. lactamica* can be any sequence that hybridizes to the above-described sequences under at least moderate, preferably high, stringency conditions, such as those described herein and in, e.g., Sambrook et al., supra. Determining the degree of homology can be accomplished using any suitable method (e.g., BLASTnr, provided by Gen-Bank).

In certain embodiments, the Cas3 protein comprises the amino acid sequence of SEQ ID NO: 85, the Cas5 protein comprises the amino acid sequence of SEQ ID NO: 86, the Cas8c protein comprises the amino acid sequence of SEQ ID NO: 87, and the Cas7 protein comprises the amino acid sequence of SEQ ID NO: 88. However, the invention is not limited to these exemplary sequences.

In other embodiments, any of the *N. lactamica* Cas proteins described herein may comprise one or more amino acid substitutions as compared to the corresponding wild-type Nla protein. An amino acid "replacement" or "substitution" refers to the replacement of one amino acid at a given position or residue by another amino acid at the same position or residue within a polypeptide sequence. Amino acids are broadly grouped as "aromatic" or "aliphatic." An aromatic amino acid includes an aromatic ring. Examples of "aromatic" amino acids include histidine (H or His), phenylalanine (F or Phe), tyrosine (Y or Tyr), and tryptophan (W or Trp). Non-aromatic amino acids are broadly grouped as "aliphatic." Examples of "aliphatic" amino acids include glycine (G or Gly), alanine (A or Ala), valine (V or Val), leucine (L or Leu), isoleucine (I or He), methionine (M or Met), serine (S or Ser), threonine (T or Thr), cysteine (C or Cys), proline (P or Pro), glutamic acid (E or Glu), aspartic acid (A or Asp), asparagine (N or Asn), glutamine (Q or Gin), lysine (K or Lys), and arginine (R or Arg).

The amino acid replacement or substitution can be conservative, semi-conservative, or non-conservative. The phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz and Schirmer, *Principles of Protein Structure*, Springer-Verlag, New York (1979)). According to such analyses, groups of amino acids may be defined where amino acids within a group exchange preferentially with each other, and therefore resemble each other most in their impact on the overall protein structure (Schulz and Schirmer, supra).

Examples of conservative amino acid substitutions include substitutions of amino acids within the sub-groups described above, for example, lysine for arginine and vice versa such that a positive charge may be maintained, glutamic acid for aspartic acid and vice versa such that a negative charge may be maintained, serine for threonine such that a free —OH can be maintained, and glutamine for asparagine such that a free —NH$_2$ can be maintained. "Semi-conservative mutations" include amino acid substitutions of amino acids within the same groups listed above, but not within the same sub-group. For example, the substitution of aspartic acid for asparagine, or asparagine for lysine, involves amino acids within the same group, but different sub-groups. "Non-conservative mutations" involve amino acid substitutions between different groups, for example, lysine for tryptophan, or phenylalanine for serine, etc.

The disclosure also provides a system comprising the above-described Nla CRISPR-Cas3 components. Thus, the disclosure provides a system, and the use thereof, comprising: (a) a synthetic guide RNA sequence that is complementary to a target genomic DNA sequence in a host cell, wherein the target genomic DNA sequence encodes at least one gene product; and (b) a combination of two or more *Neisseria lactamica* proteins selected from Cas3, Cas5, Cas8c, and Cas7. The synthetic guide RNA sequence and nucleic acid sequences encoding the two or more *Neisseria lactamica* proteins may be present in different vectors or present in the same vector, as discussed above, or may be delivered as a ribonucleoprotein complex (RNP) or naked RNA. In some embodiments, the Cas3 protein may be included in the system separate from a vector encoding other elements of the system, it is desirably included in a single composition (e.g., a pharmaceutical composition) alone or in combination with one more vectors comprising the synthetic guide RNA sequence or encoding Cas3, Cas5, Cas8c, and/or Cas7 proteins, and is not physically or chemically bound to the vector. In other embodiments, the Cas3 protein may be "associated" with a vector comprising the guide RNA sequence if it is physically or chemically linked or bound to the vector, such that a complex between the Cas3 protein and vector is formed (e.g., a complex between the Cas3 protein and a viral vector). The Cas3 protein can be associated with a vector using any suitable method for protein-protein linking or protein-virus linking known in the art.

Any element of any suitable CRISPR-Cas gene editing system known in the art can be employed in the systems and methods described herein, as appropriate. CRISPR-Cas gene editing technology is described in detail in, for example, Cong et al., supra; Xie et al., supra; U.S. Patent Application Publication 2014/0068797; U.S. Pat. Nos. 8,697,359; 8,771, 945; and 8,945,839; US2010/0076057; US2011/0189776; US2011/0223638; US2013/0130248; WO 2008/108989; WO 2010/054108; WO 2012/164565; WO 2013/098244; WO 2013/176772; WO 2014/190181; WO 2019/246555; US20150050699; US20150045546; US20150031134; US20150024500; US20140377868; US20140357530; US20140349400; US20140335620; US20140335063; US20140315985; US20140310830; US20140310828; US20140309487; US20140304853; US20140298547; US20140295556; US20140294773; US20140287938; US20140273234; US20140273232; US20140273231; US20140273230; US20140271987; US20140256046; US20140248702; US20140242702; US20140242700; US20140242699; US20140242664; US20140234972; US20140227787; US20140212869; US20140201857; US20140199767; US20140189896; US20140186958; US20140186919; US20140186843; US20140179770; US20140179006; and US20140170753; Makarova et al., *Nature Reviews Microbiology*, 9(6): 467-477 (2011); Wiedenheft et al., *Nature*, 482: 331-338 (2012); Gasiunas et al., *Proceedings of the National Academy of Sciences USA*, 109(39): E2579-E2586 (2012); Jinek et al., *Science*, 337: 816-821 (2012); Carroll, *Molecular Therapy*, 20(9): 1658-1660 (2012); Al-Attar et al., *Biol Chem.*, 392(4): 277-289 (2011); Hale et al., *Molecular Cell*, 45(3): 292-302 (2012), and Zhang Y., Pathog Dis. 2017; 75(4):ftx036. doi:10.1093/femspd/ftx036.

In some embodiments, the invention provides kits containing one or more or all of the components useful, necessary, or sufficient to practice the methods described herein. For example, in some embodiments, the kits comprise one or more reagents (e.g., vectors, CRISPR-Cas system components of *Neisseria lactamica*, buffers, transfection reagents, positive or negative controls, etc.), containers, instructions for use, software, or the like.

The following examples further illustrate the invention but, of course, should not be construed as in any way limiting its scope.

EXAMPLES

The following materials and methods were used in the experiments described in the Examples.

Plasmid Transfection

The HAP1-AAVS1-EGFP reporter cell line was transfected using the Lipofectamine 3000 reagent (ThermoFisher Scientific, Waltham, MA) according to the manufacturer's instructions. The reporter cells were seeded one day before transfection at $1 \times 10^5$ cells per well of a 24-well plate. For each transfection, 500 ng plasmid was used (50 ng of CRISPR plasmid, 50 ng of cas3 plasmid, 25 ng of cas5 plasmid, 75 ng of cas7 plasmid, and 300 ng of cas8c plasmid) along with 1 µL of P3000 reagent and 1.5 µL of Lipofectamine 3000 reagent. Cells were analyzed using flow cytometry 5 days after transfection. For homology directed repair experiments, cas8c plasmid was reduced to 200 ng, 100 ng of the donor DNA plasmid was added to the plasmid mix.

Protein Purification of Nla-NLS-Cascade

Two methods were designed to purify Nla-Cascade complex. The first method used MBP affinity purification with an MBP tagged Cas5 protein followed by size exclusion chromatography. The second method used Ni affinity purification with a His tagged Cas7 protein followed by size exclusion chromatography.

Method 1: The two plasmids expressing cas5-cas8c-cas7-NLS and CRISPR were co-transformed into BL21(DE3) cells. The resulting strain was then inoculated into 10 mL of LB with 50 µg/mL of kanamycin and 20 µg/ml of chloramphenicol, and grown overnight at 37° C. This overnight culture was then used to inoculate a 1 L LB containing 50 µg/mL kanamycin, 20 µg/mL chloramphenicol, and 0.2% glucose. The large culture was cooled to 18° C. when it reached OD600 ~0.6 and induced with 1 mM IPTG for 18 hours at 18° C. Cells were then pelleted and resuspended in 20 mM HEPES pH 7.5 and 500 mM NaCl, and then lysed with sonication. MBP-tagged protein was bound to amylose beads (NEB) and eluted with buffer containing 20 mM HEPES pH7.5, 500 mM NaCl, and 10 mM maltose. Eluted proteins were incubated with TEV protease overnight to cleave off the His-MBP tag, concentrated, and then further purified on a sephacryl S300 column. Cascade containing fractions were pooled, dialyzed into 20 mM HEPES pH7.5, 150 mM NaCl, concentrated, filter sterilized, aliquoted, and frozen in liquid nitrogen.

Method 2: The two plasmids expressing cas5-cas8c-cas7-NLS-6×His and CRISPR were co-transformed into BL21(DE3) cells. The resulting strain was then inoculated into 10 mL of LB with 50 µg/mL of kanamycin and 20 µg/ml of chloramphenicol, and grown overnight at 37° C. This overnight culture was then used to inoculate a 1 L LB containing 50 µg/mL kanamycin, 20 µg/mL chloramphenicol. The big culture was cooled to 18° C. when it reached OD600 ~0.6 and induced with 1 mM IPTG for 18 hr at 18° C. Cells were then pelleted and resuspended in 30 mM HEPES pH 7.5, 500 mM NaCl and 0.5 mM TCEP, and then lysed with sonication. His-tagged protein was bound to Ni-NTA resin (Qiagen) and eluted with buffer containing 30 mM HEPES pH7.5, 500 mM NaCl, and 300 mM imidazole. Eluted proteins were concentrated, and then further purified on a sephacryl S300 column using 30 mM HEPES pH 7.5, 150 mM NaCl and 0.5 mM DTT as elution buffer. Cascade containing fractions were pooled, concentrated, filter sterilized, aliquoted, and frozen in liquid nitrogen.

In Vitro Transcription of Nla Cas3 mRNA

Nla cas3 mRNA was generated by in vitro transcription using MMESSAGE MMACHINE™ T7 Ultra kit (ThermoFisher Scientific, Waltham, MA) following the manufacture's protocol. Template for in vitro transcription was generated via PCR amplification using human codon optimized cas3-NLS as a template and a forward primer containing T7 promoter sequence.

Purification of NlaCas3

The plasmid expressing Nla cas3-NLS-6×His was transformed into BL21(DE3) cells. The resulting strain was then inoculated into 10 mL of LB with 50 µg/mL of kanamycin and grown overnight at 37° C. This overnight culture was then used to inoculate a 1 L LB containing 50 µg/mL kanamycin. The big culture was cooled to 18° C. when it reached OD600 ~0.6 and induced with 1 mM IPTG for 18 hr at 18° C. Cells were then pelleted and resuspended in 30 mM HEPES pH 7.5, 500 mM NaCl and 0.5 mM TCEP, and then lysed with sonication. His-tagged protein was bound to Ni-NTA resin (Qiagen) and eluted with buffer containing 30 mM HEPES pH7.5, 500 mM NaCl, and 300 mM imidazole. Eluted proteins were concentrated, and then further purified on a sephacryl S300 column using 30 mM HEPES pH 7.5, 150 mM NaCl and 0.5 mM DTT as elution buffer. Cas3 containing fractions were pooled, concentrated, filter sterilized, aliquoted, and frozen in liquid nitrogen.

RNP/mRNA Delivery into HAP1 Reporter Cell by Electroporation

The HAP1-AAVS1-EGFP reporter cells were electroporated using Neon Transfection system (ThermoFisher Scientific, Waltham, MA) according to the manufacturer's instruction. Briefly, the cells were individualized with TrypLE Express (Gibco), washed once with IMDM, 10% FBS and resuspended in Neon buffer R to a concentration of $2 \times 10^7$ cells/mL. 36 pmoles of NLS-Nla Cascade with or without 500 ng of NLS-NlaCas3 mRNA were mixed with approximately $10^5$ cells in buffer R in a total volume of 10 µL. Each mixture was then electroporated with a 10 µL Neon tip (1575V, 10 ms, 3 pulses) and plated in 24-well tissue culture plates containing 500 µL IMDM, 10% FBS. Cells were analyzed by flow cytometry four days after electroporation.

6-TG Selection Assay

HAP1 cells were individualized by TrypLE Express 2 days after RNP electroporation and then seeded in 6-well plate at a density of 200 cells/well. Two days after cell seeding, 6-TG (6-Thioguanine, Sigma) were added to each well at a final concentration of 15 µM. Media containing 6-TG was changed every 2 days. 6 days after 6-TG treatment, cells were fixed with ice-cold 90% methanol for 30 min, washed once with 1×PBS, stained with 0.5% crystal violet at RT for 5 min and destained with water. The plates are then air-dried at RT overnight and imaged by ChemiDoc MP imaging system (BioRad). The surviving colony numbers were then counted by OpenCFU (Geissmann, 2013).

DNA Lesion Analysis by Long-Range PCR and Cloning

Genomic DNAs of sorted EGFP negative cells were isolated using Gentra Puregene Cell Kit (Qiagen) per the manufacturer's instructions. Long-range PCRs were done using Q5 DNA Polymerase (NEB). Products were resolved on 1% agarose gel stained by SYBR Safe (Invitrogen) and visualized with Chemidoc MP imager (Biorad).

To define lesion junctions, the PCR reactions were purified using QIAquick PCR Purification Kit (Qiagen), and cloned into PCR-BluntII-TOPO vector (Invitrogen). Colony PCRs with M13 forward and reverse primers were carried out from the resulting colonies. Positive clones were randomly selected for Sanger sequencing (Eurofin) using an EGFP reverse primer.

Example 1

This example describes the informatic prediction of the protospacer adjacent motif (PAM) of *Neisseria lactamica*.

The native CRISPR array of *Neisseria lactamica* ATCC 23970 strain contains 30 spacers. FIG. 1A is a schematic diagram of the essential components of the type I-C CRISPR system encoded on the genome of *Neisseria lactamica* ATCC 23970.

It consists of a CRISPR array and seven cas genes, including the spacer acquisition genes cas1, cas2, and cas4, the nuclease-helicase gene cas3, and the set of genes (cas5, cas8 and cas7) encoding protein subunits of Cascade (FIG. 6A). The native CRISPR array contains thirty spacers 34-35 bp in length, sandwiched between 32-bp repeats.

CRISPRTarget (Biswas et al., *RNA Biol.,* 10(5): 817-827 (2013)) was used to bioinformatically search for natural target sequences for all these spacers. Seven out of the 30 spacers have natural targets identified in the Genbank-Phage, RefSeq-Plasmid, and IMGVR databases, with a score threshold of 27. A total of 28 unique targets were found. For these targets, the spacer-matched sequences were extracted together with 8 nucleotide flanking regions on both 5'- and 3'-sides, and were aligned using WebLogo (Crooks et al., *Genome Res.,* 14(6): 1188-90 (2004)). A conserved 5' flanking TTC PAM motif was deduced, as shown in FIG. 1B and FIG. 6B.

Example 2

This example describes a CRISPR DNA interference assay performed in *E. coli*.

Nla type I-C cas3, cascade, and crRNA plasmids (FIG. 2A) were co-transformed to BL21-AI cells. The resulting strain was made competent using the Mix and Go kit (Zymo Research), and then transformed with a target-containing pCDF1 plasmid to obtain the *E. coli* strain harboring all four plasmids. For the interference assay, a single colony of this final *E. coli* strain was inoculated into 2 mL LB culture with four antibiotics (kanamycin, carbenicillin, streptomycin, and chloramphenicol, selective for all plasmids) and grown to OD600 0.3 at 37° C. The culture was then pelleted, resuspended in LB with three antibiotics (Kan, Carb, and Cm), and then split in two halves. One was induced with 0.2% L-arabinose and 1 mM IPTG. Both the induced and un-induced cultures were grown for an additional 3 hours at 37° C. Cultures were then serially diluted 10-fold and plated onto LB plates containing quadruple vs. triple antibiotics (lacking spectinomycin). The ratio of colony forming units between the two plates represents the efficiency of CRISPR interference. The interference assay is schematically illustrated in FIG. 2B.

FIG. 2C shows that the Nla I-C system enables a robust CRISPR interference phenotype. Upon induction, a matching target with a 5'-TTC PAM resulted in a dramatic reduction in colony counts, in comparison to a non-matched target. FIG. 2D shows that DNA interference by type I-C CRISPR-Cas is dependent on a functional PAM. Targets with both 5'-TTC and 5'-TTT PAM can support CRISPR interference, while a 5'-AAG motif cannot. FIG. 2E shows that DNA interference requires the nuclease activity of Cas3. The nuclease active site mutation D53A in Cas3 abolishes interference activity.

Example 3

This example demonstrates that *N. lactamica* type I-C CRISPR-Cas enables long-range genome editing in human cells.

FIG. 3A shows the plasmid design for expressing Nla type I-C CRISPR-Cas components in human cells. Human codon optimized cas3, cas5, cas8c, and cas7 sequences were expressed from EF1a promoters, and each sequence included an attached nuclear localization signal (NLS) and HA tag. CRISPR RNA expression was driven from a U6 promoter. The CRISPR array contains three repeats and two identical spacers. FIG. 3B is a schematic diagram of the targeted genomic locus in HAP1-AAVS1-EGFP reporter cell line. Successful targeting by the Nla I-C CRISPR system should lead to GFP negative cells. Flow cytometry analysis of the HAP1-AAVS1-EGFP cells was performed before (FIG. 3C) and after (FIG. 3D) editing by Nla I-C CRISPR-Cas. Editing of EGFP led to a significantly higher level of GFP negative cells in FIG. 3D (2.6%) than the background control (0.2%) shown in FIG. 3C. PCR analysis of DNA deletions induced by Nla I-C CRISPR was performed. In this regard, genomic DNA isolated from edited and FACS-sorted, EGFP-negative cell population was subjected to long-range PCRs. The PCR primer pairs used are indicated by their annealing sites shown in FIG. 3F. For these three pairs of primers, the full-length PCR products produced from unedited genomic DNA were expected to be 4.6 kb, 15.7 kb, and 20 kb, respectively. The appearance of multiple smaller PCR bands indicated heterogenous large deletions created upstream of the targeted site in EGFP. Cloning and Sanger sequencing of the PCR products revealed the boundary of unique deletion events on the genome, as shown in FIG. 3F.

DNA deletions created by Nla I-C CRISPR were heterogenous, unidirectional, and long-range (up to 20 kb).

Example 4

This example demonstrates that ribonucleoprotein (RNP) delivery of Nla I-C CRISPR-Cas enables highly efficient genome editing in human cells.

Plasmids used to express and purify the NLS-Cascade from *E. coli* BL21 (DE3) cells are shown in FIG. 4A. Cas5 was fused to an His-MBP tag for purification purposes, which was later removed by TEV cleavage. Cas7 was NLS-tagged. The CRISPR array contains three repeats and two identical spacers targeting the EGFP site shown in FIG. 3B. The purified Cascade complex was analyzed by SDS-PAGE followed by Coomassie-staining. The protein purification procedure included steps of MBP pull-down, TEV cleavage, and size exclusion chromatography (FIG. 4B). Flow cytometry analysis was performed on HAP1-AAVS1-EGFP reporter cells that were either unedited (FIG. 4C), or electroporated with EGFP-targeting Cascade RNP without (FIG. 4D) or with (FIG. 4E) mRNA encoding cas3.

Co-delivery of Cascade RNP and cas3 mRNA resulted in highly robust editing efficiency (96%).

Example 5

This example demonstrates that Nla type I-C CRISPR-Cas enables homology directed repair (HDR) in human cells.

FIG. 5A schematically illustrates the targeted AAVS1-EF1α-EGFP locus (top) and the HDR donor plasmid used (middle). The HDR donor DNA template contains a truncated, non-functional BFP fragment and an EF1α promoter. There is a 2 nucleotide (nt) sequence difference between the ORFs of EGFP and BFP (indicated with a * in FIG. 5). Upon successful HDR, the 2 nt changes should convert AAVS1-EF1α-EGFP to AAVS1-EF1α-BFP (FIG. 5A, bottom panel).

Flow cytometry analysis was performed on the HAP1-AAVS1-EGFP reporter cells that were un-edited (FIG. 5B), or transfected with CRISPR-Cas plasmids without (FIG. 5C) or with (FIG. 5D) the HDR donor template. Co-delivery of the Nla type I-C CRISPR-Cas plasmids along with the HDR donor template resulted in elevated level of BFP positive cells, indicating successful HDR events.

Example 6

This example describes a CRISPR DNA interference assay performed in *E. coli*.

The functionality of this Nla I-C CRISPR system was tested by conducting a plasmid interference assay using *E. coli* as a surrogate host (FIG. 6C). The cas5-8-7-4 operon was cloned into pBAD vector under the control of an arabinose inducible promoter, cas3 into pET28b under a T7 promoter, the native CRISPR into pACYC under a T7 promoter and the potential target sequences into pCDF1. BL21-AI derivative strains harboring all four plasmids were built and the induced culture was plated on quadruple antibiotics LB plates to track cell survival. Induction of crispr-cas expression led to ~1,000-fold reduction in colony counts, if the target plasmid contained a 5'-TTC PAM followed by sequence complementary to any of the first three native CRISPR spacers, but not when an empty target plasmid was used as negative control (FIGS. 6D-6E). This result indicated a robust plasmid interference phenotype in vivo. A control target for spacer 1 with a 5'-AAG motif failed to elicit interference, suggesting that a functional PAM is a prerequisite for Nla I-C system to mount successful CRISPR defense (FIG. 6E).

To determine the other components facilitating the interference, a series of deletion mutants, each lacking a different crispr-cas gene, were analyzed (FIG. 6F). Interference was completely abrogated by internal deletion of cas7, cas8, or cas5, but not the cas4 gene, from the pCascade plasmid; strains lacking cas3 or the CRISPR array were also defective for interference (FIG. 6G). Collectively, the results showed that DNA targeting by Nla I-C CRISPR utilized a matching spacer-target pair, a functional PAM, cas3 and all Cascade subunit genes, whereas the putative spacer acquisition genes cas1, cas2 and cas4 were dispensable.

Example 7

This example describes high efficiency multiplexed genome engineering in human cells.

RNP-based genome editing was tested by purifying recombinant Cas3 and Cascade separately from *E. coli* (FIG. 7A), delivering them into various human cell lines via electroporation, and monitoring genome editing efficiency by flow cytometry. Initial editing experiments were carried out in a human embryonic stem cell (hESC) dual reporter line, with two CRISPR guides designed to target 5'-TTC-flanked sites in the EGFP or tdTomato (tdTm) genes respectively (FIG. 7B). The corresponding Cascade complexes containing nuclear localization signal (NLS) sequences on the C-termini of all Cas7 subunits were purified via nickel affinity pulldown and size exclusion chromatography (SEC), and then tested with or without purified NLS-Cas3. Roughly 50% and 30% editing rates were observed for EGFP and tdTm, respectively, when the cognate Cascade was used in conjunction with Cas3 (FIGS. 7C-7D). Negative controls lacking Cas3, or containing a Cascade targeting either the other non-corresponding reporter gene or an endogenous genomic locus (non-targeting, NT) all failed to produce a signal above the untreated background (FIGS. 7C-7D). The 30-50% editing efficiency obtained in hESC was quite impressive, given that prior work utilizing T *fusca* Type I-E RNP only gave up to 13% editing in the same reporter cell.

Parallel experiments were performed in a HAP1 reporter cell line using the same EGFP-targeting Cascade, and dose-dependent editing of up to 83% was obtained. As the amount of Cascade used went up from 4.5 to 35 pmol, editing efficiency gradually increased from 27% to 83% (FIGS. 9A and 9C). In contrast, for Cas3 titration editing jumped to and plateaued at ~76% with as little as 3 pmol Cas3 delivered (FIGS. 9B and 9D). Genome editing with the current Nla CRISPR-Cas3 RNP platform was limited by the assembly or target searching activity of Cascade, but not the DNA degradation activity of Cas3.

The CRISPR array of a Type I system is transcribed into a multi-unit primary transcript, which is then processed into individual mature crRNAs loaded in Cascade. The multi-spacer CRISPR cassette therefore offers a unique opportunity to co-express numerous guide RNAs and purify a collection of corresponding Cascade RNPs at once from *E. coli*. To explore this, two versions of the CRISPR in R-S-R-S-R configuration were created, each contained three repeats and two distinct intervening spacers at different relative positions (FIG. 7E, samples 4-5). When each resulting Cascade prep was electroporated with Cas3 into HAP1 reporter cell, concurrent disruption of both EGFP and tdTm fluorescence was observed in majority of the cells (FIG. 7E, 47% and 43% for the two arrays, respectively, and FIG. 10A), indicative of efficient multiplexed editing. Importantly, flow cytometry showed that multiplexing indeed occurred in individual human cell, not just on a population level. As controls, Cascade RNPs purified using arrays with two identical spacers targeting one reporter led to >85% editing of just the cognate fluorescent gene but not the other non-cognate one (FIG. 7E, samples 2-3).

The NlaCRISPR-Cas3 RNP was applied to target various endogenous genes in different human cell lines. The HPRT1 locus of the near-haploid HAP1 cells was used, because its editing rate can be readily assessed using a single clone cytotoxicity assay measuring resistance to 6-thioguanine (6-TG) mediated cell killing. Cascade RNP targeting the promoter region 489 bp or 274 bp upstream of the ATG start codon of HPRT1 gene was electroporated into wild-type (wt) HAP1 cells, and led to Cas3-dependent editing of 78% and 34%, respectively (FIGS. 7F-7H). The same HPRT-G1 guide also caused robust DNA targeting in hESCs, HEK293T, and HeLa cells, as evidenced by the smaller-than-wt products in the long-range genomic PCR analysis (FIG. 10B). Moreover, Cascade was successfully reprogrammed to edit another endogenous gene CCR5 in HAP1 cells (FIG. 10C). Altogether, the data established Nla CRISPR-Cas3 as a compact type I-C system repurposed for high-efficiency genome engineering in human cells.

Example 8

This example describes that *N. lactamica* type I-C CRISPR-Cas enables large unidirectional genome deletions in human cells.

Without making presumption about the directionality or size range of the NlaCas3-induced lesions, three different sets of PCRs were performed using genomic DNA extracted from HAP1 cells edited by Cascade-HPRT-G1 and Cas3 from FIG. 7H. First, to specifically amplify regions downstream of CRISPR-programmed site, a fixed forward primer G annealing 100 bp upstream of target site was used, and it was paired with tiling reverse primers B through F about 2.8-19 kb downstream of target (FIG. 8A). Each PCR amplification gave rise to a collection of bands of varying sizes but all smaller than the corresponding full-length product (FIG. 8B, lanes 6-10), indicative of heterogenous large deletions firing downstream in the PAM-proximal direction. The control genomic DNA from untreated cells failed to give any product (FIG. 8B, lanes 1-5), likely due to a GC-rich region in exon 1 that prevented PCR amplification.

To precisely define the boundaries of these NlaCas3-mediated deletions, the PCR products from lanes 6-10 of FIG. 8B were pooled, TOPO-cloned, and 34 independent clones were randomly selected for Sanger sequencing. A total of 31 unique lesions was identified, and the overall pattern was similar to that exhibited by Tfu type I-E Cascade-Cas3. The onset of deletions was not uniformly at the presumed R-loop but instead was clustered in a window ~15-150 nt downstream, while the deletion endpoints were distributed across the ~20 kb PAM-proximal genomic region analyzed (FIG. 8C), highlighting the heterogenous nature of the large deletions caused by NlaCas3. Furthermore, vast majority of the resulting chromosomal junctions have the 5' and 3' sequences flanking the deletion rejoined seamlessly, presumably by end-joining DNA repair pathways in human cells (FIG. 8C).

Then, the converse PCR experiment was conducted to amplify regions upstream of the CRISPR-targeted site, using a fixed reverse primer A annealing 0.25 kb downstream of the target, in conjunction with serial forward primers H through L about 0.8-6.4 kb upstream of target (FIG. 8A). No obvious large deletions were detected, as the anticipated full-length bands from both edited and untreated cells were observed (FIG. 8D). This observation suggested that there are very few, if any, NlaCas3-induced deletions firing upstream towards the PAM-distal direction. Collectively, the Nla I-C and Tfu I-E systems likely use similar mechanisms for processive DNA degradation by Cas3 and subsequent DNA repair by endogenous machinery of human cells.

In the last set of long-range PCRs, serial forward primers G through J were paired with a common reverse primer D annealing 7.1 kb downstream of target (FIG. 8A), and a spectrum of amplicons containing large deletions were detected (FIG. 8E, lanes 25-28). Of note, the size of the smallest amplicon in each reaction was larger than the genomic distance between CRISPR target site and the annealing position of the forward primer used, implying that very few bi-directional large deletions existed that span both PAM-proximal and PAM-distal regions of the target.

In addition, similar long-range PCR results were observed for RNP editing experiments performed on the same HPRT1 target in hESCs and HEK293T cells (FIG. 11), as well as on the DNMT3b-GFP target in hESCs (FIG. 12), although in the latter experiment a few bi-directional lesions were also detected (FIG. 12D-12E). Taken together, Nla CRISPR-Cas3 created a spectrum of large, unidirectional deletions originating from the target site in human cells.

---

SEQUENCES

```
Nla-cas3 (SEQ ID NO: 1)
GTGAATTTCGACTATATAGCCCACGCTCGCCAAGACTCATCAAAAAATTGGCATTCC
CATCCCCTGCAAAAACATCTACAAAAAGTCGCCCAACTCGCCAAGCGTTTTGCAGG
GCGTTATGGGTCGTTGTTTGCCGAATATGCGGGGCTTTTGCACGATTTGGGGAAATT
TCAGGAATCTTTTCAGAAATATATCCGTAATGCATCCGGCTTTGAAAAAGAAAATGC
CCATTTGGAAGATGTCGAATCTACCAAGTTGCGCAAAATTCCGCATTCCACTGCCGG
TGCCAAATATGCGGTAGAACGTCTAAATCCATTTTTCGGGCATTTGCTGGCATATTT
GATTGCCGGGCATCATGCTGGGCTGGCAGATTGGTATGACAAAGGCAGCCTGAAAC
GCCGTCTGCAACAGGCGGATGACGAGTTGGCAGCGTCTTTGTCGGGCTTTGTGGAAA
GTAGTTTGCCCGAAGATTTTTTCCCGTTATCAGATGATGACTTGATGCGGGATTTTTT
TGCGTTTTGGGAAGACGGGGCAAAGCTGGAAGAATTGCATATTTGGATGCGTTTTCT
CTTTTCCTGCTTGGTGGATGCCGATTTTTTGGATACCGAAGCCTTTATGAACGGCTAT
GCCGATGCAGATACTGCGCAGGCTGCCGGATTGCGCCCAAAATTTCCCGGTTTGGAT
GAGTTACACCGGCGATATGAGCAATATATGGCGCAACTTTCAGAAAAAGCAGATAA
AAATTCATCTTTAAACCAAGAACGCCACGCCATTTTGCAGCAATGTTTTTCTGCCGC
AGAAACGGACCGTACTTTGTTTTCTTTAACCGTGCCGACCGGTGGCGGTAAAACTTT
GGCGAGCTTGGGCTTCGCTTTGAAGCACGCGCTGAAATTTGGCAAAAAACGTATTAT
CTATGCTATTCCTTTCACCAGTATTATCGAGCAGAATGCCAATGTTTTCCGCAATGCA
TTAGGCGATGATGTGGTTTTAGAACACCACAGCAATTTGGAAGTGAAAGAAGATAA
GGAAACAGCGAAAACTCGTCTTGCTACGGAAAATTGGGACGCGCCGCTGATTGTTA
CTACCAATGTGCAACTGTTTGAAAGCCTGTTTGCGGCGAAAACCAGCCGTTGCCGCA
AGATTCACAATATTGCCGACAGCGTGGTGATTTTGGATGAAGCCCAGCAGCTTCCGC
GCGATTTCCAAAAACCGATTACCGACATGATGCGGGTGCTGGCGCGTGATTACGGC
GTTACCTTTGTGCTGTGCACGGCAACCCAACCGGAGCTTGGCAAAAATATCGACGCA
TTCGGTCGCACTATTTTGGAAGGGCTACCAGATGTGCGCGAAATTGTGGCAGACAAA
ATTGCCTTATCGGAAAAACTGCGCCGCGTCCGCATCAAAATGCCGCCGCCAAACGG
CGAAACGCAAAGCTGGCAGAAAATTGCCGATGAAATAGCCGCGCGCCCGTGTGTTT
TGGCAGTGGTCAATACGCGAAAACACGCCCAAAAACTCTTTGCCGCCCTGCCTTCTA
ACGGAATCAAGCTACATTTATCTGCCAATATGTGCGCCACACACTGCAGCGAAGTGA
TTGCGTTGGTTCGCCGATATTTGGCACTGTATCGCGCAGGCAGCCTGCACAAGCCCT
TGTGGCTGGTCAGCACGCAGTTGATTGAAGCAGGCGTGGATTTGGATTTCCCTTGCG
TGTATCGGGCGATGGCAGGGCTGGACAGCATTGCCCAGGCGGCGGGACGGTGCAAC
CGTGAAGGTAAACTGCCGCAGTTGGGCGAAGTAGTCGTATTCCGCGCCGAAGAAGG
CGCGCCCAGCGGCAGCCTGAAACAGGGGCAGGACATTACCGAAGAGATGCTGAAA
GCAGGGCTGCTTGATGACCCGCTTTCCCCGTTGGCATTTGCCGAATATTTCCGCCGAT
```

-continued

---

SEQUENCES

---

TCAACGGCAAAGGTGATGTGGACAAACACGGTATCACAACGCTTTTGACGGCAGAA
GCATCAAATGAAAATCCGCTGGCAATTAAATTCCGCACAGCTGCCGAACGTTTCCAC
CTGATTGATAACCAAGGCGTGGCACTCATTGTGCCGTTTATCCGTTGGCTCATTGG
GAAAAAGACGGCAGTCCGCAAATCGTCGAAGCAAACGAGCTGGACGATTTTTTCAG
ACGACATCTAGATGGTGTTGAAGTTTCAGAATGGCAGGATATTTTGGACAAACAAC
GCTTTCCGCAGCCGCCAGACAACTCCTTTGGGCAAACCGATCAACCACTGCTGCCCG
AGCCGTTTGAAAGCTGGTTCGGTCTGTTGGAAAGCGACCCGCTCAAACACAAATGG
GTTTACCGCAAGCTGCAACGCTACACGATTACTGTGTACAACACGAACTGAAAAA
GTTGCCTGAACATGCCGTTTTTTCAAGAGCGGGATTGCTCGTGTTAGATAAGGGCTA
TTACAAAGCCGTGCTTGGCGCGGATTTTGACGATGCGGCTTGGCTACCTGAAAATTC
GGTTTTATGA

Nla-Cas3 protein sequence (SEQ ID NO: 85)
MNFDYIAHARQDSSKNWHSHPLQKHLQKVAQLAKRFAGRYGSLFAEYAGLLHDLGKF
QESFQKYIRNASGFEKENAHLEDVESTKLRKIPHSTAGAKYAVERLNPFFGHLLAYLIAG
HHAGLADWYDKGSLKRRLQQADDELAASLSGFVESSLPEDFFPLSDDDLMRDFFAFWE
DGAKLEELHIWMRFLFSCLVDADFLDTEAFMNGYADADTAQAAGLRPKFPGLDELHRR
YEQYMAQLSEKADKNSSLNQERHAILQQCFSAAETDRTLFSLTVPTGGGKTLASLGFAL
KHALKFGKKRIIYAIPFTSIIEQNANVFRNALGDDVVLEHHSNLEVKEDKETAKTRLATE
NWDAPLIVTTNVQLFESLFAAKTSRCRKIHNIADSVVILDEAQQLPRDFQKPITDMMRVL
ARDYGVTFVLCTATQPELGKNIDAFGRTILEGLPDVREIVADKIALSEKLRRVRIKMPPP
NGETQSWQKIADEIAARPCVLAVVNTRKHAQKLFAALPSNGIKLHLSANMCATHCSEVI
ALVRRYLALYRAGSLHKPLWLVSTQLIEAGVDLDFPCVYRAMAGLDSIAQAAGRCNRE
GKLPQLGEVVVFRAEEGAPSGSLKQGQDITEEMLKAGLLDDPLSPLAFAEYFRRFNGKG
DVDKHGITTLLTAEASNENPLAIKFRTAAERFHLIDNQGVALIVPFIPLAHWEKDGSPQIV
EANELDDFFRRHLDGVEVSEWQDILDKQRFPQPPDNSFGQTDQPLLPEPFESWFGLLESD
PLKHKWVYRKLQRYTITVYEHELKKLPEHAVFSRAGLLVLDKGYYKAVLGADFDDAA
WLPENSVL Nla-cas5 (SEQ ID NO: 2)
ATGAGGTTCATCCTGGAAATCAGTGGTGATTTGGCATGCTTCACAAGGTCTGAGCTA
AAGGTGGAAAGGGTTAGTTATCCTGTGATAACGCCGTCTGCCGCCAGGAACATCCTA
ATGGCGATATTGTGGAAGCCGGCGATTCGCTGGAAGGTCTTGAAGATAGAAATCCT
AAAACCGATTCAGTGGACGAATATCCGCCGCAACGAAGTGGGAACTAAGATGAGTG
AGCGTAGCGGCTCGCTCTATATTGAAGATAACCGCCAGCAGCGCGCATCCATGCTGC
TGAAAGACGTTGCCTACCGCATTCACGCCGATTTTGACATGACCAGTGAAGCGGGCG
AGAGCGACAACTATGTTAAATTTGCCGAAATGTTCAAGCGGCGGGCAAAGAAAGGA
CAATATTTCCACCAACCTTATTTAGGCTGTCGTGAGTTTCCTTGTGATTTCAGGTTGC
TGGAAAAAGCCGAAGATGGATTGCCACTCGAAGACATTACCCAAGATTTCGGTTTTA
TGCTGTATGACATGGATTTCAGCAAATCCGACCCGCGTGATTCCAATAACGCCGAGC
CGATGTTTTACCAATGCAAAGCGGTAAACGGCGTGATTACCGTGCCGCCTGCCGACA
GCGAGGAGGTGAAACGATGA Nla-Cas5 protein sequence (SEQ ID NO: 86)
MRFILEISGDLACFTRSELKVERVSYPVITPSAARNILMAILWKPAIRWKVLKIEILKPIQW
TNIRRNEVGTKMSERSGSLYIEDNRQQRASMLLKDVAYRIHADFDMTSEAGESDNYVK
FAEMFKRRAKKGQYFHQPYLGCREFPCDFRLLEKAEDGLPLEDITQDFGFMLYDMDFS
KSDPRDSNNAEPMFYQCKAVNGVITVPPADSEEVKR Nla-cas8c (SEQ ID NO: 3)
ATGATTTTGCACGCGCTCACCCAATACTATCAACGCAAAGCCGAAAGTGATGGCGGT
ATTGCCCAGGAAGGGTTTGAAAACAAAGAAATACCGTTCATTATCGTTATAGACAA
ACAGGGTAATTTTATTCAGCTGGAAGATACCCGTGAGCTGAAAGTTAAGAAGAAAG
TTGGCCGCACTTTTTTAGTACCGAAAGGTTTGGGCAGGAGCGGTTCAAATCCTACG
AAGTAAGCAATTTATTGTGGGATCACTACGGTTATGTACTTGCTTATGCCGGAGAAA
AAGGGCAGGAGCAGGCGGACAAACAGCATGCCAGCTTTACCGCCAAAGTAAATGA
ATTGAAACAGGCGCTGCCCGATGATGCAGGTGTTACTGCGGTTGCTGCCTTTTTGTC
TTCTGCGGAAGAAAAAGCAAAGTCATGCAGGCTGCAAATTGGGCGGAGTGTGCCA
AAGTCAAAGGCTGTAATCTCAGCTTCCGCCTGGTGGATGAAGCGGTAGATTGGTTT
GCCAGTCAAAGGCGGTGCGGGAATATGTGAGTCAAGCAAATCAAACGCAATCCGAT
AATGTCCAAAAAGGCATTTGCCTGGTAACGGGCAAAGCTGCGCCGATTGCGCGGCT
GCATAACGCCGTGAAAGGCGTGAATGCCAAGCCCGCCCCGTTTGCATCGGTAAATC
TGTCGGCTTTTGAATCATACGGCAAAGAGCAGGGCTTTATCTTTCCCGTGGGCGAGC
AAGCCATGTTCGAATATACCACCGCCTTGAACACCTTGCTTGCTAGCGAAACCGAT
TCCGTATCGGCGATGTAACGGCCGTATGTTGGGGCGCGAAACGGACTCCGTTGGAG
GAAAGTCTTGCTTCGATGATTAACGGCGGCGGCAAAGACAACCCGATGAGCATAT
CGATGCCGTTAAAACTCTTTATAAAAGCCTATACAACGGTCAATACCAAAAACCTGA
CGGCAAAGAAAAATTCTACCTTTTAGGTTTATCGCCCAATTCCGCGCGCATTGTCGT
CCGCTTTTGGCATGAAACCACCGTTGCCGCCTTATCAGAAAGTATTGCGGCGTGGTA
TGACGATTTGCAAATGGTGCGCGGCGAAAACTCGCCATACCCCGAATATATGCCGCT
ACCGCGCCTGCTGGGTAATTTGGTGTTGGACGGCAAAATGGAAAACCTGCCATCTGA
CCTGATTGCCCAAATAACCGATGCCGCGCTCAACAACCGTGTTTTACCCGTCAGCCT
GTTGCAGGCTGCTTTGCGGCGCAACAAGGCGGAACAGAAAATTACCTATGGCAGAG
CAAGTCTGCTTAAAGCCTATATCAATCGCGCAATCCGTGCGGGTCGTCTGAAAAACA
TGAAGGAGCTAACTATGGGCCTAGATAGAAACCGTCAAGACATCGGCTATGTGCTG
GGGCGGCTGTTTGCCGTGCTGGAAAAAATACAAGCCGAGGCCAATCCCGGCTTGAA
CGCCACCATTGCCGACCGCTATTTCGGTTCGGCAAGCAGCACACCGATTGCCGTATT

SEQUENCES

```
CGGCACACTGATGCGCTTGTTGCCGCACCATTTGAACAAACTGGAATTTGAAGGACG
TGCCGTACAACTGCAATGGGAAATCCGCCAGATTTTGGAACATTGTCAGAGATTTCC
TAACCATTTGAATTTGGAACAGCAAGGCCTATTTGCCATCGGTTACTACCACGAAAC
CCAATTCCTGTTTACCAAAGACGCATTGAAAAACCTGTTCAACGAAGCGAAAACCG
CATAA

Nla-Cas8 protein sequence (SEQ ID NO: 87)
MILHALTQYYQRKAESDGGIAQEGFENKEIPFIIVIDKQGNFIQLEDTRELKVKKKVGRTF
LVPKGLGRSGSKSYEVSNLLWDHYGYVLAYAGEKGQEQADKQHASFTAKVNELKQAL
PDDAGVTAVAAFLSSAEEKSKVMQAANWAECAKVKGCNLSFRLVDEAVDLVCQSKA
VREYVSQANQTQSDNVQKGICLVTGKAAPIARLHNAVKGVNAKPAPFASVNLSAFESY
GKEQGFIFPVGEQAMFEYTTALNTLLASENRFRIGDVTAVCWGAKRTPLEESLASMING
GGKDKPDEHIDAVKTLYKSLYNGQYQKPDGKEKFYLLGLSPNSARIVVRFWHETTVAA
LSESIAAWYDDLQMVRGENSPYPEYMPLPRLLGNLVLDGKMENLPSDLIAQITDAALNN
RVLPVSLLQAALRRNKAEQKITYGRASLLKAYINRAIRAGRLKNMKELTMGLDRNRQDI
GYVLGRLFAVLEKIQAEANPGLNATIADRYFGSASSTPIAVFGTLMRLLPHHLNKLEFEG
RAVQLQWEIRQILEHCQRFPNHLNLEQQGLFAIGYYHETQFLFTKDALKNLFNEAKTA Nla-cas7 (SEQ ID NO: 4)
ATGACTATTGAAAAACGCTACGACTTTGTCTTTTTATTTGATGTGCAAGACGGCAAT
CCCAACGGCGATCCTGACGCAGGTAACCTGCCGCGTATCGACCCGCAAACCGGCGA
AGGTTTGGTAACTGATGTTTGCCTGAAACGCAAAGTCCGCAACTTTATCCAAATGAC
TCAAAATGACGAACATCACGACATCTTTATCCGCGAAAAAGGCATTTTGAACAACCT
GATTGACGAAGCCCACGAGCAGGAAAACGTAAAAGGCAAAGAAAAAGGCGAGAAA
ACCGAAGCTGCCCGCCAATACATGTGCAGCCGTTATTACGACATCCGCACATTTGGC
GCAGTGATGACTACCGGCAAAAATGCAGGACAAGTACGCGGTCCCGTGCAACTGAC
TTTTTCTCGCTCTATTGATCCCATCATGACCTTGGAACACAGCATTACCCGCATGGCG
GTTACCAACGAAAAAGATGCCAGTGAAACCGGCGACAACCGTACAATGGGTCGCAA
ATTCACCGTCCCCTACGGTCTATACCGCTGCCATGGCTTCATTTCTACCCATTTTGCC
AAACAAACAGGCTTTTCCGAAAACGATTTAGAGCTGTTTTGGCAGGCACTTGTCAAT
ATGTTTGACCACGACCATTCCGCCGCACGCGGACAAATGAACGCACGCGGGCTCTA
TGTGTTTGAACACAGCAATAATCTAGGTGATGCGCCTGCTGATAGTCTGTTCAAACG
CATTCAGGTAGTCAAAAAGGACGGTGTAGAAGTAGTAAGGAGTTTTGACGATTATC
TTGTCAGCGTAGACGATAAGAATCTTGAAGAAACCAAGCTGTTGCGTAAATTAGGC Nla-Cas7 protein sequence (SEQ ID NO: 88)
MTIEKRYDFVFLFDVQDGNPNGDPDAGNLPRIDPQTGEGLVTDVCLKRKVRNFIQMTQ
NDEHHDIFIREKGILNNLIDEAHEQENVKGKEKGEKTEAARQYMCSRYYDIRTFGAVMT
TGKNAGQVRGPVQLTFSRSIDPIMTLEHSITRMAVTNEKDASETGDNRTMGRKFTVPYG
LYRCHGFISTHFAKQTGFSENDLELFWQALVNMFDHDHSAARGQMNARGLYVFEHSN
NLGDAPADSLFKRIQVVKKDGVEVVRSFDDYLVSVDDKNLEETKLLRKLG Nla-CRISPR-repeat (SEQ ID NO: 5)
TCAGCCGCCTCTAGGCGGCTGTGTGTTGAAAC EGFP targeting guide sequence (SEQ ID NO: 6)
gagggcgacaccctggtgaaccgcatcgagctgaa tdTomato targeting guide sequence (SEQ ID NO: 89)
aagaccatctacatggccaagaagcccgtgcaact HPRT1 targeting guide sequence (SEQ ID NO: 90)
ctgactcttggcccagtgcttccccaaaccettaa CCR5 targeting guide sequence (SEQ ID NO: 91)
ttactgtccccttctgggctcactatgctgccgcc human codon optimized cas3 with NLS and HA tag (SEQ ID NO: 7)
ATGAACTTCGACTATATCGCCCACGCCAGACAGGACAGCAGCAAGAACTGGCACTC
TCACCCTCTGCAGAAACATCTGCAGAAGGTGGCCCAGCTGGCCAAGAGATTTGCCG
GCAGATACGGCAGCCTGTTCGCCGAATATGCCGGCCTGCTGCACGATCTGGGCAAG
TTCCAAGAGAGCTTCCAGAAGTACATCCGGAACGCCAGCGGCTTCGAGAAAGAGAA
TGCCCACCTGGAAGATGTGGAAAGCACCAAGCTGCGGAAGATCCCTCACTCTACAG
CCGGCGCTAAGTACGCCGTGGAAAGACTGAACCCCTTCTTCGGCCATCTGCTGGCCT
ATCTGATTGCCGGACATCATGCCGGACTGGCCGATTGGTACGATAAGGGCAGCCTG
AAGCGGAGACTGCAGCAAGCCGATGATGAACTGGCCGCCTCTCTGTCCGGCTTCGT
GGAATCTTCTCTGCCCGAGGACTTCTTCCCTCTGTCCGACGACGACCTGATGAGAGA
CTTCTTCGCCTTCTGGGAGGACGGCGCCAAGCTGGAAGAACTGCACATCTGGATGCG
GTTTCTGTTCAGCTGCCTGGTGGACGCCGACTTCCTGGATACCGAGGCCTTCATGAA
CGGCTACGCCGATGCCGATACAGCCCAAGCTGCTGGACTGAGGCCTAAGTTCCCTG
GCCTGGATGAGCTGCATCGGAGATACGAGCAGTACATGGCTCAGCTGTCCGAGAAG
GCCGACAAGAACAGCTCCCTGAATCAAGAGCGGCACGCCATCCTGCAGCAGTGCTT
TTCTGCCGCCGAGACAGACAGAACCCTGTTCAGCCTGACAGTGCCTACAGGCGGCG
GAAAAACTCTGGCCTCTCTGGGCTTTGCCCTGAAGCACGCCCTGAAGTTCGGCAAGA
AGCGGATCATCTACGCCATTCCTTTCACCAGCATCATCGAGCAGAACGCCAACGTGT
TCAGAAACGCCCTGGGCGACGATGTGGTGCTGGAACACCACAGCAACCTGGAAGTG
AAAGAGGACAAAGAGACAGCCAAGACCAGACTGGCCACCGAGAATTGGGATGCCC
```

| SEQUENCES |
| --- |

```
CTCTGATCGTGACCACCAACGTGCAGCTGTTCGAGAGCCTGTTTGCCGCCAAGACCT
CCAGATGCAGAAAGATCCACAATATCGCCGACAGCGTGGTCATCCTGGACGAAGCT
CAGCAGCTGCCCCGGGACTTCCAGAAACCTATCACCGATATGATGCGCGTGCTGGCC
AGAGACTACGGCGTGACCTTTGTGCTGTGTACCGCCACACAGCCTGAGCTGGGCAA
GAACATCGATGCCTTCGGCCGGACCATCCTGGAAGGATTGCCTGACGTGCGGGAAA
TCGTGGCCGATAAGATCGCCCTGAGCGAGAAGCTGAGAAGAGTGCGGATCAAGATG
CCTCCTCCAAACGGCGAGACACAGAGCTGGCAGAAGATCGCCGACGAGATCGCCGC
TAGACCATGTGTGCTGGCCGTGGTCAACACCAGAAAACACGCCCAGAAGCTGTTCG
CTGCCCTGCCTAGCAATGGCATCAAGCTGCACCTGAGCGCCAACATGTGCGCCACAC
ACTGCTCTGAAGTGATCGCCCTCGTGCGGAGATATCTGGCCCTGTACAGAGCCGGAA
GCCTGCACAAACCTCTGTGGCTGGTGTCTACCCAGCTGATTGAAGCTGGCGTGGACC
TGGACTTCCCCTGTGTGTATAGAGCCATGGCCGGCCTGGATTCTATTGCCCAAGCAG
CCGGACGGTGCAACAGAGAGGGAAAACTGCCTCAGCTGGGCGAAGTGGTGGTGTTC
AGAGCTGAAGAAGGCGCCCCTAGCGGCTCTCTGAAGCAAGGCCAGGATATCACCGA
GGAAATGCTGAAGGCCGGACTGCTGGACGACCCTTTGTCTCCTCTGGCCTTCGCCGA
GTACTTCAGACGGTTCAATGGCAAGGGCGACGTGGACAAGCACGGCATCACAACAC
TGCTGACAGCCGAGGCCAGCAACGAGAATCCACTGGCCATCAAGTTCCGGACCGCC
GCTGAGAGATTCCACCTGATCGATAATCAGGGCGTCGCACTGATCGTGCCCTTCATT
CCTCTGGCTCACTGGGAGAAAGACGGCAGCCCTCAGATCGTGGAAGCCAACGAGCT
GGACGATTTCTTCAGGCGGCACCTGGACGGCGTGGAAGTGTCTGAGTGGCAGGACA
TCCTGGATAAGCAGCGGTTCCCTCAGCCTCCTGACAACAGCTTTGGCCAGACCGATC
AGCCTCTGCTGCCTGAGCCTTTCGAGAGTTGGTTCGGCCTGCTCGAGAGCGACCCAC
TGAAGCACAAATGGGTGTACCGGAAGCTGCAGCGGTACACCATCACCGTGTATGAG
CACGAGCTGAAAAAGCTGCCCGAGCACGCCGTGTTCTCTAGAGCTGGACTGCTCGT
GCTGGACAAGGGCTACTATAAGGCCGTGCTGGGCGCCGATTTTTGACGATGCTGCTTG
GCTGCCAGAGAACTCTGTGCTGGGCTCTGTGGGCTACCCCTACGATGTGCCTGATTA
CGCCGGCAGCTACCCTGAGTTCCCCAAGAAAAAGCGGAAAGTGTGA human codon optimized cas5 with NLS and HA tag (SEQ ID NO: 8)
ATGCGGTTCATCCTGGAAATCAGCGGCGACCTGGCCTGCTTCACAAGAAGCGAGCT
GAAGGTCGAGCGGGTGTCATACCCTGTGATCACCCCTAGCGCCGCCAGAAACATCC
TGATGGCCATTCTGTGGAAGCCCGCCATCAGATGGAAGGTGCTGAAGATCGAGATC
CTGAAGCCTATCCAGTGGACCAACATCCGGCGGAACGAAGTGGGCACCAAGATGAG
CGAGAGAAGCGGCAGCCTGTACATCGAGGACAACAGACAGCAGCGGGCCTCCATGC
TGCTGAAGGATGTGGCCTATAGAATCCACGCCGACTTCGACATGACAAGCGAGGCC
GGCGAGAGCGACAACTACGTGAAGTTCGCCGAGATGTTCAAGCGGAGAGAGCCAAGAA
GGGCCAGTACTTCCACCAGCCTTACCTGGGCTGCAGAGAGTTCCCCTGCGACTTCAG
ACTGCTGGAAAAGGCCGAGGATGGCCTGCCTCTGGAAGATATCACCCAGGACTTCG
GCTTCATGCTGTACGACATGGACTTCAGCAAGAGCGACCCCAGAGACAGCAACAAC
GCCGAGCCTATGTTCTACCAGTGCAAGGCCGTGAACGGCGTGATCACTGTGCCTCCA
GCCGATAGCGAGGAAGTGAAGAGAGGCAGCGTCGGCTACCCCTACGATGTGCCTGA
TTACGCCCCTAAGAAAAAGCGGAAAGTGTGA human codon optimized cas8c with NLS and HA tag (SEQ ID NO: 9)
ATGGTGCCCAAGAAAAAGCGGAAGGTGTACCCCTACGACGTGCCCGATTATGCCGG
CTCTGTGGGAATTCTGCACGCCCTGACACAGTACTACCAGCGGAAGGCCGAAAGCG
ACGGCGGAATTGCCCAAGAGGGCTTCGAGAACAAAGAGATCCCCTTCATCATCGTG
ATCGACAAGCAGGGCAACTTCATCCAGCTCGAGGACACCCGCGAGCTGAAAGTGAA
GAAAAAGTGGGCCGCCACCTTCCTGGTGCCTAAAGGCCTTGGCCAGAAGCGGCAGCA
AGAGCTACGAGGTGTCCAACCTGCTGTGGGACCACTACGGATACGTGCTGGCCTATG
CCGGCGAGAAGGGACAAGAACCAGGCCGATAAGCAGCACGCCAGCTTCACCGCCAA
AGTGAACGAGCTGAAGCAGGCCCTGCCTGATGATGCTGGCGTGACAGCTGTGGCCG
CCTTTCTGTCTAGCGCCGAAGAGAAGTCCAAAGTGATGCAGGCCGCGCCAACTGGGCC
GAGTGCGCTAAAGTGAAGGGCTGCAACCTGAGCTTCCGGCTGGTGGATGAAGCCGT
GGATCTCGTGTGTCAGTCTAAGGCCGTGCGCGAGTATGTGTCCCAGGCCAATCAGAC
CCAGAGCGACAACGTGCAGAAAGGCATCTGTCTGGTCACCGGCAAGGCCGCTCCTA
TTGCCAGACTGCACAATGCCGTGAAGGGCGTGAACGCCAAGCCTGCTCCTTTCGCCT
CTGTGAACCTGAGCGCCTTTGAGAGCTACGGCAAAGAGCAGGGCTTCATCTTCCCTG
TGGGAGAGCAGGCCATGTTCGAGTACACCACCGCTCTGAATACCCTGCTGGCCTCCG
AGAACAGATTCCGGATCGGAGATGTGACCGCCGTGTGTTGGGGAGCCAAGAGAACA
CCTCTGGAAGAGTCCCTGGCCAGCATGATCAATGGCGGCGGAAAGGACAAGCCCGA
CGAGCACATCGACGCCGTGAAAACCCTGTACAAGAGCCTGTACAACGGCCAGTACC
AGAAGCCTGACGGAAAAGAGAAGTTCTACCTGCTGGGACTGAGCCCCAACAGCGCC
AGAATCGTTGTGCGGTTCTGGCACGAGACAACCGTGGCTGCCCTGTCTGAGTCTATC
GCCGCTTGGTACGACGACCTGCAGATGGTTCGAGGCGAGAACAGCCCCTATCCTGA
GTACATGCCCCTGCCTAGACTGCTGGGCAACCTGGTGCTGGACGGCAAGATGGAAA
ACCTGCCTAGCGACCTGATCGCCCAGATCACAGATGCTGCCCTGAACAACAGAGTG
CTGCCTGTCAGTCTGCTGCAGGCAGCCCTGAGAAGAAACAAGGCCGAGCAGAAGAT
CACCTACGGCAGAGCCAGCCTGCTGAAGGCCTACATCAACGGGCCATCAGAGCCG
GACGGCTGAAGAACATGAAGGAACTGACCATGGGCCTCGACCGGAACAGACAGGA
TATCGGCTATGTGCTGGGCAGACTGTTCGCCGTGCTGGAAAAGATTCAGGCCGAGGC
CAATCCTGGCCTGAACGCCACAATCGCCGACAGATATTTTGGCAGCGCCAGCAGCA
CACCTATCGCCGTGTTTGGCACCCTGATGAGACTGCTGCCTCACCACCTGAACAAGC
TGGAATTCGAGGGCAGAGCCGTGCAGCTCCAGTGGGAGATCAGACAGATCCTGGAA
CACTGCCAGCGGTTCCCCAATCACCTGAACCTGGAACAGCAGGGACTGTTTGCCATC
GGCTACTACCACGAGACACAGTTTCTGTTCACCAAGGACGCCCTGAAGAACCTGTTC
AACGAGGCCAAGACCGCCTGA
```

-continued

SEQUENCES

```
human codon optimized cas7 with NLS and HA tag (SEQ ID NO: 10)
ATGACCATCGAGAAGCGCTACGACTTCGTGTTCCTGTTCGACGTGCAAGACGGCAAC
CCCAACGGCGATCCTGATGCCGGAAACCTGCCTAGAATCGACCCTCAGACAGGCGA
GGGCCTCGTGACAGATGTGTGCCTGAAGCGGAAAGTGCGGAACTTCATCCAGATGA
CCCAGAACGACGAGCACCACGACATCTTCATCAGAGAGAAGGGCATCCTGAACAAC
CTGATCGACGAGGCCCACGAGCAAGAGAACGTGAAGGGCAAAGAGAAAGGCGAGA
AAACCGAGGCCGCCAGACAGTACATGTGCAGCCGGTACTACGACATCAGAACCTTC
GGCGCCGTGATGACCACCGGCAAGAATGCTGGACAAGTGCGGGGACCTGTGCAGCT
GACCTTCAGCAGATCCATCGATCCCATCATGACCCTGGAACACAGCATCACCAGAAT
GGCCGTGACCAATGAGAAGGACGCCAGCGAAACCGGCGACAACAGAACCATGGGC
AGAAAGTTCACCGTGCCTTACGGCCTGTACCGGTGCCACGGCTTTATCAGCACCCAC
TTCGCCAAGCAGACCGGCTTCAGCGAGAACGACCTGGAACTGTTTTGGCAGGCCCT
GGTCAACATGTTCGATCACGATCACTCTGCCGCCAGAGGCCAGATGAATGCCAGAG
GACTGTACGTGTTCGAGCACAGCAACAACCTGGGAGATGCCCCTGCCGACAGCCTG
TTCAAGAGAATCCAGGTGGTCAAGAAAGACGGCGTGGAAGTCGTGCGGAGCTTCGA
CGATTACCTGGTGTCCGTGGACGACAAGAACCTGGAAGAGACAAAGCTGCTGCGGA
AGCTCGGCGGCTCTGTGGGCTATCCTTACGACGTGCCAGACTACGCCCCTAAGAAAA
AGCGCAAAGTGTGA
```

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention, and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of altering a target DNA sequence, which method comprises introducing to a target DNA sequence:
   (a) a synthetic guide RNA sequence that is complementary to a target DNA sequence in a host cell; and
   (b) a combination of *Neisseria lactamica* proteins Cas3, Cas5, Cas8c, and Cas7.

2. The method of claim 1, wherein the target DNA sequence is in a host cell and said introducing comprises introducing (a) and (b) into said host cell.

3. The method of claim 2, wherein the method is conducted under conditions such that the guide RNA sequence binds to the target DNA sequence in the host cell, and the combination of *N. lactamica* proteins induces cleavage of one or both strands in the target DNA sequence, thereby altering the target DNA sequence in the host cell.

4. The method of claim 1, wherein said target DNA is target genomic DNA.

5. The method of claim 1, wherein the target DNA sequence encodes at least one gene product.

6. The method of claim 3, wherein the cleavage of one or both strands in the target genomic DNA sequence results in a deletion of the target genomic DNA sequence.

7. The method of claim 6, wherein the deletion is unidirectional.

8. The method of claim 7, wherein the deletion comprises from about 500 nucleotides to about 100,000 nucleotides.

9. The method of claim 8, wherein the deletion comprises from about 5,000 nucleotides to about 20,000 nucleotides.

10. The method of claim 2, wherein the synthetic guide RNA sequence and at least one of the *N. lactamica* proteins are introduced into the host cell as a ribonucleoprotein (RNP) complex.

11. The method of claim 2, wherein the synthetic guide RNA sequence is introduced into the host cell as part of a first vector and one or more nucleic acid sequences encoding the *N. lactamica* proteins are introduced into the host cell as part of a second vector, wherein the first vector and the second vector are different.

12. The method of claim 2, wherein the synthetic guide RNA sequence and one or more nucleic acid sequences encoding the *N. lactamica* proteins are introduced into the host cell as part of a single vector.

13. The method of claim 2, wherein the *N. lactamica* proteins are introduced into a host cell by contacting the host cell with one or more mRNA sequences encoding the *N. lactamica* proteins.

14. The method of claim 13, wherein the host cell genome comprises a protospacer adjacent motif (PAM) comprising the nucleic acid sequence 5'-TTC-3' or 5'-TTT-3' located adjacent to the target genomic DNA sequence.

15. The method of claim 1, wherein the target DNA sequence encodes a protein.

16. The method of claim 2, wherein the host cell is a eukaryotic cell.

17. The method of claim 16, wherein the host cell is a human cell.

18. The method of claim 1, wherein the *N. lactamica* proteins are encoded by a nucleic acid sequence that is codon optimized.

19. The method of claim 18, wherein:
   (a) the Cas3 protein is encoded by the nucleic acid sequence of SEQ ID NO: 1 or SEQ ID NO: 7,
   (b) the Cas5 protein is encoded by the nucleic acid sequence of SEQ ID NO: 2 or SEQ ID NO: 8,
   (c) the Cas8c protein is encoded by the nucleic acid sequence of SEQ ID NO: 3 or SEQ ID NO: 9, and
   (d) the Cas7 protein is encoded by the nucleic acid sequence of SEQ ID NO: 4 or SEQ ID NO: 10.

* * * * *

SEQUENCE LISTING

```
<160> NUMBER OF SEQ ID NOS: 91

<210> SEQ ID NO 1
<211> LENGTH: 2505
<212> TYPE: DNA
<213> ORGANISM: Artificial sequence
<220> FEATURE:
<223> OTHER INFORMATION: Synthetic

<400> SEQUENCE: 1
gtgaatttcg actatatagc ccacgctcgc caagactcat caaaaaattg gcattcccat      60
cccctgcaaa aacatctaca aaaagtcgcc caactcgcca agcgttttgc agggcgttat     120
gggtcgttgt ttgccgaata tgcggggctt ttgcacgatt tggggaaatt tcaggaatct     180
tttcagaaat atatccgtaa tgcatccggc tttgaaaaag aaaatgccca tttggaagat     240
gtcgaatcta ccaagttgcg caaaattccg cattccactg ccggtgccaa atatgcggta     300
```

-continued

```
gaacgtctaa atccattttt cgggcatttg ctggcatatt tgattgccgg gcatcatgct      360
gggctggcag attggtatga caaaggcagc ctgaaacgcc gtctgcaaca ggcggatgac      420
gagttggcag cgtctttgtc gggctttgtg aaagtagtt tgcccgaaga tttttttcccg      480 ttatcagatg atgacttgat gcgggatttt tttgcgtttt gggaagacgg ggcaaagctg      540
gaagaattgc atatttggat gcgttttctc ttttcctgct tggtggatgc cgatttttttg      600 gataccgaag cctttatgaa cggctatgcc gatgcagata ctgcgcaggc tgccggattg      660
cgcccaaaat ttcccggttt ggatgagtta caccggcgat atgagcaata tatggcgcaa      720
ctttcagaaa aagcagataa aaattcatct ttaaaccaag aacgccacgc cattttgcag      780
caatgttttt ctgccgcaga aacggaccgt actttgtttt ctttaaccgt gccgaccggt      840
ggcggtaaaa ctttggcgag cttgggcttc gctttgaagc acgcgctgaa atttggcaaa      900
aaacgtatta tctatgctat tcctttcacc agtattatcg agcagaatgc caatgttttc      960
cgcaatgcat taggcgatga tgtggtttta gaacaccaca gcaatttgga agtgaaagaa     1020
gataaggaaa cagcgaaaac tcgtcttgct acggaaaatt gggacgcgcc gctgattgtt     1080
actaccaatg tgcaactgtt tgaaagcctg tttgcggcga aaaccagccg ttgccgcaag     1140
attcacaata ttgccgacag cgtggtgatt ttggatgaag cccagcagct tccgcgcgat     1200
ttccaaaaac cgattaccga catgatgcgg gtgctggcgc gtgattacgg cgttaccttt     1260
gtgctgtgca cggcaaccca accggagctt ggcaaaaata tcgacgcatt cggtcgcact     1320
attttggaag ggctaccaga tgtgcgcgaa attgtggcag acaaaattgc cttatcggaa     1380
aaactgcgcc gcgtccgcat caaaatgccg ccgccaaacg cgaaacgca aagctggcag     1440 aaaattgccg atgaaatagc cgcgcgcccg tgtgtttttgg cagtggtcaa tacgcgaaaa     1500
cacgcccaaa aactctttgc cgccctgcct tctaacggaa tcaagctaca tttatctgcc     1560
aatatgtgcg ccacacactg cagcgaagtg attgcgttgg ttcgccgata tttggcactg     1620
tatcgcgcag gcagcctgca caagcccttg tggctggtca gcacgcagtt gattgaagca     1680
ggcgtggatt tggatttccc ttgcgtgtat cgggcgatgg cagggctgga cagcattgcc     1740
caggcggcgg gacggtgcaa ccgtgaaggt aaactgccgc agttgggcga agtagtcgta     1800
ttccgcgccg aagaaggcgc gcccagcggc agcctgaaac aggggcagga cattaccgaa     1860
gagatgctga aagcagggct gcttgatgac ccgctttccc cgttggcatt tgccgaatat     1920
ttccgccgat tcaacggcaa aggtgatgtg gacaaaacacg gtatcacaac gcttttgacg     1980
gcagaagcat caaatgaaaa tccgctggca attaaattcc gcacagctgc cgaacgtttc     2040
cacctgattg ataaccaagg cgtggcactc attgtgccgt ttatcccgtt ggctcattgg     2100
gaaaaagacg gcagtccgca aatcgtcgaa gcaaacgagc tggacgattt tttcagacga     2160
catctagatg gtgttgaagt ttcagaatgg caggatattt tggacaaaca acgctttccg     2220
cagccgccag acaactcctt tgggcaaacc gatcaaccac tgctgcccga gccgtttgaa     2280
agctggttcg gtctgttgga aagcgacccg ctcaaacaca aatgggttta ccgcaagctg     2340
caacgctaca cgattactgt gtacgaacac gaactgaaaa agttgcctga acatgccgtt     2400
ttttcaagag cgggattgct cgtgttagat aagggctatt acaaagccgt gcttggcgcg     2460
gattttgacg atgcggcttg gctacctgaa aattcggttt tatga                     2505
```

<210> SEQ ID NO 2
<211> LENGTH: 645
<212> TYPE: DNA
<213> ORGANISM: Artificial sequence -continued

```
<220> FEATURE:
<223> OTHER INFORMATION: Synthetic

<400> SEQUENCE: 2
atgaggttca tcctggaaat cagtggtgat ttggcatgct tcacaaggtc tgagctaaag      60
gtggaaaggg ttagttatcc tgtgataacg ccgtctgccg ccaggaacat cctaatggcg     120
atattgtgga agccggcgat tcgctggaag gtcttgaaga tagaaatcct aaaaccgatt     180
cagtggacga atatccgccg caacgaagtg ggaactaaga tgagtgagcg tagcggctcg     240
ctctatattg aagataaccg ccagcagcgc gcatccatgc tgctgaaaga cgttgcctac     300
cgcattcacg ccgattttga catgaccagt gaagcgggcg agagcgacaa ctatgttaaa     360
tttgccgaaa tgttcaagcg gcgggcaaag aaaggacaat atttccacca accttattta     420
ggctgtcgtg agtttccttg tgatttcagg ttgctggaaa aagccgaaga tggattgcca     480
ctcgaagaca ttacccaaga tttcggtttt atgctgtatg acatggattt cagcaaatcc     540
gacccgcgtg attccaataa cgccgagccg atgtttttacc aatgcaaagc ggtaaacggc     600
gtgattaccg tgccgcctgc cgacagcgag gaggtgaaac gatga                     645

<210> SEQ ID NO 3
<211> LENGTH: 1758
<212> TYPE: DNA
<213> ORGANISM: Artificial sequence
<220> FEATURE:
<223> OTHER INFORMATION: Synthetic

<400> SEQUENCE: 3
atgattttgc acgcgctcac ccaatactat caacgcaaag ccgaaagtga tggcggtatt      60
gcccaggaag ggtttgaaaa caaagaaata ccgttcatta tcgttataga caaacagggt     120
aattttattc agctggaaga tacccgtgag ctgaaagtta agaagaaagt tggccgcact     180
tttttagtac cgaaaggttt gggcaggagc ggttcaaaat cctacgaagt aagcaattta     240
ttgtgggatc actacggtta tgtacttgct tatgccggag aaaaagggca ggagcaggcg     300
gacaaacagc atgccagctt taccgccaaa gtaaatgaat tgaaacaggc gctgcccgat     360
gatgcaggtg ttactgcggt tgctgccttt ttgtcttctg cggaagaaaa aagcaaagtc     420
atgcaggctg caaattgggc ggagtgtgcc aaagtcaaag gctgtaatct cagcttccgc     480
ctggtggatg aagcggtaga tttggtttgc agtcaaagg cggtgcggga atatgtgagt      540
caagcaaatc aaacgcaatc cgataatgtc caaaaaggca tttgcctggt aacgggcaaa     600
gctgcgccga ttgcgcggct gcataacgcc gtgaaaggcg tgaatgccaa gcccgccccg     660
tttgcatcgg taaatctgtc ggcttttgaa tcatacggca agagcagggg ctttatcttt     720
cccgtgggcg agcaagccat gttcgaatat accaccgcct tgaacacctt gcttgctagc     780
gaaaaccgat tccgtatcgg cgatgtaacg gccgtatgtt ggggcgcgaa acggactccg     840
ttggaggaaa gtcttgcttc gatgattaac ggcggcggca aagacaagcc cgatgagcat     900
atcgatgccg ttaaaactct ttataaaagc ctatacaacg gtcaataccca aaaacctgac     960 ggcaaagaaa aattctacct tttaggtttta tcgcccaatt ccgcgcgcat tgtcgtccgc    1020
ttttggcatg aaaccaccgt tgccgcctta tcagaaagta ttgcggcgtg gtatgacgat    1080
ttgcaaatgg tgcgcggcga aaactcgcca taccccgaat atatgccgct accgcgcctg    1140
ctgggtaatt tggtgttgga cggcaaaatg gaaaacctgc catctgacct gattgcccaa    1200
ataaccgatg ccgcgctcaa caaccgtgtt ttacccgtca gcctgttgca ggctgctttg    1260
```

-continued

```
cggcgcaaca aggcggaaca gaaaattacc tatggcagag caagtctgct taaagcctat      1320
atcaatcgcg caatccgtgc gggtcgtctg aaaaacatga aggagctaac tatgggccta      1380
gatagaaacc gtcaagacat cggctatgtg ctggggcggc tgtttgccgt gctggaaaaa      1440
atacaagccg aggccaatcc cggcttgaac gccaccattg ccgaccgcta tttcggttcg      1500
gcaagcagca caccgattgc cgtattcggc acactgatgc gcttgttgcc gcaccatttg      1560
aacaaactgg aatttgaagg acgtgccgta caactgcaat gggaaatccg ccagattttg      1620
gaacattgtc agagatttcc taaccatttg aatttggaac agcaaggcct atttgccatc      1680
ggttactacc acgaaaccca attcctgttt accaaagacg cattgaaaaa cctgttcaac      1740
gaagcgaaaa ccgcataa                                                    1758

<210> SEQ ID NO 4
<211> LENGTH: 849
<212> TYPE: DNA
<213> ORGANISM: Artificial sequence
<220> FEATURE:
<223> OTHER INFORMATION: Synthetic

<400> SEQUENCE: 4
atgactattg aaaaacgcta cgactttgtc tttttatttg atgtgcaaga cggcaatccc        60
aacggcgatc ctgacgcagg taacctgccg cgtatcgacc cgcaaaccgg cgaaggtttg       120
gtaactgatg tttgcctgaa acgcaaagtc cgcaacttta tccaaatgac tcaaaatgac       180
gaacatcacg acatctttat ccgcgaaaaa ggcattttga acaacctgat tgacgaagcc       240
cacgagcagg aaaacgtaaa aggcaaagaa aaaggcgaga aaaccgaagc tgcccgccaa       300
tacatgtgca gccgttatta cgacatccgc acatttggcg cagtgatgac taccggcaaa       360
aatgcaggac aagtacgcgg tcccgtgcaa ctgactttt ctcgctctat tgatcccatc        420
atgaccttgg aacacagcat tacccgcatg gcggttacca acgaaaaaga tgccagtgaa       480
accggcgaca accgtacaat gggtcgcaaa ttcaccgtcc cctacggtct ataccgctgc       540
catggcttca tttctacccca ttttgccaaa caaacaggct tttccgaaaa cgatttagag       600 ctgtttggc aggcacttgt caatatgttt gaccacgacc attccgccgc acgcggacaa        660
atgaacgcac gcgggctcta tgtgtttgaa cacagcaata atctaggtga tgcgcctgct       720
gatagtctgt tcaaacgcat tcaggtagtc aaaaaggacg gtgtagaagt agtaaggagt       780
tttgacgatt atcttgtcag cgtagacgat aagaatcttg aagaaaccaa gctgttgcgt       840
aaattaggc                                                              849

<210> SEQ ID NO 5
<211> LENGTH: 32
<212> TYPE: DNA
<213> ORGANISM: Artificial sequence
<220> FEATURE:
<223> OTHER INFORMATION: Synthetic

<400> SEQUENCE: 5
tcagccgcct ctaggcggct gtgtgttgaa ac                                       32

<210> SEQ ID NO 6
<211> LENGTH: 35
<212> TYPE: DNA
<213> ORGANISM: Artificial sequence
<220> FEATURE:
<223> OTHER INFORMATION: Synthetic

<400> SEQUENCE: 6
```

-continued

```
gagggcgaca ccctggtgaa ccgcatcgag ctgaa                         35

<210> SEQ ID NO 7
<211> LENGTH: 2583
<212> TYPE: DNA
<213> ORGANISM: Artificial sequence
<220> FEATURE:
<223> OTHER INFORMATION: Synthetic

<400> SEQUENCE: 7
atgaacttcg actatatcgc ccacgccaga caggacagca gcaagaactg gcactctcac      60
cctctgcaga aacatctgca gaaggtggcc cagctggcca agagatttgc cggcagatac     120
ggcagcctgt tcgccgaata tgccggcctg ctgcacgatc tgggcaagtt ccaagagagc     180
ttccagaagt acatccggaa cgccagcggc ttcgagaaag agaatgccca cctggaagat     240
gtggaaagca ccaagctgcg gaagatccct cactctacag ccggcgctaa gtacgccgtg     300
gaaagactga cccccttctt cggccatctg ctggcctatc tgattgccgg acatcatgcc     360
ggactggccg attggtacga taagggcagc ctgaagcgga gactgcagca agccgatgat     420
gaactggccg cctctctgtc cggcttcgtg gaatcttctc tgcccgagga cttcttccct     480
ctgtccgacg acgacctgat gagagacttc ttcgccttct gggaggacgg cgccaagctg     540
gaagaactgc acatctggat gcggtttctg ttcagctgcc tggtggacgc cgacttcctg     600
gataccgagg ccttcatgaa cggctacgcc gatgccgata gcccaagc tgctggactg      660 aggcctaagt ccctggcct ggatgagctg catcggagat acgagcagta catggctcag     720
ctgtccgaga aggccgacaa gaacagctcc ctgaatcaag agcggcacgc catcctgcag     780
cagtgctttt ctgccgccga gacagacaga accctgttca gcctgacagt gcctacaggc     840
ggcggaaaaa ctctggcctc tctgggcttt gccctgaagc acgccctgaa gttcggcaag     900
aagcggatca tctacgccat tcctttcacc agcatcatcg agcagaacgc caacgtgttc     960
agaaacgccc tgggcgacga tgtggtgctg gaacaccaca gcaacctgga agtgaaagag    1020
gacaaagaga cagccaagac cagactggcc accgagaatt gggatgcccc tctgatcgtg    1080
accaccaacg tgcagctgtt cgagagcctg tttgccgcca gacctccag atgcagaaag     1140 atccacaata tcgccgacag cgtggtcatc ctggacgaag ctcagcagct gccccgggac    1200
ttccagaaac ctatcaccga tatgatgcgc gtgctggcca gagactacgg cgtgaccttt    1260
gtgctgtgta ccgccacaca gcctgagctg ggcaagaaca tcgatgcctt cggccggacc    1320
atcctggaag gattgcctga cgtgcgggaa atcgtggccg ataagatcgc cctgagcgag    1380
aagctgagaa gagtgcggat caagatgcct cctccaaacg gcgagacaca gagctggcag    1440
aagatcgccg acgagatcgc cgctagacca tgtgtgctgg ccgtggtcaa caccagaaaa    1500
cacgcccaga gctgttcgc tgccctgcct agcaatggca tcaagctgca cctgagcgcc     1560
aacatgtgcg ccacacactg ctctgaagtg atcgccctcg tgcggagata tctgccctg    1620 tacagagccg gaagcctgca caaacctctg tggctggtgt ctacccagct gattgaagct    1680
ggcgtggacc tggacttccc ctgtgtgtat agagccatgg ccggcctgga ttctattgcc    1740
caagcagccg acggtgcaa cagagaggga aaactgcctc agctgggcga gtggtggtg     1800 ttcagagctg aagaaggcgc ccctagcggc tctctgaagc aaggccagga tatcaccgag    1860
gaaatgctga aggccggact gctggacgac cctttgtctc ctctggcctt cgccgagtac    1920
ttcagacggt tcaatggcaa gggcgacgtg gacaagcacg gcatcacaac actgctgaca    1980
```

-continued

```
gccgaggcca gcaacgagaa tccactggcc atcaagttcc ggaccgccgc tgagagattc      2040
cacctgatcg ataatcaggg cgtcgcactg atcgtgccct tcattcctct ggctcactgg      2100
gagaaagacg gcagccctca gatcgtggaa gccaacgagc tggacgattt cttcaggcgg      2160
cacctggacg gcgtggaagt gtctgagtgg caggacatcc tggataagca gcggttccct      2220
cagcctcctg acaacagctt tggccagacc gatcagcctc tgctgcctga gcctttcgag      2280
agttggttcg gcctgctcga gagcgaccca ctgaagcaca atgggtgta ccggaagctg      2340 cagcggtaca ccatcaccgt gtatgagcac gagctgaaaa agctgcccga gcacgccgtg      2400
ttctctagag ctggactgct cgtgctggac aagggctact ataaggccgt gctgggcgcc      2460
gattttgacg atgctgcttg gctgccagag aactctgtgc tgggctctgt gggctacccc      2520
tacgatgtgc ctgattacgc cggcagctac cctgagttcc ccaagaaaaa gcggaaagtg      2580
tga                                                                    2583
```

```
<210> SEQ ID NO 8
<211> LENGTH: 705
<212> TYPE: DNA
<213> ORGANISM: Artificial sequence
<220> FEATURE:
<223> OTHER INFORMATION: Synthetic

<400> SEQUENCE: 8
atgcggttca tcctggaaat cagcggcgac ctggcctgct tcacaagaag cgagctgaag        60
gtcgagcggg tgtcataccc tgtgatcacc cctagcgccg ccagaaacat cctgatggcc       120
attctgtgga agcccgccat cagatggaag gtgctgaaga tcgagatcct gaagcctatc       180
cagtggacca acatccggcg gaacgaagtg ggcaccaaga tgagcgagag aagcggcagc       240
ctgtacatcg aggacaacag acagcagcgg gcctccatgc tgctgaagga tgtggcctat       300
agaatccacg ccgacttcga catgacaagc gaggccggcg agagcgacaa ctacgtgaag       360
ttcgccgaga tgttcaagcg gagagccaag aagggccagt acttccacca gccttacctg       420
ggctgcagag agttcccctg cgacttcaga ctgctggaaa aggccgagga tggcctgcct       480
ctggaagata tcacccagga cttcggcttc atgctgtacg acatggactt cagcaagagc       540
gaccccagag acagcaacaa cgccgagcct atgttctacc agtgcaaggc cgtgaacggc       600
gtgatcactg tgcctccagc cgatagcgag gaagtgaaga gaggcagcgt cggctacccc       660
tacgatgtgc ctgattacgc ccctaagaaa aagcggaaag tgtga                      705
```

```
<210> SEQ ID NO 9
<211> LENGTH: 1821
<212> TYPE: DNA
<213> ORGANISM: Artificial sequence
<220> FEATURE:
<223> OTHER INFORMATION: Synthetic

<400> SEQUENCE: 9
atggtgccca agaaaaagcg gaaggtgtac ccctacgacg tgcccgatta tgccggctct        60
gtgggaattc tgcacgccct gacacagtac taccagcgga aggccgaaag cgacggcgga       120
attgcccaag agggcttcga gaacaaagag atccccttca tcatcgtgat cgacaagcag       180
ggcaacttca tccagctcga ggacacccgc gagctgaaag tgaagaaaaa agtgggccgc       240
accttcctgg tgcctaaagg ccttggcaga agcggcagca agagctacga ggtgtccaac       300
ctgctgtggg accactacgg atacgtgctg gcctatccgg cgagaaggg acaagaacag       360 gccgataagc agcacgccag cttcaccgcc aaagtgaacg agctgaagca ggccctgcct       420
```

-continued

```
gatgatgctg gcgtgacagc tgtggccgcc tttctgtcta gcgccgaaga gaagtccaaa      480
gtgatgcagg ccgccaactg ggccgagtgc gctaaagtga agggctgcaa cctgagcttc      540
cggctggtgg atgaagccgt ggatctcgtg tgtcagtcta aggccgtgcg cgagtatgtg      600
tcccaggcca atcagaccca gagcgacaac gtgcagaaag gcatctgtct ggtcaccggc      660
aaggccgctc ctattgccag actgcacaat gccgtgaagg gcgtgaacgc caagcctgct      720
cctttcgcct ctgtgaacct gagcgccttt gagagctacg gcaaagagca gggcttcatc      780
ttccctgtgg gagagcaggc catgttcgag tacaccaccg ctctgaatac cctgctggcc      840
tccgagaaca gattccggat cggagatgtg accgccgtgt gttggggagc caagagaaca      900
cctctggaag agtccctggc cagcatgatc aatggcggcg aaaggacaa gcccgacgag      960 cacatcgacg ccgtgaaaac cctgtacaag agcctgtaca acggccagta ccagaagcct     1020
gacggaaaag agaagttcta cctgctggga ctgagcccca cagcgccag aatcgttgtg     1080 cggttctggc acgagacaac cgtggctgcc ctgtctgagt ctatcgccgc ttggtacgac     1140
gacctgcaga tggttcgagg cgagaacagc ccctatcctg agtacatgcc cctgcctaga     1200
ctgctgggca acctggtgct ggacggcaag atggaaaacc tgcctagcga cctgatcgcc     1260
cagatcacag atgctgccct gaacaacaga gtgctgcctg tcagtctgct gcaggcagcc     1320
ctgagaagaa acaaggccga gcagaagatc acctacggca gagccagcct gctgaaggcc     1380
tacatcaacc gggccatcag agccggacgg ctgaagaaca tgaaggaact gaccatgggc     1440
ctcgaccgga acagacagga tatcggctat gtgctgggca gactgttcgc cgtgctggaa     1500
aagattcagg ccgaggccaa tcctggcctg aacgccacaa tcgccgacag atattttggc     1560
agcgccagca gcacacctat cgccgtgttt ggcaccctga tgagactgct gcctcaccac     1620
ctgaacaagc tggaattcga gggcagagcc gtgcagctcc agtgggagat cagacagatc     1680
ctggaacact gccagcggtt ccccaatcac ctgaacctgg aacagcaggg actgtttgcc     1740
atcggctact accacgagac acagtttctg ttcaccaagg acgccctgaa gaacctgttc     1800
aacgaggcca agaccgcctg a                                              1821
```

<210> SEQ ID NO 10
<211> LENGTH: 912
<212> TYPE: DNA
<213> ORGANISM: Artificial sequence
<220> FEATURE:
<223> OTHER INFORMATION: Synthetic

<400> SEQUENCE: 10

```
atgaccatcg agaagcgcta cgacttcgtg ttcctgttcg acgtgcaaga cggcaacccc       60
aacggcgatc ctgatgccgg aaacctgcct agaatcgacc ctcagacagg cgagggcctc      120
gtgacagatg tgtgcctgaa gcggaaagtg cggaacttca tccagatgac ccagaacgac      180
gagcaccacg acatcttcat cagagagaag ggcatcctga caacctgat cgacgaggcc       240 cacgagcaag agaacgtgaa gggcaaagag aaaggcgaga aaaccgaggc cgccagacag      300
tacatgtgca gccggtacta cgacatcaga accttcggcg ccgtgatgac caccggcaag      360
aatgctggac aagtgcgggg aacctgtcag ctgaccttca gcagatccat cgatcccatc      420
atgaccctgg aacacagcat caccagaatg gccgtgacca atgagaagga cgccagcgaa      480 accgcgaca acagaaccat gggcagaaag ttcaccgtgc cttacggcct gtaccggtgc      540
cacggcttta tcagcaccca cttcgccaag cagaccggct tcagcgagaa cgacctggaa      600
```

-continued

```
ctgttttggc aggccctggt caacatgttc gatcacgatc actctgccgc cagaggccag       660
atgaatgcca gaggactgta cgtgttcgag cacagcaaca acctgggaga tgccctgcc        720 gacagcctgt tcaagagaat ccaggtggtc aagaaagacg gcgtggaagt cgtgcggagc       780
ttcgacgatt acctggtgtc cgtggacgac aagaacctgg aagagacaaa gctgctgcgg       840
aagctcggcg gctctgtggg ctatccttac gacgtgccag actacgcccc taagaaaaag       900
cgcaaagtgt ga                                                           912
```

```
<210> SEQ ID NO 11
<211> LENGTH: 54
<212> TYPE: DNA
<213> ORGANISM: Artificial sequence
<220> FEATURE:
<223> OTHER INFORMATION: Synthetic

<400> SEQUENCE: 11
gatgcccttc agctcgatgc ggttcaccag ggtgtcgccc tcgaacttca cctc            54
```

```
<210> SEQ ID NO 12
<211> LENGTH: 54
<212> TYPE: DNA
<213> ORGANISM: Artificial sequence
<220> FEATURE:
<223> OTHER INFORMATION: Synthetic

<400> SEQUENCE: 12
gaggtgaagt tcgagggcga caccctggtg aaccgcatcg agctgaaggg catc            54
```

```
<210> SEQ ID NO 13
<211> LENGTH: 10
<212> TYPE: DNA
<213> ORGANISM: Artificial sequence
<220> FEATURE:
<223> OTHER INFORMATION: Synthetic

<400> SEQUENCE: 13
cttttcattt                                                             10
```

```
<210> SEQ ID NO 14
<211> LENGTH: 10
<212> TYPE: DNA
<213> ORGANISM: Artificial sequence
<220> FEATURE:
<223> OTHER INFORMATION: Synthetic

<400> SEQUENCE: 14
atggcgtttt                                                             10
```

```
<210> SEQ ID NO 15
<211> LENGTH: 10
<212> TYPE: DNA
<213> ORGANISM: Artificial sequence
<220> FEATURE:
<223> OTHER INFORMATION: Synthetic

<400> SEQUENCE: 15
cgcgctgttc                                                             10
```

```
<210> SEQ ID NO 16
<211> LENGTH: 10
<212> TYPE: DNA
<213> ORGANISM: Artificial sequence
<220> FEATURE:
<223> OTHER INFORMATION: Synthetic
```

-continued

<400> SEQUENCE: 16
gagacttcaa                                                            10

<210> SEQ ID NO 17
<211> LENGTH: 10
<212> TYPE: DNA
<213> ORGANISM: Artificial sequence
<220> FEATURE:
<223> OTHER INFORMATION: Synthetic

<400> SEQUENCE: 17
gcgtggcttc                                                            10

<210> SEQ ID NO 18
<211> LENGTH: 10
<212> TYPE: DNA
<213> ORGANISM: Artificial sequence
<220> FEATURE:
<223> OTHER INFORMATION: Synthetic

<400> SEQUENCE: 18
acggcgtttt                                                            10

<210> SEQ ID NO 19
<211> LENGTH: 10
<212> TYPE: DNA
<213> ORGANISM: Artificial sequence
<220> FEATURE:
<223> OTHER INFORMATION: Synthetic

<400> SEQUENCE: 19
atatattttc                                                            10

<210> SEQ ID NO 20
<211> LENGTH: 10
<212> TYPE: DNA
<213> ORGANISM: Artificial sequence
<220> FEATURE:
<223> OTHER INFORMATION: Synthetic

<400> SEQUENCE: 20
tcgtggtttc                                                            10

<210> SEQ ID NO 21
<211> LENGTH: 10
<212> TYPE: DNA
<213> ORGANISM: Artificial sequence
<220> FEATURE:
<223> OTHER INFORMATION: Synthetic

<400> SEQUENCE: 21
gcggcggttc                                                            10

<210> SEQ ID NO 22
<211> LENGTH: 10
<212> TYPE: DNA
<213> ORGANISM: Artificial sequence
<220> FEATURE:
<223> OTHER INFORMATION: Synthetic

<400> SEQUENCE: 22
ggagacttca                                                            10

<210> SEQ ID NO 23

<211> LENGTH: 10
<212> TYPE: DNA
<213> ORGANISM: Artificial sequence
<220> FEATURE:
<223> OTHER INFORMATION: Synthetic

<400> SEQUENCE: 23
tttctaattc                                                              10

<210> SEQ ID NO 24
<211> LENGTH: 10
<212> TYPE: DNA
<213> ORGANISM: Artificial sequence
<220> FEATURE:
<223> OTHER INFORMATION: Synthetic

<400> SEQUENCE: 24
agaacgattc                                                              10

<210> SEQ ID NO 25
<211> LENGTH: 10
<212> TYPE: DNA
<213> ORGANISM: Artificial sequence
<220> FEATURE:
<223> OTHER INFORMATION: Synthetic

<400> SEQUENCE: 25
tgcagttttc                                                              10

<210> SEQ ID NO 26
<211> LENGTH: 10
<212> TYPE: DNA
<213> ORGANISM: Artificial sequence
<220> FEATURE:
<223> OTHER INFORMATION: Synthetic

<400> SEQUENCE: 26
cgcgctcttc                                                              10

<210> SEQ ID NO 27
<211> LENGTH: 10
<212> TYPE: DNA
<213> ORGANISM: Artificial sequence
<220> FEATURE:
<223> OTHER INFORMATION: Synthetic

<400> SEQUENCE: 27
aggcgatttc                                                              10

<210> SEQ ID NO 28
<211> LENGTH: 10
<212> TYPE: DNA
<213> ORGANISM: Artificial sequence
<220> FEATURE:
<223> OTHER INFORMATION: Synthetic

<400> SEQUENCE: 28
aatcgtattc                                                              10

<210> SEQ ID NO 29
<211> LENGTH: 10
<212> TYPE: DNA
<213> ORGANISM: Artificial sequence
<220> FEATURE:
<223> OTHER INFORMATION: Synthetic

<400> SEQUENCE: 29
aatcatattc                                                                         10

<210> SEQ ID NO 30
<211> LENGTH: 10
<212> TYPE: DNA
<213> ORGANISM: Artificial sequence
<220> FEATURE:
<223> OTHER INFORMATION: Synthetic

<400> SEQUENCE: 30
gtgttgaaac                                                                         10

<210> SEQ ID NO 31
<211> LENGTH: 34
<212> TYPE: DNA
<213> ORGANISM: Artificial sequence
<220> FEATURE:
<223> OTHER INFORMATION: Synthetic

<400> SEQUENCE: 31
catgaaaaac cctttttcga taaatacggc gttc                                              34

<210> SEQ ID NO 32
<211> LENGTH: 34
<212> TYPE: DNA
<213> ORGANISM: Artificial sequence
<220> FEATURE:
<223> OTHER INFORMATION: Synthetic

<400> SEQUENCE: 32
tatagattgg ttgtcattca cgatgcacga agat                                              34

<210> SEQ ID NO 33
<211> LENGTH: 35
<212> TYPE: DNA
<213> ORGANISM: Artificial sequence
<220> FEATURE:
<223> OTHER INFORMATION: Synthetic

<400> SEQUENCE: 33
cttgtcttaa tagtaacaac tgcattgaga ccgca                                             35

<210> SEQ ID NO 34
<211> LENGTH: 35
<212> TYPE: DNA
<213> ORGANISM: Artificial sequence
<220> FEATURE:
<223> OTHER INFORMATION: Synthetic

<400> SEQUENCE: 34
aaaaaaccat accgaccccc acggcgcggc aggaa                                             35

<210> SEQ ID NO 35
<211> LENGTH: 34
<212> TYPE: DNA
<213> ORGANISM: Artificial sequence
<220> FEATURE:
<223> OTHER INFORMATION: Synthetic

<400> SEQUENCE: 35
catgaaaaaa cctttttcga taaatacggc gttc                                              34

<210> SEQ ID NO 36
<211> LENGTH: 35
<212> TYPE: DNA

-continued

```
<213> ORGANISM: Artificial sequence
<220> FEATURE:
<223> OTHER INFORMATION: Synthetic

<400> SEQUENCE: 36
cgccagcagt tcggtggcgc gttgctcaat acggg                          35

<210> SEQ ID NO 37
<211> LENGTH: 34
<212> TYPE: DNA
<213> ORGANISM: Artificial sequence
<220> FEATURE:
<223> OTHER INFORMATION: Synthetic

<400> SEQUENCE: 37
tatagattgg ttgtcatttc agatgcacga agat                           34

<210> SEQ ID NO 38
<211> LENGTH: 34
<212> TYPE: DNA
<213> ORGANISM: Artificial sequence
<220> FEATURE:
<223> OTHER INFORMATION: Synthetic

<400> SEQUENCE: 38
agttgacggc gtatgccccg aacctaaaag cgta                           34

<210> SEQ ID NO 39
<211> LENGTH: 35
<212> TYPE: DNA
<213> ORGANISM: Artificial sequence
<220> FEATURE:
<223> OTHER INFORMATION: Synthetic

<400> SEQUENCE: 39
ccgccacaaa taccacccac cgcctcgctg cccac                          35

<210> SEQ ID NO 40
<211> LENGTH: 34
<212> TYPE: DNA
<213> ORGANISM: Artificial sequence
<220> FEATURE:
<223> OTHER INFORMATION: Synthetic

<400> SEQUENCE: 40
agttgacggc gtatgccccg aacctagaag cgta                           34

<210> SEQ ID NO 41
<211> LENGTH: 34
<212> TYPE: DNA
<213> ORGANISM: Artificial sequence
<220> FEATURE:
<223> OTHER INFORMATION: Synthetic

<400> SEQUENCE: 41
agacacacgc ccgaagcatc aacggcttgg aggc                           34

<210> SEQ ID NO 42
<211> LENGTH: 35
<212> TYPE: DNA
<213> ORGANISM: Artificial sequence
<220> FEATURE:
<223> OTHER INFORMATION: Synthetic

<400> SEQUENCE: 42
aaaaaaccac accgaccccc acggcgcagc aggaa                          35
```

-continued

<210> SEQ ID NO 43
<211> LENGTH: 35
<212> TYPE: DNA
<213> ORGANISM: Artificial sequence
<220> FEATURE:
<223> OTHER INFORMATION: Synthetic

<400> SEQUENCE: 43
gatacggggg cggtagtcgt cctctgttaa atagg                                35

<210> SEQ ID NO 44
<211> LENGTH: 34
<212> TYPE: DNA
<213> ORGANISM: Artificial sequence
<220> FEATURE:
<223> OTHER INFORMATION: Synthetic

<400> SEQUENCE: 44
aacgaaatca acaattatct cggcggcttt ggta                                 34

<210> SEQ ID NO 45
<211> LENGTH: 35
<212> TYPE: DNA
<213> ORGANISM: Artificial sequence
<220> FEATURE:
<223> OTHER INFORMATION: Synthetic

<400> SEQUENCE: 45
gtattgaaga aaccggttac atatacgcag caaac                                35

<210> SEQ ID NO 46
<211> LENGTH: 34
<212> TYPE: DNA
<213> ORGANISM: Artificial sequence
<220> FEATURE:
<223> OTHER INFORMATION: Synthetic

<400> SEQUENCE: 46
acccatgcaa agcagcttgt agcctatcta ggac                                 34

<210> SEQ ID NO 47
<211> LENGTH: 34
<212> TYPE: DNA
<213> ORGANISM: Artificial sequence
<220> FEATURE:
<223> OTHER INFORMATION: Synthetic

<400> SEQUENCE: 47
cgtcttcgcc gcgctgaaaa acgcttattt cgcc                                 34

<210> SEQ ID NO 48
<211> LENGTH: 34
<212> TYPE: DNA
<213> ORGANISM: Artificial sequence
<220> FEATURE:
<223> OTHER INFORMATION: Synthetic

<400> SEQUENCE: 48
ctgtcttaat agtaacaact gcattgagac cgca                                 34

<210> SEQ ID NO 49
<211> LENGTH: 34
<212> TYPE: DNA
<213> ORGANISM: Artificial sequence
<220> FEATURE:

-continued

```
<223> OTHER INFORMATION: Synthetic

<400> SEQUENCE: 49
agcgcagccg tagtcaacgc agcggcagcc aagg                                    34

<210> SEQ ID NO 50
<211> LENGTH: 35
<212> TYPE: DNA
<213> ORGANISM: Artificial sequence
<220> FEATURE:
<223> OTHER INFORMATION: Synthetic

<400> SEQUENCE: 50
agtagtagag ctgcccaatg cgttgccttg ggagc                                   35

<210> SEQ ID NO 51
<211> LENGTH: 35
<212> TYPE: DNA
<213> ORGANISM: Artificial sequence
<220> FEATURE:
<223> OTHER INFORMATION: Synthetic

<400> SEQUENCE: 51
gtattgaaga aaccggttac agatacgcag caaac                                   35

<210> SEQ ID NO 52
<211> LENGTH: 34
<212> TYPE: DNA
<213> ORGANISM: Artificial sequence
<220> FEATURE:
<223> OTHER INFORMATION: Synthetic

<400> SEQUENCE: 52
atcaagcccc atatccaaga aacaataaac cact                                    34

<210> SEQ ID NO 53
<211> LENGTH: 34
<212> TYPE: DNA
<213> ORGANISM: Artificial sequence
<220> FEATURE:
<223> OTHER INFORMATION: Synthetic

<400> SEQUENCE: 53
agacgcacgc ccgaagcatc aacggcttgg aggc                                    34

<210> SEQ ID NO 54
<211> LENGTH: 10
<212> TYPE: DNA
<213> ORGANISM: Artificial sequence
<220> FEATURE:
<223> OTHER INFORMATION: Synthetic

<400> SEQUENCE: 54
gtgtaagtct                                                               10

<210> SEQ ID NO 55
<211> LENGTH: 10
<212> TYPE: DNA
<213> ORGANISM: Artificial sequence
<220> FEATURE:
<223> OTHER INFORMATION: Synthetic

<400> SEQUENCE: 55
tccttgatga                                                               10
```

-continued

```
<210> SEQ ID NO 56
<211> LENGTH: 10
<212> TYPE: DNA
<213> ORGANISM: Artificial sequence
<220> FEATURE:
<223> OTHER INFORMATION: Synthetic

<400> SEQUENCE: 56
aacagcggcg                                                          10

<210> SEQ ID NO 57
<211> LENGTH: 10
<212> TYPE: DNA
<213> ORGANISM: Artificial sequence
<220> FEATURE:
<223> OTHER INFORMATION: Synthetic

<400> SEQUENCE: 57
gttgccgcgc                                                          10

<210> SEQ ID NO 58
<211> LENGTH: 10
<212> TYPE: DNA
<213> ORGANISM: Artificial sequence
<220> FEATURE:
<223> OTHER INFORMATION: Synthetic

<400> SEQUENCE: 58
ctagctctaa                                                          10

<210> SEQ ID NO 59
<211> LENGTH: 10
<212> TYPE: DNA
<213> ORGANISM: Artificial sequence
<220> FEATURE:
<223> OTHER INFORMATION: Synthetic

<400> SEQUENCE: 59
tctttgctga                                                          10

<210> SEQ ID NO 60
<211> LENGTH: 9
<212> TYPE: DNA
<213> ORGANISM: Artificial sequence
<220> FEATURE:
<223> OTHER INFORMATION: Synthetic

<400> SEQUENCE: 60 gattcggca                                                            9

<210> SEQ ID NO 61
<211> LENGTH: 10
<212> TYPE: DNA
<213> ORGANISM: Artificial sequence
<220> FEATURE:
<223> OTHER INFORMATION: Synthetic

<400> SEQUENCE: 61
cggcggatgt                                                          10

<210> SEQ ID NO 62
<211> LENGTH: 10
<212> TYPE: DNA
<213> ORGANISM: Artificial sequence
<220> FEATURE:
<223> OTHER INFORMATION: Synthetic
```

-continued

```
<400> SEQUENCE: 62
gatttcggca                                                          10

<210> SEQ ID NO 63
<211> LENGTH: 10
<212> TYPE: DNA
<213> ORGANISM: Artificial sequence
<220> FEATURE:
<223> OTHER INFORMATION: Synthetic

<400> SEQUENCE: 63
gcaatacacg                                                          10

<210> SEQ ID NO 64
<211> LENGTH: 10
<212> TYPE: DNA
<213> ORGANISM: Artificial sequence
<220> FEATURE:
<223> OTHER INFORMATION: Synthetic

<400> SEQUENCE: 64
cggctttgcg                                                          10

<210> SEQ ID NO 65
<211> LENGTH: 10
<212> TYPE: DNA
<213> ORGANISM: Artificial sequence
<220> FEATURE:
<223> OTHER INFORMATION: Synthetic

<400> SEQUENCE: 65
acacaatgct                                                          10

<210> SEQ ID NO 66
<211> LENGTH: 10
<212> TYPE: DNA
<213> ORGANISM: Artificial sequence
<220> FEATURE:
<223> OTHER INFORMATION: Synthetic

<400> SEQUENCE: 66
gggaatggcg                                                          10

<210> SEQ ID NO 67
<211> LENGTH: 10
<212> TYPE: DNA
<213> ORGANISM: Artificial sequence
<220> FEATURE:
<223> OTHER INFORMATION: Synthetic

<400> SEQUENCE: 67
ttgaccccaa                                                          10

<210> SEQ ID NO 68
<211> LENGTH: 10
<212> TYPE: DNA
<213> ORGANISM: Artificial sequence
<220> FEATURE:
<223> OTHER INFORMATION: Synthetic

<400> SEQUENCE: 68
gcgccagcag                                                          10

<210> SEQ ID NO 69
<211> LENGTH: 10
```

-continued

```
<212> TYPE: DNA
<213> ORGANISM: Artificial sequence
<220> FEATURE:
<223> OTHER INFORMATION: Synthetic

<400> SEQUENCE: 69
gagtaagtct                                                              10

<210> SEQ ID NO 70
<211> LENGTH: 10
<212> TYPE: DNA
<213> ORGANISM: Artificial sequence
<220> FEATURE:
<223> OTHER INFORMATION: Synthetic

<400> SEQUENCE: 70
cagcaacagc                                                              10

<210> SEQ ID NO 71
<211> LENGTH: 10
<212> TYPE: DNA
<213> ORGANISM: Artificial sequence
<220> FEATURE:
<223> OTHER INFORMATION: Synthetic

<400> SEQUENCE: 71
tgtctaaggg                                                              10

<210> SEQ ID NO 72
<211> LENGTH: 10
<212> TYPE: DNA
<213> ORGANISM: Artificial sequence
<220> FEATURE:
<223> OTHER INFORMATION: Synthetic

<400> SEQUENCE: 72
ggaaacggcg                                                              10

<210> SEQ ID NO 73
<211> LENGTH: 10
<212> TYPE: DNA
<213> ORGANISM: Artificial sequence
<220> FEATURE:
<223> OTHER INFORMATION: Synthetic

<400> SEQUENCE: 73
gatttcggaa                                                              10

<210> SEQ ID NO 74
<211> LENGTH: 10
<212> TYPE: DNA
<213> ORGANISM: Artificial sequence
<220> FEATURE:
<223> OTHER INFORMATION: Synthetic

<400> SEQUENCE: 74
tcacacaact                                                              10

<210> SEQ ID NO 75
<211> LENGTH: 10
<212> TYPE: DNA
<213> ORGANISM: Artificial sequence
<220> FEATURE:
<223> OTHER INFORMATION: Synthetic

<400> SEQUENCE: 75
```

-continued

```
tcagccgcct                                                               10

<210> SEQ ID NO 76
<211> LENGTH: 10
<212> TYPE: DNA
<213> ORGANISM: Artificial sequence
<220> FEATURE:
<223> OTHER INFORMATION: Synthetic

<400> SEQUENCE: 76
tccttgctga                                                               10

<210> SEQ ID NO 77
<211> LENGTH: 42
<212> TYPE: DNA
<213> ORGANISM: Artificial sequence
<220> FEATURE:
<223> OTHER INFORMATION: Synthetic

<400> SEQUENCE: 77
agggcgaggg cgatgccacc tacggcaagc tgaccctgaa gt                           42

<210> SEQ ID NO 78
<211> LENGTH: 42
<212> TYPE: DNA
<213> ORGANISM: Artificial sequence
<220> FEATURE:
<223> OTHER INFORMATION: Synthetic

<400> SEQUENCE: 78
acttcagggt cagcttgccg taggtggcat cgccctcgcc ct                           42

<210> SEQ ID NO 79
<211> LENGTH: 42
<212> TYPE: DNA
<213> ORGANISM: Artificial sequence
<220> FEATURE:
<223> OTHER INFORMATION: Synthetic

<400> SEQUENCE: 79
agttcaagac catctacatg gccaagaagc ccgtgcaact gc                           42

<210> SEQ ID NO 80
<211> LENGTH: 42
<212> TYPE: DNA
<213> ORGANISM: Artificial sequence
<220> FEATURE:
<223> OTHER INFORMATION: Synthetic

<400> SEQUENCE: 80
gcagttgcac gggcttcttg gccatgtaga tggtcttgaa ct                           42

<210> SEQ ID NO 81
<211> LENGTH: 42
<212> TYPE: DNA
<213> ORGANISM: Artificial sequence
<220> FEATURE:
<223> OTHER INFORMATION: Synthetic

<400> SEQUENCE: 81
agttaagggt ttggggaagc actgggccaa gagtcaggaa aa                           42

<210> SEQ ID NO 82
<211> LENGTH: 42
<212> TYPE: DNA
<213> ORGANISM: Artificial sequence
```

```
<220> FEATURE:
<223> OTHER INFORMATION: Synthetic

<400> SEQUENCE: 82
ttttcctgac tcttggccca gtgcttcccc aaacccttaa ct                      42

<210> SEQ ID NO 83
<211> LENGTH: 42
<212> TYPE: DNA
<213> ORGANISM: Artificial sequence
<220> FEATURE:
<223> OTHER INFORMATION: Synthetic

<400> SEQUENCE: 83
aggggcttcg ctgggggagc ctcggcttct tctgggagaa aa                      42

<210> SEQ ID NO 84
<211> LENGTH: 42
<212> TYPE: DNA
<213> ORGANISM: Artificial sequence
<220> FEATURE:
<223> OTHER INFORMATION: Synthetic

<400> SEQUENCE: 84
ttttctccca gaagaagccg aggctccccc agcgaagccc ct                      42

<210> SEQ ID NO 85
<211> LENGTH: 834
<212> TYPE: PRT
<213> ORGANISM: Neisseria lactamica

<400> SEQUENCE: 85

Met Asn Phe Asp Tyr Ile Ala His Ala Arg Gln Asp Ser Ser Lys Asn
1               5                   10                  15

Trp His Ser His Pro Leu Gln Lys His Leu Gln Lys Val Ala Gln Leu
            20                  25                  30

Ala Lys Arg Phe Ala Gly Arg Tyr Gly Ser Leu Phe Ala Glu Tyr Ala
        35                  40                  45

Gly Leu Leu His Asp Leu Gly Lys Phe Gln Glu Ser Phe Gln Lys Tyr
    50                  55                  60

Ile Arg Asn Ala Ser Gly Phe Glu Lys Glu Asn Ala His Leu Glu Asp
65                  70                  75                  80

Val Glu Ser Thr Lys Leu Arg Lys Ile Pro His Ser Thr Ala Gly Ala
                85                  90                  95

Lys Tyr Ala Val Glu Arg Leu Asn Pro Phe Phe Gly His Leu Leu Ala
            100                 105                 110

Tyr Leu Ile Ala Gly His His Ala Gly Leu Ala Asp Trp Tyr Asp Lys
        115                 120                 125

Gly Ser Leu Lys Arg Arg Leu Gln Gln Ala Asp Asp Glu Leu Ala Ala
    130                 135                 140

Ser Leu Ser Gly Phe Val Glu Ser Ser Leu Pro Glu Asp Phe Phe Pro
145                 150                 155                 160

Leu Ser Asp Asp Asp Leu Met Arg Asp Phe Phe Ala Phe Trp Glu Asp
                165                 170                 175

Gly Ala Lys Leu Glu Glu Leu His Ile Trp Met Arg Phe Leu Phe Ser
            180                 185                 190

Cys Leu Val Asp Ala Asp Phe Leu Asp Thr Glu Ala Phe Met Asn Gly
        195                 200                 205

Tyr Ala Asp Ala Asp Thr Ala Gln Ala Ala Gly Leu Arg Pro Lys Phe
```

-continued

```
          210              215              220

Pro Gly Leu Asp Glu Leu His Arg Arg Tyr Glu Gln Tyr Met Ala Gln
225              230              235              240

Leu Ser Glu Lys Ala Asp Lys Asn Ser Ser Leu Asn Gln Glu Arg His
             245              250              255

Ala Ile Leu Gln Gln Cys Phe Ser Ala Ala Glu Thr Asp Arg Thr Leu
             260              265              270

Phe Ser Leu Thr Val Pro Thr Gly Gly Gly Lys Thr Leu Ala Ser Leu
             275              280              285

Gly Phe Ala Leu Lys His Ala Leu Lys Phe Gly Lys Lys Arg Ile Ile
             290              295              300

Tyr Ala Ile Pro Phe Thr Ser Ile Ile Glu Gln Asn Ala Asn Val Phe
305              310              315              320

Arg Asn Ala Leu Gly Asp Asp Val Val Leu Glu His His Ser Asn Leu
             325              330              335

Glu Val Lys Glu Asp Lys Glu Thr Ala Lys Thr Arg Leu Ala Thr Glu
             340              345              350

Asn Trp Asp Ala Pro Leu Ile Val Thr Thr Asn Val Gln Leu Phe Glu
             355              360              365

Ser Leu Phe Ala Ala Lys Thr Ser Arg Cys Arg Lys Ile His Asn Ile
             370              375              380

Ala Asp Ser Val Val Ile Leu Asp Glu Ala Gln Gln Leu Pro Arg Asp
385              390              395              400

Phe Gln Lys Pro Ile Thr Asp Met Met Arg Val Leu Ala Arg Asp Tyr
             405              410              415

Gly Val Thr Phe Val Leu Cys Thr Ala Thr Gln Pro Glu Leu Gly Lys
             420              425              430

Asn Ile Asp Ala Phe Gly Arg Thr Ile Leu Glu Gly Leu Pro Asp Val
             435              440              445

Arg Glu Ile Val Ala Asp Lys Ile Ala Leu Ser Glu Lys Leu Arg Arg
             450              455              460

Val Arg Ile Lys Met Pro Pro Asn Gly Glu Thr Gln Ser Trp Gln
465              470              475              480

Lys Ile Ala Asp Glu Ile Ala Ala Arg Pro Cys Val Leu Ala Val Val
             485              490              495

Asn Thr Arg Lys His Ala Gln Lys Leu Phe Ala Ala Leu Pro Ser Asn
             500              505              510

Gly Ile Lys Leu His Leu Ser Ala Asn Met Cys Ala Thr His Cys Ser
             515              520              525

Glu Val Ile Ala Leu Val Arg Arg Tyr Leu Ala Leu Tyr Arg Ala Gly
             530              535              540

Ser Leu His Lys Pro Leu Trp Leu Val Ser Thr Gln Leu Ile Glu Ala
545              550              555              560

Gly Val Asp Leu Asp Phe Pro Cys Val Tyr Arg Ala Met Ala Gly Leu
             565              570              575

Asp Ser Ile Ala Gln Ala Ala Gly Arg Cys Asn Arg Glu Gly Lys Leu
             580              585              590

Pro Gln Leu Gly Glu Val Val Val Phe Arg Ala Glu Glu Gly Ala Pro
             595              600              605

Ser Gly Ser Leu Lys Gln Gly Gln Asp Ile Thr Glu Glu Met Leu Lys
             610              615              620

Ala Gly Leu Leu Asp Asp Pro Leu Ser Pro Leu Ala Phe Ala Glu Tyr
625              630              635              640
```

Phe Arg Arg Phe Asn Gly Lys Gly Asp Val Asp Lys His Gly Ile Thr
                645             650             655

Thr Leu Leu Thr Ala Glu Ala Ser Asn Glu Asn Pro Leu Ala Ile Lys
                660             665             670

Phe Arg Thr Ala Ala Glu Arg Phe His Leu Ile Asp Asn Gln Gly Val
                675             680             685

Ala Leu Ile Val Pro Phe Ile Pro Leu Ala His Trp Glu Lys Asp Gly
                690             695             700

Ser Pro Gln Ile Val Glu Ala Asn Glu Leu Asp Asp Phe Phe Arg Arg
705             710             715             720

His Leu Asp Gly Val Glu Val Ser Glu Trp Gln Asp Ile Leu Asp Lys
                725             730             735

Gln Arg Phe Pro Gln Pro Pro Asp Asn Ser Phe Gly Gln Thr Asp Gln
                740             745             750

Pro Leu Leu Pro Glu Pro Phe Glu Ser Trp Phe Gly Leu Leu Glu Ser
                755             760             765

Asp Pro Leu Lys His Lys Trp Val Tyr Arg Lys Leu Gln Arg Tyr Thr
                770             775             780

Ile Thr Val Tyr Glu His Glu Leu Lys Lys Leu Pro Glu His Ala Val
785             790             795             800

Phe Ser Arg Ala Gly Leu Leu Val Leu Asp Lys Gly Tyr Tyr Lys Ala
                805             810             815

Val Leu Gly Ala Asp Phe Asp Asp Ala Ala Trp Leu Pro Glu Asn Ser
                820             825             830

Val Leu

<210> SEQ ID NO 86
<211> LENGTH: 214
<212> TYPE: PRT
<213> ORGANISM: Neisseria lactamica

<400> SEQUENCE: 86

Met Arg Phe Ile Leu Glu Ile Ser Gly Asp Leu Ala Cys Phe Thr Arg
1               5               10              15

Ser Glu Leu Lys Val Glu Arg Val Ser Tyr Pro Val Ile Thr Pro Ser
                20              25              30

Ala Ala Arg Asn Ile Leu Met Ala Ile Leu Trp Lys Pro Ala Ile Arg
                35              40              45

Trp Lys Val Leu Lys Ile Glu Ile Leu Lys Pro Ile Gln Trp Thr Asn
        50              55              60

Ile Arg Arg Asn Glu Val Gly Thr Lys Met Ser Glu Arg Ser Gly Ser
65              70              75              80

Leu Tyr Ile Glu Asp Asn Arg Gln Gln Arg Ala Ser Met Leu Leu Lys
                85              90              95

Asp Val Ala Tyr Arg Ile His Ala Asp Phe Asp Met Thr Ser Glu Ala
                100             105             110

Gly Glu Ser Asp Asn Tyr Val Lys Phe Ala Glu Met Phe Lys Arg Arg
                115             120             125

Ala Lys Lys Gly Gln Tyr Phe His Gln Pro Tyr Leu Gly Cys Arg Glu
        130             135             140

Phe Pro Cys Asp Phe Arg Leu Leu Glu Lys Ala Glu Asp Gly Leu Pro
145             150             155             160

Leu Glu Asp Ile Thr Gln Asp Phe Gly Phe Met Leu Tyr Asp Met Asp
                165             170             175

-continued

```
Phe Ser Lys Ser Asp Pro Arg Asp Ser Asn Asn Ala Glu Pro Met Phe
            180             185             190

Tyr Gln Cys Lys Ala Val Asn Gly Val Ile Thr Val Pro Pro Ala Asp
        195             200             205

Ser Glu Glu Val Lys Arg
    210

<210> SEQ ID NO 87
<211> LENGTH: 585
<212> TYPE: PRT
<213> ORGANISM: Neisseria lactamica

<400> SEQUENCE: 87

Met Ile Leu His Ala Leu Thr Gln Tyr Tyr Gln Arg Lys Ala Glu Ser
1               5               10              15

Asp Gly Gly Ile Ala Gln Glu Gly Phe Glu Asn Lys Glu Ile Pro Phe
                20              25              30

Ile Ile Val Ile Asp Lys Gln Gly Asn Phe Ile Gln Leu Glu Asp Thr
            35              40              45

Arg Glu Leu Lys Val Lys Lys Val Gly Arg Thr Phe Leu Val Pro
    50              55              60

Lys Gly Leu Gly Arg Ser Gly Ser Lys Ser Tyr Glu Val Ser Asn Leu
65              70              75              80

Leu Trp Asp His Tyr Gly Tyr Val Leu Ala Tyr Ala Gly Glu Lys Gly
                85              90              95

Gln Glu Gln Ala Asp Lys Gln His Ala Ser Phe Thr Ala Lys Val Asn
            100             105             110

Glu Leu Lys Gln Ala Leu Pro Asp Asp Ala Gly Val Thr Ala Val Ala
        115             120             125

Ala Phe Leu Ser Ser Ala Glu Glu Lys Ser Lys Val Met Gln Ala Ala
    130             135             140

Asn Trp Ala Glu Cys Ala Lys Val Lys Gly Cys Asn Leu Ser Phe Arg
145             150             155             160

Leu Val Asp Glu Ala Val Asp Leu Val Cys Gln Ser Lys Ala Val Arg
                165             170             175

Glu Tyr Val Ser Gln Ala Asn Gln Thr Gln Ser Asp Asn Val Gln Lys
            180             185             190

Gly Ile Cys Leu Val Thr Gly Lys Ala Ala Pro Ile Ala Arg Leu His
        195             200             205

Asn Ala Val Lys Gly Val Asn Ala Lys Pro Ala Pro Phe Ala Ser Val
    210             215             220

Asn Leu Ser Ala Phe Glu Ser Tyr Gly Lys Glu Gln Gly Phe Ile Phe
225             230             235             240

Pro Val Gly Glu Gln Ala Met Phe Glu Tyr Thr Thr Ala Leu Asn Thr
                245             250             255

Leu Leu Ala Ser Glu Asn Arg Phe Arg Ile Gly Asp Val Thr Ala Val
            260             265             270

Cys Trp Gly Ala Lys Arg Thr Pro Leu Glu Glu Ser Leu Ala Ser Met
        275             280             285

Ile Asn Gly Gly Gly Lys Asp Lys Pro Asp Glu His Ile Asp Ala Val
    290             295             300

Lys Thr Leu Tyr Lys Ser Leu Tyr Asn Gly Gln Tyr Gln Lys Pro Asp
305             310             315             320

Gly Lys Glu Lys Phe Tyr Leu Leu Gly Leu Ser Pro Asn Ser Ala Arg
```

```
                325                 330                 335

Ile Val Val Arg Phe Trp His Glu Thr Thr Val Ala Ala Leu Ser Glu
            340                 345                 350

Ser Ile Ala Ala Trp Tyr Asp Asp Leu Gln Met Val Arg Gly Glu Asn
            355                 360                 365

Ser Pro Tyr Pro Glu Tyr Met Pro Leu Pro Arg Leu Leu Gly Asn Leu
    370                 375                 380

Val Leu Asp Gly Lys Met Glu Asn Leu Pro Ser Asp Leu Ile Ala Gln
385                 390                 395                 400

Ile Thr Asp Ala Ala Leu Asn Asn Arg Val Leu Pro Val Ser Leu Leu
                405                 410                 415

Gln Ala Ala Leu Arg Arg Asn Lys Ala Glu Gln Lys Ile Thr Tyr Gly
            420                 425                 430

Arg Ala Ser Leu Leu Lys Ala Tyr Ile Asn Arg Ala Ile Arg Ala Gly
            435                 440                 445

Arg Leu Lys Asn Met Lys Glu Leu Thr Met Gly Leu Asp Arg Asn Arg
    450                 455                 460

Gln Asp Ile Gly Tyr Val Leu Gly Arg Leu Phe Ala Val Leu Glu Lys
465                 470                 475                 480

Ile Gln Ala Glu Ala Asn Pro Gly Leu Asn Ala Thr Ile Ala Asp Arg
                485                 490                 495

Tyr Phe Gly Ser Ala Ser Ser Thr Pro Ile Ala Val Phe Gly Thr Leu
            500                 505                 510

Met Arg Leu Leu Pro His His Leu Asn Lys Leu Glu Phe Glu Gly Arg
            515                 520                 525

Ala Val Gln Leu Gln Trp Glu Ile Arg Gln Ile Leu Glu His Cys Gln
    530                 535                 540

Arg Phe Pro Asn His Leu Asn Leu Glu Gln Gln Gly Leu Phe Ala Ile
545                 550                 555                 560

Gly Tyr Tyr His Glu Thr Gln Phe Leu Phe Thr Lys Asp Ala Leu Lys
                565                 570                 575

Asn Leu Phe Asn Glu Ala Lys Thr Ala
            580                 585
```

<210> SEQ ID NO 88
<211> LENGTH: 283
<212> TYPE: PRT
<213> ORGANISM: Neisseria lactamica

<400> SEQUENCE: 88

```
Met Thr Ile Glu Lys Arg Tyr Asp Phe Val Phe Leu Phe Asp Val Gln
1               5                   10                  15

Asp Gly Asn Pro Asn Gly Asp Pro Asp Ala Gly Asn Leu Pro Arg Ile
            20                  25                  30

Asp Pro Gln Thr Gly Glu Gly Leu Val Thr Asp Val Cys Leu Lys Arg
        35                  40                  45

Lys Val Arg Asn Phe Ile Gln Met Thr Gln Asn Asp Glu His His Asp
    50                  55                  60

Ile Phe Ile Arg Glu Lys Gly Ile Leu Asn Asn Leu Ile Asp Glu Ala
65                  70                  75                  80

His Glu Gln Glu Asn Val Lys Gly Lys Glu Lys Gly Glu Lys Thr Glu
                85                  90                  95

Ala Ala Arg Gln Tyr Met Cys Ser Arg Tyr Tyr Asp Ile Arg Thr Phe
            100                 105                 110
```

-continued

```
Gly Ala Val Met Thr Thr Gly Lys Asn Ala Gly Gln Val Arg Gly Pro
        115                 120                 125

Val Gln Leu Thr Phe Ser Arg Ser Ile Asp Pro Ile Met Thr Leu Glu
        130                 135                 140

His Ser Ile Thr Arg Met Ala Val Thr Asn Glu Lys Asp Ala Ser Glu
145                 150                 155                 160

Thr Gly Asp Asn Arg Thr Met Gly Arg Lys Phe Thr Val Pro Tyr Gly
                165                 170                 175

Leu Tyr Arg Cys His Gly Phe Ile Ser Thr His Phe Ala Lys Gln Thr
                180                 185                 190

Gly Phe Ser Glu Asn Asp Leu Glu Leu Phe Trp Gln Ala Leu Val Asn
                195                 200                 205

Met Phe Asp His Asp His Ser Ala Ala Arg Gly Gln Met Asn Ala Arg
        210                 215                 220

Gly Leu Tyr Val Phe Glu His Ser Asn Asn Leu Gly Asp Ala Pro Ala
225                 230                 235                 240

Asp Ser Leu Phe Lys Arg Ile Gln Val Val Lys Lys Asp Gly Val Glu
                245                 250                 255

Val Val Arg Ser Phe Asp Asp Tyr Leu Val Ser Val Asp Asp Lys Asn
                260                 265                 270

Leu Glu Glu Thr Lys Leu Leu Arg Lys Leu Gly
        275                 280
```

<210> SEQ ID NO 89
<211> LENGTH: 35
<212> TYPE: DNA
<213> ORGANISM: Artificial sequence
<220> FEATURE:
<223> OTHER INFORMATION: Synthetic

<400> SEQUENCE: 89
aagaccatct acatggccaa gaagcccgtg caact                              35

<210> SEQ ID NO 90
<211> LENGTH: 35
<212> TYPE: DNA
<213> ORGANISM: Artificial sequence
<220> FEATURE:
<223> OTHER INFORMATION: Synthetic

<400> SEQUENCE: 90
ctgactcttg gcccagtgct tccccaaacc cttaa                              35

<210> SEQ ID NO 91
<211> LENGTH: 35
<212> TYPE: DNA
<213> ORGANISM: Artificial sequence
<220> FEATURE:
<223> OTHER INFORMATION: Synthetic

<400> SEQUENCE: 91
ttactgtccc cttctgggct cactatgctg ccgcc                              35